(12) United States Patent
Sligar et al.

(10) Patent No.: US 6,235,500 B1
(45) Date of Patent: May 22, 2001

(54) OXYGEN-BINDING HEME PROTEINS INCORPORATING CIRCULARLY-PERMUTED GLOBINS

(75) Inventors: Stephen G. Sligar, Urbana; Kevin Sanders, Champaign, both of IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/269,592

(22) PCT Filed: Sep. 26, 1997

(86) PCT No.: PCT/US97/17294

§ 371 Date: Jun. 28, 1999

§ 102(e) Date: Jun. 28, 1999

(87) PCT Pub. No.: WO98/13386

PCT Pub. Date: Apr. 2, 1998

Related U.S. Application Data

(60) Provisional application No. 60/026,831, filed on Sep. 27, 1996.

(51) Int. Cl.$^7$ .......................... C12P 21/06; C07K 17/00; C07K 14/805

(52) U.S. Cl. .................. 435/69.6; 435/252.3; 435/320.1; 435/325; 536/23.5; 530/385

(58) Field of Search ........................... 530/385; 536/23.5; 435/69.6, 320.1, 325, 252.3

(56) References Cited

U.S. PATENT DOCUMENTS

| | | | |
|---|---|---|---|
| 5,028,588 | 7/1991 | Hoffman et al. | 514/6 |
| 5,049,493 | 9/1991 | Khosla et al. | 435/69.1 |
| 5,173,426 | 12/1992 | Fischer et al. | 435/252.3 |
| 5,250,665 | 10/1993 | Kluger et al. | 530/385 |
| 5,260,203 | 11/1993 | Ladner et al. | 435/172.3 |
| 5,334,706 | 8/1994 | Przybelski | 530/385 |
| 5,428,007 | 6/1995 | Fischer et al. | 514/6 |
| 5,449,759 | 9/1995 | Hoffman et al. | 530/385 |
| 5,478,806 | 12/1995 | Nho | 514/6 |
| 5,545,727 | 8/1996 | Hoffman et al. | 536/234 |
| 5,563,254 | 10/1996 | Hoffman et al. | 536/23.5 |
| 5,578,564 | 11/1996 | Chivers et al. | 514/6 |
| 5,599,907 | 2/1997 | Anderson et al. | 530/385 |
| 5,631,219 | 5/1997 | Rosenthal et al. | 514/6 |
| 5,661,124 | 8/1997 | Hoffman et al. | 514/6 |
| 5,665,869 | 9/1997 | Ryland et al. | 530/412 |

OTHER PUBLICATIONS

"Hemoglobin Structure", pp. 13–19.

G.K. Ackers, M.L. Doyle, D. Myers, M.A. Daugherty, "Molecular Code For Cooperativity in Hemoglobin", *Science*, vol. 255, pp. 54–63 (Jan. 3, 1992).

R.A. Dracker, "The Development And Use Of Oxygen–Carrying Blood Substitutes", *Immunological Investigations*, vol. 24, Nos. 1 and 2, pp. 403–410 (1995).

G. Fermi, M.F. Perutz, B. Shaanan, "The Crystal Structure Of Human Deoxyhaemoglobin At 1–74 Å Resolution", *J. Mol. Biol.*, vol. 175, pp. 159–174 (1984).

C. Giulivi, K.J.A. Davies, "Hydrogen Peroxide–Mediated Ferrylehemoglobin Generation In Vitro And In Red Blood Cells", *Meth. Enzymol.*, vol. 231, pp. 490–496 (1994).

D.P. Goldenberg, T.E. Creighton, "Circular and Circularly Permuted Forms Of Bovine Pancreatic Trypsin Inhibitor", *J. Mol. Biol.*, vol. 165, pp. 407–413 (1983).

S.A. Gould, L.R. Sehgal, H.L. Sehgal, G.S. Moss, "The Development Of Hemoglobin Solutions As Red Cell Substitutes: Hemoglobin Solutions", *Transfus. Sci.*, vol. 16, No. 1, pp. 5–17 (1995).

R.A. Hernan, H.L. Hui, M.E. Andracki, R.W. Noble, S.G. Sligar, J.A. Walder, R.Y. Walder, "Human Hemoglobin Expression In *Escherichia coli*: Importance Of Optimal Codon Usage", *Biochemistry*, vol. 31, pp. 8619–8628 (1992).

S.J. Horvath, J.R. Firca, T. Hunkapiller, M.W. Hunkapiller, L. Hood, "An Automated DNA Synthesizer Employing Deoxynucleoside 3′–Phosphoramidites", *Meth. Enzymol.*, vol. 154, pp. 314–326 (1987).

L. Jia, C. Bonaventura, J. Bonaventure, J.S. Stamler, "S–Nitrosohaemoglobin: A Dynamic Activity Of Blood Involved In Vascular Control", *Nature*, vol. 380, pp. 221–226 (Mar. 21, 1996).

R.J. Kaufman, "Chapter 7: Medical Oxygen Transport Using Perfluorochemicals", pp. 127–162.

D.E. Koshland, Jr., G. Némethy, D. Filmer, "Comparison Of Experimental Binding Data And Theoretical Models In Proteins Containing Subunits," *Biochemistry*, vol. 5, No. 1, pp. 365–385 (Jan. 1966).

R. Kumar, "Recombinant Hemoglobins As Blood Substitutes: A Biotechnology Perspective", *Blood Substitute: Recombinant Hemoglobin*, pp. 150–158 (1995).

D. Looker, D. Abbott–Brown, P. Cozart, S. Durfee, S. Hoffman, A.J. Mathews, J. Miller–Roehrich, S. Shoemaker, S. Trimble, G. Fermi, N.H. Komiyama, K. Nagai, G.L. Stetler, "A Human Recombinant Haemoglobin Designed For Use As A Blood Substitute", *Nature*, vol. 356, pp. 258–260 (Mar. 19, 1992).

(List continued on next page.)

Primary Examiner—Karen Cochrane Carlson
(74) Attorney, Agent, or Firm—Woodard, Emhardt, Naughton, Moriarty & McNett

(57) ABSTRACT

Described are preferred oxygen-binding heme proteins which include at least one hemoglobin molecule incorporating at least one circularly permuted globin, especially an alpha globin. More preferred heme proteins of the invention include high molecular weight hemoglobin multimers. Also described are polynucleotides encoding proteins of the invention, and vectors and host cells including the same.

28 Claims, 21 Drawing Sheets

OTHER PUBLICATIONS

T. Pan, O.C. Uhlenbeck, "Circularly Permuted DNA, RNA And Proteins—A Review", *Gene*, vol. 125, pp. 111–114 (1993).

T. Repka, R.P. Hebbel, "Hydroxyl Radical Formation By Sickle Erythrocyte Membranes: Role Of Pathologic Iron Deposits And Cytoplasmic Reducing Agents" *Blood*, vol. 78, No. 10, pp. 2753–2758 (Nov. 15, 1991).

B. Shaanan, "Structure Of Human Oxyhaemoglobin At 2–1 Å Resolution", *J. Mol. Biol.*, vol. 171, pp. 31–59 (1983).

T.-J. Shen, N.T. Ho, V. Simplaceanu, M. Zou, B.N. Green, M.F. Tam, C. Ho, "Production Of Unmodified Human Adult Hemoglobin In *Escherichia coli*", *Proc. Natl. Acad. Sci., USA*, vol. 90, pp. 8108–8112 (Sep. 1993).

J.F. Wong, "Blood Substitutes Revisited—Trails And Tribulations Of Two Biotech Firms", *Wall Street Journal*, pp. 20–21 (May 1, 1996).

Y. Yamamoto, G.N. LaMar, "$^1$H NMR Study Of Dynamics And Thermodynamics Of Heme Rotational Disorder In Native And Reconstituted Hemoglobin A", *Biochemistry*, vol. 25, pp. 5288–5297 (1986).

Figure 2

Di-alpha linking cassette

```
5'-TCGACTGTTCTGACTTCTAAATACCGCGGTGTTCTGTCTCCGGCAGACAAAACTAACGTTAAAGCTGCTTGGGGT-
   3'-GACAAGACTGAAGATTTATGGCGCCACAAGACAGAGGCCGTCTGTTTTGATTGCAATTTCGACGAACCCCA-

-AAAGTTGGAGCT-3'
-TTTCAACC-5'
```

Figure 3

Di-alpha Sequence

```
XbaI                                            1/37
TCT AGA ATA ACT AAC TAA AGG AGA ACA ACA ACC ATG CTG TCT CCG GCA GAC AAA ACT AAC
AGA TCT TAT TGA TTG ATT TCC TCT TGT TGT TGG TAC GAC AGA GGC CGT CTG TTT TGA TTG
                                                met leu ser pro ala asp lys thr asn 10/64                                       20/94
GTT AAA GCT GCT TGG GGT AAA GTT GGA GCT CAT GCT GGT GAA TAC GGT GCT GAA GCA CTC
CAA TTT CGA CGA ACC CCA TTT CAA CCT CGA GTA CGA CCA CTT ATG CCA CGA CTT CGT GAG
val lys ala ala trp gly lys val gly ala his ala gly glu tyr gly ala glu ala leu 30/124                                      40/154
GAG CGT ATG TTC CTG TCT TTC CCG ACT ACT AAA ACG TAC TTC CCG CAT TTC GAC CTG TCT
CTC GCA TAC AAG GAC AGA AAG GGC TGA TGA TTT TGC ATG AAG GGC GTA AAG CTG GAC AGA
glu arg met phe leu ser phe pro thr thr lys thr tyr phe pro his phe asp leu ser 50/184                                      60/214
CAT GGA TCC GCT CAG GTT AAA GGT CAT GGT AAA AAA GTT GCT GAC GCG TTG ACT AAC GCT
GTA CCT AGG CGA GTC CAA TTT CCA GTA CCA TTT TTT CAA CGA CTG CGC AAC TGA TTG CGA
his gly ser ala gln val lys gly his gly lys lys val ala asp ala leu thr asn ala 70/244                                      80/274
GTT GCT CAT GTT GAC GAC ATG CCG AAC GCT CTG TCC GCT CTG TCA GAT CTT CAT GCT CAT
CAA CGA GTA CAA CTG CTG TAC GGC TTG CGA GAC AGG CGA GAC AGT CTA GAA GTA CGA GTA
val ala his val asp asp met pro asn ala leu ser ala leu ser asp leu his ala his 90/304                                     100/334
AAA CTG CGC GTT GAC CCG GTA AAC TTC AAG CTT CTG TCT CAT TGC CTG CTG GTT ACT CTG
TTT GAC GCG CAA CTG GGC CAT TTG AAG TTC GAA GAC AGA GTA ACG GAC GAC CAA TGA GAC
lys leu arg val asp pro val asn phe lys leu leu ser his cys leu leu val thr leu 110/364                                     120/394
GCT GCT CAT CTG CCG GCA GAA TTC ACT CCG GCT GTT CAT GCT TCT CTG GAT AAA TTC CTG
CGA CGA GTA GAC GGC CGT CTT AAG TGA GGC CGA CAA GTA CGA AGA GAC CTA TTT AAG GAC
ala ala his leu pro ala glu phe thr pro ala val his ala ser leu asp lys phe leu SalI                                         140/454
GCT TCT GTG TCG ACT GTT CTG ACT TCT AAA TAC CGC GGT GTT CTG TCT CCG GCA GAC AAA
CGA AGA CAC AGC TGA CAA GAC TGA AGA TTT ATG GCG CCA CAA GAC AGA GGC CGT CTG TTT
ala ser val ser thr val leu thr ser lys tyr arg gly val leu ser pro ala asp lys 150/484                                 SacI
ACT AAC GTT AAA GCT GCT TGG GGT AAA GTT GGA GCT CAT GCT GGT GAA TAC GGT GCT GAA
TGA TTG CAA TTT CGA CGA ACC CCA TTT CAA CCT CGA GTA CGA CCA CTT ATG CCA CGA CTT
thr asn val lys ala ala trp gly lys val gly ala his ala gly glu tyr gly ala glu 170/544                                     180/574
GCA CTC GAG CGT ATG TTC CTG TCT TTC CCG ACT ACT AAA ACG TAC TTC CCG CAT TTC GAC
CGT GAG CTC GCA TAC AAG GAC AGA AAG GGC TGA TGA TTT TGC ATG AAG GGC GTA AAG CTG
ala leu glu arg met phe leu ser phe pro thr thr lys thr tyr phe pro his phe asp
```

Figure 3 (cont.)

```
        190/604                                200/634
CTG TCT CAT GGA TCC GCT CAG GTT AAA GGT CAT GGT AAA AAA GTT GCT GAC GCG TTG ACT
GAC AGA GTA CCT AGG CGA GTC CAA TTT CCA GTA CCA TTT TTT CAA CGA CTG CGC AAC TGA
leu ser his gly ser ala gln val lys gly his gly lys lys val ala asp ala leu thr 210/664                                220/694
AAC GCT GTT GCT CAT GTT GAC GAC ATG CCG AAC GCT CTG TCC GCT CTG TCA GAT CTT CAT
TTG CGA CAA CGA GTA CAA CTG CTG TAC GGC TTG CGA GAC AGG CGA GAC AGT CTA GAA GTA
asn ala val ala his val asp asp met pro asn ala leu ser ala leu ser asp leu his 230/724                                240/754
GCT CAT AAA CTG CGC GTT GAC CCG GTA AAC TTC AAG CTT CTG TCT CAT TGC CTG CTG GTT
CGA GTA TTT GAC GCG CAA CTG GGC CAT TTG AAG TTC GAA GAC AGA GTA ACG GAC GAC CAA
ala his lys leu arg val asp pro val asn phe lys leu leu ser his cys leu leu val 250/784                                260/814
ACT CTG GCT GCT CAT CTG CCG GCA GAA TTC ACT CCG GCT GTT CAT GCT TCT CTG GAT AAA
TGA GAC CGA CGA GTA GAC GGC CGT CTT AAG TGA GGC CGA CAA GTA CGA AGA GAC CTA TTT
thr leu ala ala his leu pro ala glu phe thr pro ala val his ala ser leu asp lys 270/844                                280/874              PstI
TTC CTG GCT TCT GTG TCG ACT GTT CTG ACT TCT AAA TAC CGT TAA TGA CTG CAG
AAG GAC CGA AGA CAC AGC TGA CAA GAC TGA AGA TTT ATG GCA ATT ACT GAC GTC
phe leu ala ser val ser thr val leu thr ser lys tyr arg OCH OPA
```

Figure 4

```
                                              CP1
    XbaI                                      BamHI                            StyI
5'-CTAGAATAACTAACTAAAGGAGAACAACAACCATGTCTCATGGTTCCGCTCAGGTTAAGGGCCATGGTAAAAAA-
3'-TTATTGATTGATTTCCTCTTGTTGTTGGTACAGAGTACCAAGGCGAGTCCAATTCCCGGTACCATTTTTT-

MluI
    GTTGCTGA-3'
    CAACGACTGCGC-5'
                                              CP2
    XhoI                                                                       PstI
5'-TCGAGCGCATGTTCCTGTCTTTCCCGACTACTAAAACGTACTTCCCGCATTTCGACCTGTAATGACTGCA-3'
    3'-GCGTACAAGGACAGAAAGGGCTGATGATTTTGCATGAAGGGCGTAAAGCTGGACATTACTG-5'
```

Figure 7

Circularly Permuted Di-alpha Gene Sequence

```
XbaI                                                1/37    BamHI
TCT AGA ATA ACT AAC TAA AGG AGA ACA ACA ACC ATG TCT CAT GGT TCC GCT CAG GTT AAG
AGA TCT TAT TGA TTG ATT TCC TCT TGT TGT TGG TAC AGA GTA CCA AGG CGA GTC CAA TTC
                                                met ser his gly ser ala gln val lys StyI                      MluI               20/94
GGC CAT GGT AAA AAA GTT GCT GAC GCG TTG ACT AAC GCT GTT GCT CAT GTT GAC GAC ATG
CCG GTA CCA TTT TTT CAA CGA CTG CGC AAC TGA TTG CGA CAA CGA GTA CAA CTG CTG TAC
gly his gly lys lys val ala asp ala leu thr asn ala val ala his val asp asp met 30/124                                  40/154
CCG AAC GCT CTG TCC GCT CTG TCA GAT CTT CAT GCT CAT AAA CTG CGC GTT GAC CCG GTA
GGC TTG CGA GAC AGG CGA GAC AGT CTA GAA GTA CGA GTA TTT GAC GCG CAA CTG GGC CAT
pro asn ala leu ser ala leu ser asp leu his ala his lys leu arg val asp pro val 50/184                                  60/214
AAC TTC AAG CTT CTG TCT CAT TGC CTG CTG GTT ACT CTG GCT GCT CAT CTG CCG GCA GAA
TTG AAG TTC GAA GAC AGA GTA ACG GAC GAC CAA TGA GAC CGA CGA GTA GAC GGC CGT CTT
asn phe lys leu leu ser his cys leu leu val thr leu ala ala his leu pro ala glu 70/244                                  80/274
TTC ACT CCG GCT GTT CAT GCT TCT CTG GAT AAA TTC CTG GCT TCT GTG TCG ACT GTT CTG
AAG TGA GGC CGA CAA GTA CGA AGA GAC CTA TTT AAG GAC CGA AGA CAC AGC TGA CAA GAC
phe thr pro ala val his ala ser leu asp lys phe leu ala ser val ser thr val leu 90/304                                  100/334
ACT TCT AAA TAC CGC GGT GTT CTG TCT CCG GCA GAC AAA ACT AAC GTT AAA GCT GCT TGG
TGA AGA TTT ATG GCG CCA CAA GAC AGA GGC CGT CTG TTT TGA TTG CAA TTT CGA CGA ACC
thr ser lys tyr arg gly val leu ser pro ala asp lys thr asn val lys ala ala trp 110/364                                 120/394
GGT AAA GTT GGA GCT CAT GCT GGT GAA TAC GGT GCT GAA GCA CTC GAG CGT ATG TTC CTG
CCA TTT CAA CCT CGA GTA CGA CCA CTT ATG CCA CGA CTT CGT GAG CTC GCA TAC AAG GAC
gly lys val gly ala his ala gly glu tyr gly ala glu ala leu glu arg met phe leu 130/424                                 140/454        BamHI
TCT TTC CCG ACT ACT AAA ACG TAC TTC CCG CAT TTC GAC CTG TCT CAT GGA TCC GCT CAG
AGA AAG GGC TGA TGA TTT TGC ATG AAG GGC GTA AAG CTG GAC AGA GTA CCT AGG CGA GTC
ser phe pro thr thr lys thr tyr phe pro his phe asp leu ser his gly ser ala gln 150/484                                 160/514
GTT AAA GGT CAT GGT AAA AAA GTT GCT GAC GCG TTG ACT AAC GCT GTT GCT CAT GTT GAC
CAA TTT CCA GTA CCA TTT TTT CAA CGA CTG CGC AAC TGA TTG CGA CAA CGA GTA CAA CTG
val lys gly his gly lys lys val ala asp ala leu thr asn ala val ala his val asp 170/544                                 180/574
GAC ATG CCG AAC GCT CTG TCC GCT CTG TCA GAT CTT CAT GCT CAT AAA CTG CGC GTT GAC
CTG TAC GGC TTG CGA GAC AGG CGA GAC AGT CTA GAA GTA CGA GTA TTT GAC GCG CAA CTG
asp met pro asn ala leu ser ala leu ser asp leu his ala his lys leu arg val asp 190/604                                 200/634
CCG GTA AAC TTC AAG CTT CTG TCT CAT TGC CTG CTG GTT ACT CTG GCT GCT CAT CTG CCG
GGC CAT TTG AAG TTC GAA GAC AGA GTA ACG GAC GAC CAA TGA GAC CGA CGA GTA GAC GGC
pro val asn phe lys leu leu ser his cys leu leu val thr leu ala ala his leu pro 210/664                                 220/694
GCA GAA TTC ACT CCG GCT GTT CAT GCT TCT CTG GAT AAA TTC CTG GCT TCT GTG TCG ACT
CGT CTT AAG TGA GGC CGA CAA GTA CGA AGA GAC CTA TTT AAG GAC CGA AGA CAC AGC TGA
ala glu phe thr pro ala val his ala ser leu asp lys phe leu ala ser val ser thr
```

Figure 7 (cont.)

```
        230/724                                        240/754
GTT CTG ACT TCT AAA TAC CGC GGT GTT CTG TCT CCG GCA GAC AAA ACT AAC GTT AAA GCT
CAA GAC TGA AGA TTT ATG GCG CCA CAA GAC AGA GGC CGT CTG TTT TGA TTG CAA TTT CGA
val leu thr ser lys tyr arg gly val leu ser pro ala asp lys thr asn val lys ala 250/784                                        260/814              XhoI
GCT TGG GGT AAA GTT GGA GCT CAT GCT GGT GAA TAC GGT GCT GAA GCA CTC GAG CGT ATG
CGA ACC CCA TTT CAA CCT CGA GTA CGA CCA CTT ATG CCA CGA CTT CGT GAG CTC GCA TAC
ala trp gly lys val gly ala his ala gly glu tyr gly ala glu ala leu glu arg met 270/844                                        280/874              PstI
TTC CTG TCT TTC CCG ACT ACT AAA ACG TAC TTC CCG CAT TTC GAC CTG TAA TGA CTG CAG
AAG GAC AGA AAG GGC TGA TGA TTT TGC ATG AAG GGC GTA AAG CTG GAC ATT ACT GAC GTC
phe leu ser phe pro thr thr lys thr tyr phe pro his phe asp leu OCH OPA
```

Figure 9

```
                                     TA1
    XbaI                                                                StyI
5'-CTAGAATAACTAACTAAAGGAGAACAACAACCATGTCTCATGGTTCCGCTCAGGTTAAAGGT-3'
    3'-TTATTGATTGATTTCCTCTTGTTGTTGGTACAGAGTACCAAGGCGAGTCCAATTTCCAGTAC-5'
                                     TA2
    XhoI
5'-TCGAGCGCATGTTCCTGTCTTTCCCGACTACTAAAACGTACTTCCCGCATTTCGACCTGGGTTCTGGTGGTT-
    3'-CGCGTACAAGGACAGAAAGGGCTGATGATTTTGCATGAAGGGCGTAAAGCTGGACCCAAGACCACCAA-

StyI    PstI
  -CTCATGGATCCGCTCAGGTTAAAGGCCATGGCTGCA-3'
  -GAGTACCTAGGCGAGTCCAATTTCCGGTACCG-5'
```

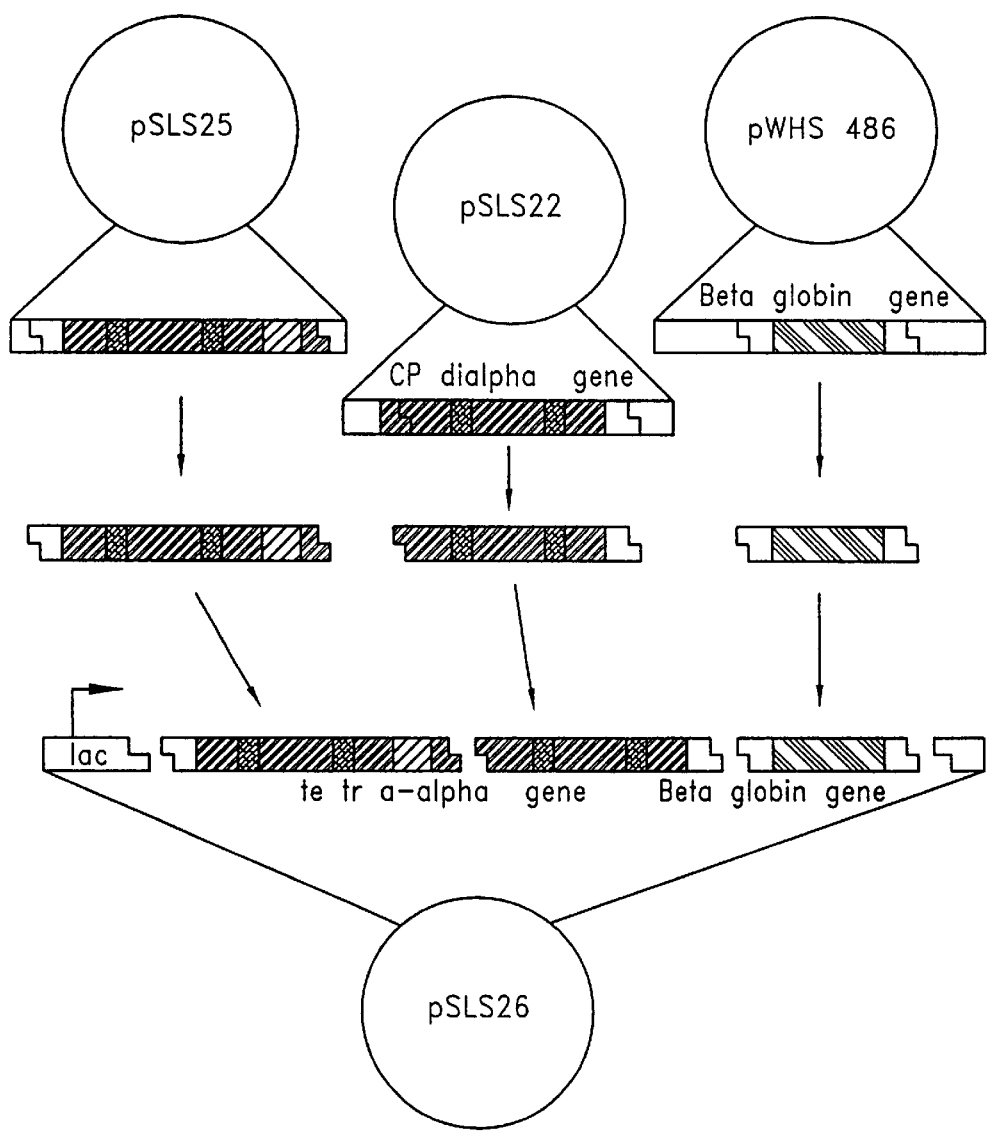

Figure 13

Circularly Permuted Tetra-alpha Gene Sequence

```
XbaI                                        1/37  BamHI
TCT AGA ATA ACT AAC TAA AGG AGA ACA ACA ACC ATG TCT CAT GGT TCC GCT CAG GTT AAG
AGA TCT TAT TGA TTG ATT TCC TCT TGT TGT TGG TAC AGA GTA CCA AGG CGA GTC CAA TTC
                                            met ser his gly ser ala gln val lys StyI                                     20/94
GGT CAT GGT AAA AAA GTT GCT GAC GCG TTG ACT AAC GCT GTT GCT CAT GTT GAC GAC ATG
CCG GTA CCA TTT TTT CAA CGA CTG CGC AAC TGA TTG CGA CAA CGA GTA CAA CTG CTG TAC
gly his gly lys lys val ala asp ala leu thr asn ala val ala his val asp asp met 30/124                                40/154
CCG AAC GCT CTG TCC GCT CTG TCA GAT CTT CAT GCT CAT AAA CTG CGC GTT GAC CCG GTA
GGC TTG CGA GAC AGG CGA GAC AGT CTA GAA GTA CGA GTA TTT GAC GCG CAA CTG GGC CAT
pro asn ala leu ser ala leu ser asp leu his ala his lys leu arg val asp pro val 50/184                                60/214
AAC TTC AAG CTT CTG TCT CAT TGC CTG CTG GTT ACT CTG GCT GCT CAT CTG CCG GCA GAA
TTG AAG TTC GAA GAC AGA GTA ACG GAC GAC CAA TGA GAC CGA CGA GTA GAC GGC CGT CTT
asn phe lys leu leu ser his cys leu leu val thr leu ala ala his leu pro ala glu 70/244                                80/274
TTC ACT CCG GCT GTT CAT GCT TCT CTG GAT AAA TTC CTG GCT TCT GTG TCG ACT GTT CTG
AAG TGA GGC CGA CAA GTA CGA AGA GAC CTA TTT AAG GAC CGA AGA CAC AGC TGA CAA GAC
phe thr pro ala val his ala ser leu asp lys phe leu ala ser val ser thr val leu 90/304                                100/334
ACT TCT AAA TAC CGC GGT GTT CTG TCT CCG GCA GAC AAA ACT AAC GTT AAA GCT GCT TGG
TGA AGA TTT ATG GCG CCA CAA GAC AGA GGC CGT CTG TTT TGA TTG CAA TTT CGA CGA ACC
thr ser lys tyr arg gly val leu ser pro ala asp lys thr asn val lys ala ala trp 110/364                               120/394
GGT AAA GTT GGA GCT CAT GCT GGT GAA TAC GGT GCT GAA GCA CTC GAG CGT ATG TTC CTG
CCA TTT CAA CCT CGA GTA CGA CCA CTT ATG CCA CGA CTT CGT GAG CTC GCA TAC AAG GAC
gly lys val gly ala his ala gly glu tyr gly ala glu ala leu glu arg met phe leu 130/424                               140/454          BamHI
TCT TTC CCG ACT ACT AAA ACG TAC TTC CCG CAT TTC GAC CTG TCT CAT GGA TCC GCT CAG
AGA AAG GGC TGA TGA TTT TGC ATG AAG GGC GTA AAG CTG GAC AGA GTA CCT AGG CGA GTC
ser phe pro thr thr lys thr tyr phe pro his phe asp leu ser his gly ser ala gln 150/484                               160/514
GTT AAA GGT CAT GGT AAA AAA GTT GCT GAC GCG TTG ACT AAC GCT GTT GCT CAT GTT GAC
CAA TTT CCA GTA CCA TTT TTT CAA CGA CTG CGC AAC TGA TTG CGA CAA CGA GTA CAA CTG
val lys gly his gly lys lys val ala asp ala leu thr asn ala val ala his val asp 170/544                               180/574
GAC ATG CCG AAC GCT CTG TCC GCT CTG TCA GAT CTT CAT GCT CAT AAA CTG CGC GTT GAC
CTG TAC GGC TTG CGA GAC AGG CGA GAC AGT CTA GAA GTA CGA GTA TTT GAC GCG CAA CTG
asp met pro asn ala leu ser ala leu ser asp leu his ala his lys leu arg val asp 190/604                               200/634
CCG GTA AAC TTC AAG CTT CTG TCT CAT TGC CTG CTG GTT ACT CTG GCT GCT CAT CTG CCG
GGC CAT TTG AAG TTC GAA GAC AGA GTA ACG GAC GAC CAA TGA GAC CGA CGA GTA GAC GGC
pro val asn phe lys leu leu ser his cys leu leu val thr leu ala ala his leu pro 210/664                               220/694
GCA GAA TTC ACT CCG GCT GTT CAT GCT TCT CTG GAT AAA TTC CTG GCT TCT GTG TCG ACT
CGT CTT AAG TGA GGC CGA CAA GTA CGA AGA GAC CTA TTT AAG GAC CGA AGA CAC AGC TGA
ala glu phe thr pro ala val his ala ser leu asp lys phe leu ala ser val ser thr
```

Figure 13 (cont.)

```
       230/724                                        240/754
GTT CTG ACT TCT AAA TAC CGC GGT GTT CTG TCT CCG GCA GAC AAA ACT AAC GTT AAA GCT
CAA GAC TGA AGA TTT ATG GCG CCA CAA GAC AGA GGC CGT CTG TTT TGA TTG CAA TTT CGA
val leu thr ser lys tyr arg gly val leu ser pro ala asp lys thr asn val lys ala 250/784                                        260/814              XhoI
GCT TGG GGT AAA GTT GGA GCT CAT GCT GGT GAA TAC GGT GCT GAA GCA CTC GAG CGT ATG
CGA ACC CCA TTT CAA CCT CGA GTA CGA CCA CTT ATG CCA CGA CTT CGT GAG CTC GCA TAC
ala trp gly lys val gly ala his ala gly glu tyr gly ala glu ala leu glu arg met 270/844                                        280/874
TTC CTG TCT TTC CCG ACT ACT AAA ACG TAC TTC CCG CAT TTC GAC CTG GGT TCT GGT GGT
AAG GAC AGA AAG GGC TGA TGA TTT TGC ATG AAG GGC GTA AAG CTG GAC CCA AGA CCA CCA
phe leu ser phe pro thr thr lys thr tyr phe pro his phe asp leu gly ser gly gly 280/904                             StyI       290/934
TCT CAT GGT TCC GCT CAG GTT AAG GGC CAT GGT AAA AAA GTT GCT GAC GCG TTG ACT AAC
AGA GTA CCA AGG CGA GTC CAA TTC CCG GTA CCA TTT TTT CAA CGA CTG CGC AAC TGA TTG
ser his gly ser ala gln val lys gly his gly lys lys val ala asp ala leu thr asn 300/964                                        310/994
GCT GTT GCT CAT GTT GAC GAC ATG CCG AAC GCT CTG TCC GCT CTG TCA GAT CTT CAT GCT
CGA CAA CGA GTA CAA CTG CTG TAC GGC TTG CGA GAC AGG CGA GAC AGT CTA GAA GTA CGA
ala val ala his val asp asp met pro asn ala leu ser ala leu ser asp leu his ala 320/1024                                       330/1054
CAT AAA CTG CGC GTT GAC CCG GTA AAC TTC AAG CTT CTG TCT CAT TGC CTG CTG GTT ACT
GTA TTT GAC GCG CAA CTG GGC CAT TTG AAG TTC GAA GAC AGA GTA ACG GAC GAC CAA TGA
his lys leu arg val asp pro val asn phe lys leu leu ser his cys leu leu val thr 340/1084                                       350/1114
CTG GCT GCT CAT CTG CCG GCA GAA TTC ACT CCG GCT GTT CAT GCT TCT CTG GAT AAA TTC
GAC CGA CGA GTA GAC GGC CGT CTT AAG TGA GGC CGA CAA GTA CGA AGA GAC CTA TTT AAG
leu ala ala his leu pro ala glu phe thr pro ala val his ala ser leu asp lys phe 360/1044                                       370/1174
CTG GCT TCT GTG TCG ACT GTT CTG ACT TCT AAA TAC CGC GGT GTT CTG TCT CCG GCA GAC
GAC CGA AGA CAC AGC TGA CAA GAC TGA AGA TTT ATG GCG CCA CAA GAC AGA GGC CGT CTG
leu ala ser val ser thr val leu thr ser lys tyr arg gly val leu ser pro ala asp 380/1204                                       390/1234
AAA ACT AAC GTT AAA GCT GCT TGG GGT AAA GTT GGA GCT CAT GCT GGT GAA TAC GGT GCT
TTT TGA TTG CAA TTT CGA CGA ACC CCA TTT CAA CCT CGA GTA CGA CCA CTT ATG CCA CGA
lys thr asn val lys ala ala trp gly lys val gly ala his ala gly glu tyr gly ala 400/1264                                       410/1294
GAA GCA CTC GAG CGT ATG TTC CTG TCT TTC CCG ACT ACT AAA ACG TAC TTC CCG CAT TTC
CTT CGT GAG CTC GCA TAC AAG GAC AGA AAG GGC TGA TGA TTT TGC ATG AAG GGC GTA AAG
glu ala leu glu arg met phe leu ser phe pro thr thr lys thr tyr phe pro his phe 420/1324                                       430/1354
GAC CTG TCT CAT GGA TCC GCT CAG GTT AAA GGT CAT GGT AAA AAA GTT GCT GAC GCG TTG
CTG GAC AGA GTA CCT AGG CGA GTC CAA TTT CCA GTA CCA TTT TTT CAA CGA CTG CGC AAC
asp leu ser his gly ser ala gln val lys gly his gly lys lys val ala asp ala leu
```

Figure 13 (cont.)

```
     440/1384                                    450/1414
ACT AAC GCT GTT GCT CAT GTT GAC GAC ATG CCG AAC GCT CTG TCC GCT CTG TCA GAT CTT
TGA TTG CGA CAA CGA GTA CAA CTG CTG TAC GGC TTG CGA GAC AGG CGA GAC AGT CTA GAA
thr asn ala val ala his val asp asp met pro asn ala leu ser ala leu ser asp leu 460/1444                                    470/1474
CAT GCT CAT AAA CTG CGC GTT GAC CCG GTA AAC TTC AAG CTT CTG TCT CAT TGC CTG CTG
GTA CGA GTA TTT GAC GCG CAA CTG GGC CAT TTG AAG TTC GAA GAC AGA GTA ACG GAC GAC
his ala his lys leu arg val asp pro val asn phe lys leu leu ser his cys leu leu 480/1504                                    490/1534
GTT ACT CTG GCT GCT CAT CTG CCG GCA GAA TTC ACT CCG GCT GTT CAT GCT TCT CTG GAT
CAA TGA GAC CGA CGA GTA GAC GGC CGT CTT AAG TGA GGC CGA CAA GTA CGA AGA GAC CTA
val thr leu ala ala his leu pro ala glu phe thr pro ala val his ala ser leu asp 500/1564                                    510/1594
AAA TTC CTG GCT TCT GTG TCG ACT GTT CTG ACT TCT AAA TAC CGC GGT GTT CTG TCT CCG
TTT AAG GAC CGA AGA CAC AGC TGA CAA GAC TGA AGA TTT ATG GCG CCA CAA GAC AGA GGC
lys phe leu ala ser val ser thr val leu thr ser lys tyr arg gly val leu ser pro 520/1624                                    530/1654
GCA GAC AAA ACT AAC GTT AAA GCT GCT TGG GGT AAA GTT GGA GCT CAT GCT GGT GAA TAC
CGT CTG TTT TGA TTG CAA TTT CGA CGA ACC CCA TTT CAA CCT CGA GTA CGA CCA CTT ATG
ala asp lys thr asn val lys ala ala trp gly lys val gly ala his ala gly glu tyr 540/1584                                    550/1614
GGT GCT GAA GCA CTC GAG CGT ATG TTC CTG TCT TTC CCG ACT ACT AAA ACG TAC TTC CCG
CCA CGA CTT CGT GAG CTC GCA TAC AAG GAC AGA AAG GGC TGA TGA TTT TGC ATG AAG GGC
gly ala glu ala leu glu arg met phe leu ser phe pro thr thr lys thr tyr phe pro 560/1644           PstI
CAT TTC GAC CTG TAA TGA CTG CAG
GTA AAG CTG GAC ATT ACT GAC GTC
his phe asp leu OCH OPA
```

Figure 16

Figure Legends:

All plasmids represented in figures 1,5,6,8,10,11,12,13, and 14 are pUC based plasmids containing the ampicillin resistance gene and the colE1 origin. The genes cloned into the vectors are under the control of the *lac* promoter. The following is a legend for the plasmid schematics:

 alpha-globin or alpha -globin like gene or gene fragment

 beta-globin gene

 non amino acid coding DNA sequence

 Restriction enzyme site

 Glycine codon used to link 2 alpha-globin genes

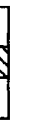 DNA coding Gly-Ser-Gly-Gly used to link 2 Circularly permuted di-alpha genes

SEQUENCE LISTING

```
<160> NUMBER OF SEQ ID NOS: 19

<210> SEQ ID NO 1
<211> LENGTH: 79
<212> TYPE: DNA
<213> ORGANISM: Artificial Sequence
<220> FEATURE:
<223> OTHER INFORMATION: Description of Artificial Sequence: Cassette

<400> SEQUENCE: 1
gacaagactg aagatttatg gcgccacaag acagaggccg tctgttttga ttgcaatttc    60
gacgaacccc atttcaacc                                                 79

<210> SEQ ID NO 2
<211> LENGTH: 87
<212> TYPE: DNA
<213> ORGANISM: Artificial Sequence
<220> FEATURE:
<223> OTHER INFORMATION: Description of Artificial Sequence: Cassette

<400> SEQUENCE: 2
tcgactgttc tgacttctaa ataccgcggt gttctgtctc cggcagacaa aactaacgtt    60
aaagctgctt ggggtaaagt tggagct                                        87

<210> SEQ ID NO 3
<211> LENGTH: 894
<212> TYPE: DNA
<213> ORGANISM: Homo sapiens
<220> FEATURE:
<221> NAME/KEY: CDS
<222> LOCATION: (34)..(882)

<400> SEQUENCE: 3
tctagaataa ctaactaaag gagaacaaca acc atg ctg tct ccg gca gac aaa    54
                                    Met Leu Ser Pro Ala Asp Lys
                                    1               5
```

```
act aac gtt aaa gct gct tgg ggt aaa gtt gga gct cat gct ggt gaa      102
Thr Asn Val Lys Ala Ala Trp Gly Lys Val Gly Ala His Ala Gly Glu
         10                  15                  20 tac ggt gct gaa gca ctc gag cgt atg ttc ctg tct ttc ccg act act      150
Tyr Gly Ala Glu Ala Leu Glu Arg Met Phe Leu Ser Phe Pro Thr Thr
 25                  30                  35 aaa acg tac ttc ccg cat ttc gac ctg tct cat gga tcc gct cag gtt      198
Lys Thr Tyr Phe Pro His Phe Asp Leu Ser His Gly Ser Ala Gln Val
 40                  45                  50                  55 aaa ggt cat ggt aaa aaa gtt gct gac gcg ttg act aac gct gtt gct      246
Lys Gly His Gly Lys Lys Val Ala Asp Ala Leu Thr Asn Ala Val Ala
             60                  65                  70 cat gtt gac gac atg ccg aac gct ctg tcc gct ctg tca gat ctt cat      294
His Val Asp Asp Met Pro Asn Ala Leu Ser Ala Leu Ser Asp Leu His
         75                  80                  85 gct cat aaa ctg cgc gtt gac ccg gta aac ttc aag ctt ctg tct cat      342
Ala His Lys Leu Arg Val Asp Pro Val Asn Phe Lys Leu Leu Ser His
     90                  95                 100 tgc ctg ctg gtt act ctg gct gct cat ctg ccg gca gaa ttc act ccg      390
Cys Leu Leu Val Thr Leu Ala Ala His Leu Pro Ala Glu Phe Thr Pro
105                 110                 115 gct gtt cat gct tct ctg gat aaa ttc ctg gct tct gtg tcg act gtt      438
Ala Val His Ala Ser Leu Asp Lys Phe Leu Ala Ser Val Ser Thr Val
120                 125                 130                 135 ctg act tct aaa tac cgc ggt gtt ctg tct ccg gca gac aaa act aac      486
Leu Thr Ser Lys Tyr Arg Gly Val Leu Ser Pro Ala Asp Lys Thr Asn
             140                 145                 150 gtt aaa gct gct tgg ggt aaa gtt gga gct cat gct ggt gaa tac ggt      534
Val Lys Ala Ala Trp Gly Lys Val Gly Ala His Ala Gly Glu Tyr Gly
                 155                 160                 165 gct gaa gca ctc gag cgt atg ttc ctg tct ttc ccg act act aaa acg      582
Ala Glu Ala Leu Glu Arg Met Phe Leu Ser Phe Pro Thr Thr Lys Thr
             170                 175                 180 tac ttc ccg cat ttc gac ctg tct cat gga tcc gct cag gtt aaa ggt      630
Tyr Phe Pro His Phe Asp Leu Ser His Gly Ser Ala Gln Val Lys Gly
         185                 190                 195 cat ggt aaa aaa gtt gct gac gcg ttg act aac gct gtt gct cat gtt      678
His Gly Lys Lys Val Ala Asp Ala Leu Thr Asn Ala Val Ala His Val
200                 205                 210                 215 gac gac atg ccg aac gct ctg tcc gct ctg tca gat ctt cat gct cat      726
Asp Asp Met Pro Asn Ala Leu Ser Ala Leu Ser Asp Leu His Ala His
             220                 225                 230 aaa ctg cgc gtt gac ccg gta aac ttc aag ctt ctg tct cat tgc ctg      774
Lys Leu Arg Val Asp Pro Val Asn Phe Lys Leu Leu Ser His Cys Leu
         235                 240                 245 ctg gtt act ctg gct gct cat ctg ccg gca gaa ttc act ccg gct gtt      822
Leu Val Thr Leu Ala Ala His Leu Pro Ala Glu Phe Thr Pro Ala Val
     250                 255                 260 cat gct tct ctg gat aaa ttc ctg gct tct gtg tcg act gtt ctg act      870
His Ala Ser Leu Asp Lys Phe Leu Ala Ser Val Ser Thr Val Leu Thr
 265                 270                 275 tct aaa tac cgt taatgactgc ag                                        894
Ser Lys Tyr Arg
280
```

<210> SEQ ID NO 4
<211> LENGTH: 283
<212> TYPE: PRT
<213> ORGANISM: Homo sapiens

<400> SEQUENCE: 4

```
Met Leu Ser Pro Ala Asp Lys Thr Asn Val Lys Ala Ala Trp Gly Lys
1               5                  10                  15
Val Gly Ala His Ala Gly Glu Tyr Gly Ala Glu Ala Leu Glu Arg Met
            20                  25                  30
Phe Leu Ser Phe Pro Thr Thr Lys Thr Tyr Phe Pro His Phe Asp Leu
        35                  40                  45
Ser His Gly Ser Ala Gln Val Lys Gly His Gly Lys Lys Val Ala Asp
    50                  55                  60
Ala Leu Thr Asn Ala Val Ala His Val Asp Asp Met Pro Asn Ala Leu
65                  70                  75                  80
Ser Ala Leu Ser Asp Leu His Ala His Lys Leu Arg Val Asp Pro Val
                85                  90                  95
Asn Phe Lys Leu Leu Ser His Cys Leu Leu Val Thr Leu Ala Ala His
            100                 105                 110
Leu Pro Ala Glu Phe Thr Pro Ala Val His Ala Ser Leu Asp Lys Phe
        115                 120                 125
Leu Ala Ser Val Ser Thr Val Leu Thr Ser Lys Tyr Arg Gly Val Leu
    130                 135                 140
Ser Pro Ala Asp Lys Thr Asn Val Lys Ala Ala Trp Gly Lys Val Gly
145                 150                 155                 160
Ala His Ala Gly Glu Tyr Gly Ala Glu Ala Leu Glu Arg Met Phe Leu
                165                 170                 175
Ser Phe Pro Thr Thr Lys Thr Tyr Phe Pro His Phe Asp Leu Ser His
            180                 185                 190
Gly Ser Ala Gln Val Lys Gly His Gly Lys Lys Val Ala Asp Ala Leu
        195                 200                 205
Thr Asn Ala Val Ala His Val Asp Asp Met Pro Asn Ala Leu Ser Ala
    210                 215                 220
Leu Ser Asp Leu His Ala His Lys Leu Arg Val Asp Pro Val Asn Phe
225                 230                 235                 240
Lys Leu Leu Ser His Cys Leu Leu Val Thr Leu Ala Ala His Leu Pro
                245                 250                 255
Ala Glu Phe Thr Pro Ala Val His Ala Ser Leu Asp Lys Phe Leu Ala
            260                 265                 270
Ser Val Ser Thr Val Leu Thr Ser Lys Tyr Arg
        275                 280
```

<210> SEQ ID NO 5
<211> LENGTH: 894
<212> TYPE: DNA
<213> ORGANISM: Homo sapiens

<400> SEQUENCE: 5

```
agatcttatt gattgatttc ctcttgttgt tggtacgaca gaggccgtct gttttgattg      60
caatttcgac gaaccccatt tcaacctcga gtacgaccac ttatgccacg acttcgtgag     120
ctcgcataca aggacagaaa gggctgatga ttttgcatga agggcgtaaa gctggacaga     180
gtacctaggc gagtccaatt tccagtacca ttttttcaac gactgcgcaa ctgattgcga     240
caacgagtac aactgctgta cggcttgcga gacaggcgag acagtctaga agtacgagta     300
tttgacgcgc aactgggcca tttgaagttc gaagacagag taacggacga ccaatgagac     360
cgacgagtag acggccgtct taagtgaggc cgacaagtac gaagagacct atttaaggac     420
cgaagacaca gctgacaaga ctgaagattt atggcgccac aagacagagg ccgtctgttt     480
```

```
tgattgcaat ttcgacgaac cccatttcaa cctcgagtac gaccacttat gccacgactt    540
cgtgagctcg catacaagga cagaaagggc tgatgatttt gcatgaaggg cgtaaagctg    600
gacagagtac ctaggcgagt ccaatttcca gtaccatttt ttcaacgact gcgcaactga    660
ttgcgacaac gagtacaact gctgtacggc ttgcgagaca ggcgagacag tctagaagta    720
cgagtatttg acgcgcaact gggccatttg aagttcgaag acagagtaac ggacgaccaa    780
tgagaccgac gagtagacgg ccgtcttaag tgaggccgac aagtacgaag agacctattt    840
aaggaccgaa gacacagctg acaagactga agatttatgg caattactga cgtc          894

<210> SEQ ID NO 6
<211> LENGTH: 82
<212> TYPE: DNA
<213> ORGANISM: Artificial Sequence
<220> FEATURE:
<223> OTHER INFORMATION: Description of Artificial Sequence: Cassette

<400> SEQUENCE: 6
ctagaataac taactaaagg agaacaacaa ccatgtctca tggttccgct caggttaagg    60
gccatggtaa aaaagttgct ga                                             82

<210> SEQ ID NO 7
<211> LENGTH: 82
<212> TYPE: DNA
<213> ORGANISM: Artificial Sequence
<220> FEATURE:
<223> OTHER INFORMATION: Description of Artificial Sequence: Cassette

<400> SEQUENCE: 7
ttattgattg atttcctctt gttgttggta cagagtacca aggcgagtcc aattcccggt    60
accatttttt caacgactgc gc                                             82

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence: Cassette

<400> SEQUENCE: 8
tcgagcgcat gttcctgtct ttcccgacta ctaaaacgta cttcccgcat ttcgacctgt    60
aatgactgca                                                           70

<210> SEQ ID NO 9
<211> LENGTH: 61
<212> TYPE: DNA
<213> ORGANISM: Artificial Sequence
<220> FEATURE:
<223> OTHER INFORMATION: Description of Artificial Sequence: Cassette

<400> SEQUENCE: 9
gcgtacaagg acagaaaggg ctgatgattt tgcatgaagg gcgtaaagct ggacattact    60
g                                                                    61

<210> SEQ ID NO 10
<211> LENGTH: 900
<212> TYPE: DNA
<213> ORGANISM: Homo sapiens
<220> FEATURE:
<221> NAME/KEY: CDS
<222> LOCATION: (34)..(888)
```

-continued

```
<400> SEQUENCE: 10
tctagaataa ctaactaaag gagaacaaca acc atg tct cat ggt tcc gct cag          54
                                    Met Ser His Gly Ser Ala Gln
                                      1               5 gtt aag ggc cat ggt aaa aaa gtt gct gac gcg ttg act aac gct gtt         102
Val Lys Gly His Gly Lys Lys Val Ala Asp Ala Leu Thr Asn Ala Val
         10                  15                  20 gct cat gtt gac gac atg ccg aac gct ctg tcc gct ctg tca gat ctt         150
Ala His Val Asp Asp Met Pro Asn Ala Leu Ser Ala Leu Ser Asp Leu
     25                  30                  35 cat gct cat aaa ctg cgc gtt gac ccg gta aac ttc aag ctt ctg tct         198
His Ala His Lys Leu Arg Val Asp Pro Val Asn Phe Lys Leu Leu Ser
 40                  45                  50                  55 cat tgc ctg ctg gtt act ctg gct gct cat ctg ccg gca gaa ttc act         246
His Cys Leu Leu Val Thr Leu Ala Ala His Leu Pro Ala Glu Phe Thr
                 60                  65                  70 ccg gct gtt cat gct tct ctg gat aaa ttc ctg gct tct gtg tcg act         294
Pro Ala Val His Ala Ser Leu Asp Lys Phe Leu Ala Ser Val Ser Thr
             75                  80                  85 gtt ctg act tct aaa tac cgc ggt gtt ctg tct ccg gca gac aaa act         342
Val Leu Thr Ser Lys Tyr Arg Gly Val Leu Ser Pro Ala Asp Lys Thr
         90                  95                 100 aac gtt aaa gct gct tgg ggt aaa gtt gga gct cat gct ggt gaa tac         390
Asn Val Lys Ala Ala Trp Gly Lys Val Gly Ala His Ala Gly Glu Tyr
    105                 110                 115 ggt gct gaa gca ctc gag cgt atg ttc ctg tct ttc ccg act act aaa         438
Gly Ala Glu Ala Leu Glu Arg Met Phe Leu Ser Phe Pro Thr Thr Lys
120                 125                 130                 135 acg tac ttc ccg cat ttc gac ctg tct cat gga tcc gct cag gtt aaa         486
Thr Tyr Phe Pro His Phe Asp Leu Ser His Gly Ser Ala Gln Val Lys
                140                 145                 150 ggt cat ggt aaa aaa gtt gct gac gcg ttg act aac gct gtt gct cat         534
Gly His Gly Lys Lys Val Ala Asp Ala Leu Thr Asn Ala Val Ala His
            155                 160                 165 gtt gac gac atg ccg aac gct ctg tcc gct ctg tca gat ctt cat gct         582
Val Asp Asp Met Pro Asn Ala Leu Ser Ala Leu Ser Asp Leu His Ala
        170                 175                 180 cat aaa ctg cgc gtt gac ccg gta aac ttc aag ctt ctg tct cat tgc         630
His Lys Leu Arg Val Asp Pro Val Asn Phe Lys Leu Leu Ser His Cys
    185                 190                 195 ctg ctg gtt act ctg gct gct cat ctg ccg gca gaa ttc act ccg gct         678
Leu Leu Val Thr Leu Ala Ala His Leu Pro Ala Glu Phe Thr Pro Ala
200                 205                 210                 215 gtt cat gct tct ctg gat aaa ttc ctg gct tct gtg tcg act gtt ctg         726
Val His Ala Ser Leu Asp Lys Phe Leu Ala Ser Val Ser Thr Val Leu
                220                 225                 230 act tct aaa tac cgc ggt gtt ctg tct ccg gca gac aaa act aac gtt         774
Thr Ser Lys Tyr Arg Gly Val Leu Ser Pro Ala Asp Lys Thr Asn Val
            235                 240                 245 aaa gct gct tgg ggt aaa gtt gga gct cat gct ggt gaa tac ggt gct         822
Lys Ala Ala Trp Gly Lys Val Gly Ala His Ala Gly Glu Tyr Gly Ala
        250                 255                 260 gaa gca ctc gag cgt atg ttc ctg tct ttc ccg act act aaa acg tac         870
Glu Ala Leu Glu Arg Met Phe Leu Ser Phe Pro Thr Thr Lys Thr Tyr
    265                 270                 275 ttc ccg cat ttc gac ctg taatgactgc ag                                   900
Phe Pro His Phe Asp Leu
280                 285
```

<210> SEQ ID NO 11
<211> LENGTH: 285
<212> TYPE: PRT
<213> ORGANISM: Homo sapiens

<400> SEQUENCE: 11

Met Ser His Gly Ser Ala Gln Val Lys Gly His Gly Lys Lys Val Ala
 1               5                  10                  15

Asp Ala Leu Thr Asn Ala Val Ala His Val Asp Asp Met Pro Asn Ala
            20                  25                  30

Leu Ser Ala Leu Ser Asp Leu His Ala His Lys Leu Arg Val Asp Pro
        35                  40                  45

Val Asn Phe Lys Leu Leu Ser His Cys Leu Leu Val Thr Leu Ala Ala
    50                  55                  60

His Leu Pro Ala Glu Phe Thr Pro Ala Val His Ala Ser Leu Asp Lys
65                  70                  75                  80

Phe Leu Ala Ser Val Ser Thr Val Leu Thr Ser Lys Tyr Arg Gly Val
                85                  90                  95

Leu Ser Pro Ala Asp Lys Thr Asn Val Lys Ala Ala Trp Gly Lys Val
            100                 105                 110

Gly Ala His Ala Gly Glu Tyr Gly Ala Glu Ala Leu Glu Arg Met Phe
        115                 120                 125

Leu Ser Phe Pro Thr Thr Lys Thr Tyr Phe Pro His Phe Asp Leu Ser
    130                 135                 140

His Gly Ser Ala Gln Val Lys Gly His Gly Lys Lys Val Ala Asp Ala
145                 150                 155                 160

Leu Thr Asn Ala Val Ala His Val Asp Asp Met Pro Asn Ala Leu Ser
                165                 170                 175

Ala Leu Ser Asp Leu His Ala His Lys Leu Arg Val Asp Pro Val Asn
            180                 185                 190

Phe Lys Leu Leu Ser His Cys Leu Leu Val Thr Leu Ala Ala His Leu
        195                 200                 205

Pro Ala Glu Phe Thr Pro Ala Val His Ala Ser Leu Asp Lys Phe Leu
    210                 215                 220

Ala Ser Val Ser Thr Val Leu Thr Ser Lys Tyr Arg Gly Val Leu Ser
225                 230                 235                 240

Pro Ala Asp Lys Thr Asn Val Lys Ala Ala Trp Gly Lys Val Gly Ala
                245                 250                 255

His Ala Gly Glu Tyr Gly Ala Glu Ala Leu Glu Arg Met Phe Leu Ser
            260                 265                 270

Phe Pro Thr Thr Lys Thr Tyr Phe Pro His Phe Asp Leu
        275                 280                 285

<210> SEQ ID NO 12
<211> LENGTH: 900
<212> TYPE: DNA
<213> ORGANISM: Homo sapiens

<400> SEQUENCE: 12
agatcttatt gattgatttc ctcttgttgt tggtacagag taccaaggcg agtccaattc      60
ccggtaccat tttttcaacg actgcgcaac tgattgcgac aacgagtaca actgctgtac     120
ggcttgcgag acaggcgaga cagtctagaa gtacgagtat ttgacgcgca actgggccat     180
ttgaagttcg aagacagagt aacggacgac caatgagacc gacgagtaga cggccgtctt     240
aagtgaggcc gacaagtacg aagagaccta tttaaggacc gaagacacag ctgacaagac     300

```
tgaagattta tggcgccaca agacagaggc cgtctgtttt gattgcaatt tcgacgaacc      360
ccatttcaac ctcgagtacg accacttatg ccacgacttc gtgagctcgc atacaaggac      420
agaaagggct gatgattttg catgaaggc gtaaagctgg acagagtacc taggcgagtc       480
caatttccag taccattttt tcaacgactg cgcaactgat tgcgacaacg agtacaactg      540
ctgtacggct tgcgagacag gcgagacagt ctagaagtac gagtatttga cgcgcaactg      600
ggccatttga agttcgaaga cagagtaacg gacgaccaat gagaccgacg agtagacggc      660
cgtcttaagt gaggccgaca agtacgaaga gacctatttta aggaccgaag acacagctga     720
caagactgaa gatttatggc gccacaagac agaggccgtc tgttttgatt gcaatttcga      780 cgaacccat ttcaacctcg agtacgacca cttatgccac gacttcgtga gctcgcatac       840
aaggacagaa agggctgatg attttgcatg aagggcgtaa agctggacat tactgacgtc      900

<210> SEQ ID NO 13
<211> LENGTH: 62
<212> TYPE: DNA
<213> ORGANISM: Artificial Sequence
<220> FEATURE:
<223> OTHER INFORMATION: Description of Artificial Sequence: Cassette

<400> SEQUENCE: 13
ctagaataac taactaaagg agaacaacaa ccatgtctca tggttccgct caggttaaag      60
gt                                                                     62

<210> SEQ ID NO 14
<211> LENGTH: 62
<212> TYPE: DNA
<213> ORGANISM: Artificial Sequence
<220> FEATURE:
<223> OTHER INFORMATION: Description of Artificial Sequence: Cassette

<400> SEQUENCE: 14
ttattgattg atttcctctt gttgttggta cagagtacca aggcgagtcc aatttccagt      60
ac                                                                     62

<210> SEQ ID NO 15
<211> LENGTH: 108
<212> TYPE: DNA
<213> ORGANISM: Artificial Sequence
<220> FEATURE:
<223> OTHER INFORMATION: Description of Artificial Sequence: Cassette

<400> SEQUENCE: 15
tcgagcgcat gttcctgtct ttcccgacta ctaaaacgta cttcccgcat ttcgacctgg      60
gttctggtgg ttctcatgga tccgctcagg ttaaaggcca tggctgca                  108

<210> SEQ ID NO 16
<211> LENGTH: 100
<212> TYPE: DNA
<213> ORGANISM: Artificial Sequence
<220> FEATURE:
<223> OTHER INFORMATION: Description of Artificial Sequence: Cassette

<400> SEQUENCE: 16
cgcgtacaag gacagaaagg gctgatgatt ttgcatgaag gcgtaaagc tggacccaag       60 accaccaaga gtacctaggc gagtccaatt tccggtaccg                           100

<210> SEQ ID NO 17
```

```
<211> LENGTH: 1764
<212> TYPE: DNA
<213> ORGANISM: Homo sapiens
<220> FEATURE:
<221> NAME/KEY: CDS
<222> LOCATION: (34)..(1752)

<400> SEQUENCE: 17
tctagaataa ctaactaaag gagaacaaca acc atg tct cat ggt tcc gct cag       54
                                    Met Ser His Gly Ser Ala Gln
                                    1               5 gtt aag ggt cat ggt aaa aaa gtt gct gac gcg ttg act aac gct gtt      102
Val Lys Gly His Gly Lys Lys Val Ala Asp Ala Leu Thr Asn Ala Val
        10                  15                  20 gct cat gtt gac gac atg ccg aac gct ctg tcc gct ctg tca gat ctt      150
Ala His Val Asp Asp Met Pro Asn Ala Leu Ser Ala Leu Ser Asp Leu
25                  30                  35 cat gct cat aaa ctg cgc gtt gac ccg gta aac ttc aag ctt ctg tct      198
His Ala His Lys Leu Arg Val Asp Pro Val Asn Phe Lys Leu Leu Ser
40                  45                  50                  55 cat tgc ctg ctg gtt act ctg gct gct cat ctg ccg gca gaa ttc act      246
His Cys Leu Leu Val Thr Leu Ala Ala His Leu Pro Ala Glu Phe Thr
            60                  65                  70 ccg gct gtt cat gct tct ctg gat aaa ttc ctg gct tct gtg tcg act      294
Pro Ala Val His Ala Ser Leu Asp Lys Phe Leu Ala Ser Val Ser Thr
                75                  80                  85 gtt ctg act tct aaa tac cgc ggt gtt ctg tct ccg gca gac aaa act      342
Val Leu Thr Ser Lys Tyr Arg Gly Val Leu Ser Pro Ala Asp Lys Thr
            90                  95                 100 aac gtt aaa gct gct tgg ggt aaa gtt gga gct cat gct ggt gaa tac      390
Asn Val Lys Ala Ala Trp Gly Lys Val Gly Ala His Ala Gly Glu Tyr
        105                 110                 115 ggt gct gaa gca ctc gag cgt atg ttc ctg tct ttc ccg act act aaa      438
Gly Ala Glu Ala Leu Glu Arg Met Phe Leu Ser Phe Pro Thr Thr Lys
120                 125                 130                 135 acg tac ttc ccg cat ttc gac ctg tct cat gga tcc gct cag gtt aaa      486
Thr Tyr Phe Pro His Phe Asp Leu Ser His Gly Ser Ala Gln Val Lys
                140                 145                 150 ggt cat ggt aaa aaa gtt gct gac gcg ttg act aac gct gtt gct cat      534
Gly His Gly Lys Lys Val Ala Asp Ala Leu Thr Asn Ala Val Ala His
            155                 160                 165 gtt gac gac atg ccg aac gct ctg tcc gct ctg tca gat ctt cat gct      582
Val Asp Asp Met Pro Asn Ala Leu Ser Ala Leu Ser Asp Leu His Ala
        170                 175                 180 cat aaa ctg cgc gtt gac ccg gta aac ttc aag ctt ctg tct cat tgc      630
His Lys Leu Arg Val Asp Pro Val Asn Phe Lys Leu Leu Ser His Cys
    185                 190                 195 ctg ctg gtt act ctg gct gct cat ctg ccg gca gaa ttc act ccg gct      678
Leu Leu Val Thr Leu Ala Ala His Leu Pro Ala Glu Phe Thr Pro Ala
200                 205                 210                 215 gtt cat gct tct ctg gat aaa ttc ctg gct tct gtg tcg act gtt ctg      726
Val His Ala Ser Leu Asp Lys Phe Leu Ala Ser Val Ser Thr Val Leu
                220                 225                 230 act tct aaa tac cgc ggt gtt ctg tct ccg gca gac aaa act aac gtt      774
Thr Ser Lys Tyr Arg Gly Val Leu Ser Pro Ala Asp Lys Thr Asn Val
            235                 240                 245 aaa gct gct tgg ggt aaa gtt gga gct cat gct ggt gaa tac ggt gct      822
Lys Ala Ala Trp Gly Lys Val Gly Ala His Ala Gly Glu Tyr Gly Ala
        250                 255                 260 gaa gca ctc gag cgt atg ttc ctg tct ttc ccg act act aaa acg tac      870
Glu Ala Leu Glu Arg Met Phe Leu Ser Phe Pro Thr Thr Lys Thr Tyr
```

-continued

```
             265                 270                 275
ttc ccg cat ttc gac ctg ggt tct ggt ggt tct cat ggt tcc gct cag    918
Phe Pro His Phe Asp Leu Gly Ser Gly Gly Ser His Gly Ser Ala Gln
280             285                 290                 295 gtt aag ggc cat ggt aaa aaa gtt gct gac gcg ttg act aac gct gtt    966
Val Lys Gly His Gly Lys Lys Val Ala Asp Ala Leu Thr Asn Ala Val
                300                 305                 310 gct cat gtt gac gac atg ccg aac gct ctg tcc gct ctg tca gat ctt   1014
Ala His Val Asp Asp Met Pro Asn Ala Leu Ser Ala Leu Ser Asp Leu
            315                 320                 325 cat gct cat aaa ctg cgc gtt gac ccg gta aac ttc aag ctt ctg tct   1062
His Ala His Lys Leu Arg Val Asp Pro Val Asn Phe Lys Leu Leu Ser
        330                 335                 340 cat tgc ctg ctg gtt act ctg gct gct cat ctg ccg gca gaa ttc act   1110
His Cys Leu Leu Val Thr Leu Ala Ala His Leu Pro Ala Glu Phe Thr
    345                 350                 355 ccg gct gtt cat gct tct ctg gat aaa ttc ctg gct tct gtg tcg act   1158
Pro Ala Val His Ala Ser Leu Asp Lys Phe Leu Ala Ser Val Ser Thr
360                 365                 370                 375 gtt ctg act tct aaa tac cgc ggt gtt ctg tct ccg gca gac aaa act   1206
Val Leu Thr Ser Lys Tyr Arg Gly Val Leu Ser Pro Ala Asp Lys Thr
                380                 385                 390 aac gtt aaa gct gct tgg ggt aaa gtt gga gct cat gct ggt gaa tac   1254
Asn Val Lys Ala Ala Trp Gly Lys Val Gly Ala His Ala Gly Glu Tyr
            395                 400                 405 ggt gct gaa gca ctc gag cgt atg ttc ctg tct ttc ccg act act aaa   1302
Gly Ala Glu Ala Leu Glu Arg Met Phe Leu Ser Phe Pro Thr Thr Lys
        410                 415                 420 acg tac ttc ccg cat ttc gac ctg tct cat gga tcc gct cag gtt aaa   1350
Thr Tyr Phe Pro His Phe Asp Leu Ser His Gly Ser Ala Gln Val Lys
    425                 430                 435 ggt cat ggt aaa aaa gtt gct gac gcg ttg act aac gct gtt gct cat   1398
Gly His Gly Lys Lys Val Ala Asp Ala Leu Thr Asn Ala Val Ala His
440                 445                 450                 455 gtt gac gac atg ccg aac gct ctg tcc gct ctg tca gat ctt cat gct   1446
Val Asp Asp Met Pro Asn Ala Leu Ser Ala Leu Ser Asp Leu His Ala
                460                 465                 470 cat aaa ctg cgc gtt gac ccg gta aac ttc aag ctt ctg tct cat tgc   1494
His Lys Leu Arg Val Asp Pro Val Asn Phe Lys Leu Leu Ser His Cys
            475                 480                 485 ctg ctg gtt act ctg gct gct cat ctg ccg gca gaa ttc act ccg gct   1542
Leu Leu Val Thr Leu Ala Ala His Leu Pro Ala Glu Phe Thr Pro Ala
        490                 495                 500 gtt cat gct tct ctg gat aaa ttc ctg gct tct gtg tcg act gtt ctg   1590
Val His Ala Ser Leu Asp Lys Phe Leu Ala Ser Val Ser Thr Val Leu
    505                 510                 515 act tct aaa tac cgc ggt gtt ctg tct ccg gca gac aaa act aac gtt   1638
Thr Ser Lys Tyr Arg Gly Val Leu Ser Pro Ala Asp Lys Thr Asn Val
520                 525                 530                 535 aaa gct gct tgg ggt aaa gtt gga gct cat gct ggt gaa tac ggt gct   1686
Lys Ala Ala Trp Gly Lys Val Gly Ala His Ala Gly Glu Tyr Gly Ala
                540                 545                 550 gaa gca ctc gag cgt atg ttc ctg tct ttc ccg act act aaa acg tac   1734
Glu Ala Leu Glu Arg Met Phe Leu Ser Phe Pro Thr Thr Lys Thr Tyr
            555                 560                 565 ttc ccg cat ttc gac ctg taatgactgc ag                             1764
Phe Pro His Phe Asp Leu
        570
```

```
<210> SEQ ID NO 18
<211> LENGTH: 573
<212> TYPE: PRT
<213> ORGANISM: Homo sapiens

<400> SEQUENCE: 18

Met Ser His Gly Ser Ala Gln Val Lys Gly His Gly Lys Lys Val Ala
 1               5                  10                  15

Asp Ala Leu Thr Asn Ala Val Ala His Val Asp Asp Met Pro Asn Ala
            20                  25                  30

Leu Ser Ala Leu Ser Asp Leu His Ala His Lys Leu Arg Val Asp Pro
        35                  40                  45

Val Asn Phe Lys Leu Leu Ser His Cys Leu Leu Val Thr Leu Ala Ala
    50                  55                  60

His Leu Pro Ala Glu Phe Thr Pro Ala Val His Ala Ser Leu Asp Lys
 65                 70                  75                  80

Phe Leu Ala Ser Val Ser Thr Val Leu Thr Ser Lys Tyr Arg Gly Val
                85                  90                  95

Leu Ser Pro Ala Asp Lys Thr Asn Val Lys Ala Ala Trp Gly Lys Val
            100                 105                 110

Gly Ala His Ala Gly Glu Tyr Gly Ala Glu Ala Leu Glu Arg Met Phe
        115                 120                 125

Leu Ser Phe Pro Thr Thr Lys Thr Tyr Phe Pro His Phe Asp Leu Ser
    130                 135                 140

His Gly Ser Ala Gln Val Lys Gly His Gly Lys Lys Val Ala Asp Ala
145                 150                 155                 160

Leu Thr Asn Ala Val Ala His Val Asp Asp Met Pro Asn Ala Leu Ser
                165                 170                 175

Ala Leu Ser Asp Leu His Ala His Lys Leu Arg Val Asp Pro Val Asn
            180                 185                 190

Phe Lys Leu Leu Ser His Cys Leu Leu Val Thr Leu Ala Ala His Leu
        195                 200                 205

Pro Ala Glu Phe Thr Pro Ala Val His Ala Ser Leu Asp Lys Phe Leu
    210                 215                 220

Ala Ser Val Ser Thr Val Leu Thr Ser Lys Tyr Arg Gly Val Leu Ser
225                 230                 235                 240

Pro Ala Asp Lys Thr Asn Val Lys Ala Ala Trp Gly Lys Val Gly Ala
                245                 250                 255

His Ala Gly Glu Tyr Gly Ala Glu Ala Leu Glu Arg Met Phe Leu Ser
            260                 265                 270

Phe Pro Thr Thr Lys Thr Tyr Phe Pro His Phe Asp Leu Gly Ser Gly
        275                 280                 285

Gly Ser His Gly Ser Ala Gln Val Lys Gly His Gly Lys Lys Val Ala
    290                 295                 300

Asp Ala Leu Thr Asn Ala Val Ala His Val Asp Asp Met Pro Asn Ala
305                 310                 315                 320

Leu Ser Ala Leu Ser Asp Leu His Ala His Lys Leu Arg Val Asp Pro
                325                 330                 335

Val Asn Phe Lys Leu Leu Ser His Cys Leu Leu Val Thr Leu Ala Ala
            340                 345                 350

His Leu Pro Ala Glu Phe Thr Pro Ala Val His Ala Ser Leu Asp Lys
        355                 360                 365

Phe Leu Ala Ser Val Ser Thr Val Leu Thr Ser Lys Tyr Arg Gly Val
    370                 375                 380
```

```
Leu Ser Pro Ala Asp Lys Thr Asn Val Lys Ala Ala Trp Gly Lys Val
385                 390                 395                 400

Gly Ala His Ala Gly Glu Tyr Gly Ala Glu Ala Leu Glu Arg Met Phe
            405                 410                 415

Leu Ser Phe Pro Thr Thr Lys Thr Tyr Phe Pro His Phe Asp Leu Ser
            420                 425                 430

His Gly Ser Ala Gln Val Lys Gly His Gly Lys Lys Val Ala Asp Ala
            435                 440                 445

Leu Thr Asn Ala Val Ala His Val Asp Asp Met Pro Asn Ala Leu Ser
    450                 455                 460

Ala Leu Ser Asp Leu His Ala His Lys Leu Arg Val Asp Pro Val Asn
465                 470                 475                 480

Phe Lys Leu Leu Ser His Cys Leu Leu Val Thr Leu Ala Ala His Leu
                485                 490                 495

Pro Ala Glu Phe Thr Pro Ala Val His Ala Ser Leu Asp Lys Phe Leu
            500                 505                 510

Ala Ser Val Ser Thr Val Leu Thr Ser Lys Tyr Arg Gly Val Leu Ser
            515                 520                 525

Pro Ala Asp Lys Thr Asn Val Lys Ala Ala Trp Gly Lys Val Gly Ala
    530                 535                 540

His Ala Gly Glu Tyr Gly Ala Glu Ala Leu Glu Arg Met Phe Leu Ser
545                 550                 555                 560

Phe Pro Thr Thr Lys Thr Tyr Phe Pro His Phe Asp Leu
                565                 570

<210> SEQ ID NO 19
<211> LENGTH: 1764
<212> TYPE: DNA
<213> ORGANISM: Homo sapiens

<400> SEQUENCE: 19
agatcttatt gattgatttc ctcttgttgt tggtacagag taccaaggcg agtccaattc      60
ccggtaccat tttttcaacg actgcgcaac tgattgcgac aacgagtaca actgctgtac     120
ggcttgcgag acaggcgaga cagtctagaa gtacgagtat ttgacgcgca actgggccat     180
ttgaagttcg aagacagagt aacgacgac caatgagacc gacgagtaga cggccgtctt      240
aagtgaggcc gacaagtacg aagagaccta tttaaggacc gaagacacag ctgacaagac     300
tgaagattta tggcgccaca agacagaggc cgtctgtttt gattgcaatt cgacgaacc      360
ccatttcaac ctcgagtacg accacttatg ccacgacttc gtgagctcgc atacaaggac     420
agaaagggct gatgattttg catgaagggc gtaaagctgg acagagtacc taggcgagtc     480
caatttccag taccattttt tcaacgactg cgcaactgat tgcgacaacg agtacaactg     540
ctgtacggct tgcgagacag gcgagacagt ctagaagtac gagtatttga cgcgcaactg     600
ggccatttga agttcgaaga cagagtaacg acgaccaat gagaccgacg agtagacggc      660
cgtcttaagt gaggccgaca agtacgaaga gacctattta aggaccgaag acacagctga     720
caagactgaa gatttatggc gccacaagac agaggccgtc tgttttgatt gcaatttcga     780
cgaaccccat ttcaacctcg agtacgacca cttatgccac gacttcgtga gctcgcatac     840
aaggacagaa agggctgatg attttgcatg aagggcgtaa agctggaccc aagaccacca     900
agagtaccaa ggcgagtcca attcccggta ccattttttc aacgactgcg caactgattg     960
cgacaacgag tacaactgct gtacggcttg cgagacaggc gagacagtct agaagtacga    1020
gtatttgacg cgcaactggg ccatttgaag ttcgaagaca gagtaacgga cgaccaatga    1080
```

```
gaccgacgag tagacggccg tcttaagtga ggccgacaag tacgaagaga cctatttaag    1140
gaccgaagac acagctgaca agactgaaga tttatggcgc cacaagacag aggccgtctg    1200
ttttgattgc aatttcgacg aaccccattt caacctcgag tacgaccact tatgccacga    1260
cttcgtgagc tcgcatacaa ggacagaaag ggctgatgat tttgcatgaa gggcgtaaag    1320
ctggacagag tacctaggcg agtccaattt ccagtaccat ttttcaacg actgcgcaac     1380 tgattgcgac aacgagtaca actgctgtac ggcttgcgag acaggcgaga cagtctagaa    1440
gtacgagtat ttgacgcgca actgggccat ttgaagttcg aagacagagt aacggacgac    1500
caatgagacc gacgagtaga cggccgtctt aagtgaggcc gacaagtacg aagagaccta    1560
tttaaggacc gaagacacag ctgacaagac tgaagattta tggcgccaca agacagaggc    1620
cgtctgtttt gattgcaatt tcgacgaacc ccatttcaac ctcgagtacg accacttatg    1680
ccacgacttc gtgagctcgc atacaaggac agaaagggct gatgattttg catgaagggc    1740
gtaaagctgg acattactga cgtc                                           1764
```

OXYGEN-BINDING HEME PROTEINS INCORPORATING CIRCULARLY-PERMUTED GLOBINS

REFERENCE TO RELATED APPLICATION

This application is a 371 of PCT/US97/17294, filed Sep. 26, 1997.

This application claims priority upon U.S. Provisional patent application Ser. No. 60/026,831 filed Sep. 27, 1996, which is hereby incorporated herein by reference in its entirety.

This invention was made using government support under National Institutes of Health Grant No. PHS 5P01 HL-51084. The Government has certain rights in the invention.

BACKGROUND OF THE INVENTION

The present invention relates generally to oxygen-binding heme proteins, and in particular to such proteins incorporating one or more hemoglobin tetramers incorporating at least one functional, circularly-permuted globin.

As further background, blood transfusions allow trauma patients means to replenish blood loss, surgery patients to enter longer procedures with less risk, and rescue workers to bring a blood supply to accident victims. Although a transfusable blood supply provides many benefits, available blood is limited by human donations. In addition, the limited shelf-life of whole blood, disease transfer, and mismatched blood typing are problems yet to be fully addressed.

For example, the occurrence of an HIV-contaminated blood supply in the 1980's heightened awareness for a need to circumvent the problems associated with a donated blood supply. Even today, the United States Department of Health and Human Services has created a blood safety panel to examine many issues relative to donated blood, including HIV and hepatitis.

Transfused blood, containing plasma, white blood cells (leukocytes), platelets and red blood cells (erythrocytes), is generally used to carry oxygen from the lungs to the rest of the body's cells. A number of oxygen carrying solutions are being studied as alternatives to blood transfusions. In this regard, an effective blood substitute must satisfy three basic requirements. First, it must transport oxygen from lungs to tissues. Second, it must remain functional in vivo long enough to be effective; and third, it must not elicit harmful side effects. Blood substitutes studied to date include perfluorocarbons (Kaufman, R. J. (1991) in *Biotechnology of Blood* (J. Goldstein, e., Ed.) pp. 127–162, Butterworth-Heinemann, Boston), chemically modified hemoglobin from outdated human blood (Winslow, R. M. (1992) *Hemoglobin-based red cell substitutes,* Johns Hopkins University Press, Baltimore), and recombinant hemoglobins produced in microbial and mammalian hosts (Shen, T. -J., Ho, N. T., Simplaceanu, V., Zoiu, M., Green, B. N., Tam, M. F., & Ho, C. (1963), *PNAS USA* 90, 8108–8112; Rao, M. J., Schneider, K., Chait, B. T., Chao, T. L., Keller, H. Anderson, S., Manjula, B. N., Kumar, R., & Acharya, A. S. (1994) *ACBSIB* 22, 695–700).

On the subject of hemoglobin, each hemoglobin molecule is a tetramer of four smaller polypeptide subunits known as globins. A heme group, which is an iron-protoporphyrin complex, is associated with each polypeptide subunit, and is responsible for the reversible binding of a single molecule of oxygen. Normal adult hemoglobin is made up of two different kinds of polypeptide globins. A first globin, known as alpha globin, contains 141 amino acid residues. The second, known as beta globin, contains 146 amino acid residues. In normal adult hemoglobin, two of each kind of globin are arranged in the form of a truncated tetrahedron which has the overall shape of an ellipsoid.

The overall hemoglobin molecule is a 64,400 kDa protein. X-ray crystal structures show the size of HbAo to be about 64 Å×55 Å×50 Å (Fermi, G., Perutz, M. F., Shaanan, B. and Fourme, B. (1984) *Journal of Molecular Biology* 175, 159). The heme prosthetic group of each alpha subunit is non-covalently bound to the subunits by Lys E10, His CD3, Val E11, and Phe CD1. In beta chains, His CD3 is replaced by Ser CD3 The heme contains an Fe++ bound by the proximal histidine. A distal histidine hovers over the iron but does not coordinate; however, this histidine could sterically and/or electronically hinder the binding of CO, which has a higher affinity for heme than $O_2$, as well as hydrogen bond to iron in the deoxystate. The irons in the hemes can oxidize to the Fe+++ state, creating a nonfunctional hemoglobin (Bunn, H. F. a. F., B. G. (1986) in *Hemoglobin-Molecular, Genetic, and Clinical Aspects* (Dyson, J., Ed.) pp. 13–19, W. B. Saunders Company, Philadelphia).

Ligands that bind hemoglobin include CO, NO, CN—, and the most physiologically relevant ligand, $O_2$. Oxygen binding occurs in a sygmoidal pattern, demonstrating the cooperativity of multiple ligand binding. It has been shown that hemoglobin can exist in at least two states, T and R. The T state is associated with the deoxygenated state of hemoglobin, while the R state is associated with ligand bound hemoglobin. A number of models have been offered to describe the shift from T to R when ligand is bound. Two primary models describe the change in states as either a concerted change from T to R or a sequential change of subunits from T to R as ligand is bound. The concerted model proposed by Monod, Wynman, and Changeux describes cooperativity resulting from the entire tetramer converting from T to R (Monod, J., Wyman, J., and Changeux, J. -P. (1965) *Journal of Molecular Biology* 12, 88–118). The induced fit mode describes cooperativity as the result of an R state, ligand bound subunit inducing a neighboring T state subunit to alter to the R conformation (Koshland, D. E., Nemethy, G. and Filmer, D. (1966) *Biochemistry* 5, 365–385). Recently, Ackers and co-workers have proposed a symmetry model for T to R transition which provides evidence for an intermediate state in T to R transition (Ackers, G. K., Doyle, M. L., Myers, D., and Daugherty, M. A. (1992) *Science* 255, 54–63). The eight intermediate ligation states have been studied using metal-substituted hemes that are unable to bind ligand. The evidence demonstrates the steepest free energy change occurs when a subsequent ligand binds the alternate alpha/beta dimer.

Ligand affinity is also dependent on a number of allosteric effectors. The effectors that lower oxygen affinity include protons (Bohr effect), 2,3 diphosphoglycerate, and chloride ions. The physiological relevance of the effectors is to enhance oxygen delivery to metabolically active cells that produce $CO_2$.

Modification of human hemoglobin has been widely investigated as a means to provide a blood substitute and for other uses. Hemoglobin is a well-characterized protein, and can be altered to meet the basic requirements for an effective and safe blood substitute. Chemically modified, and more recently, recombinant forms of hemoglobin, are currently being tested in various stages of clinical trials.

Some problems arise from overproduction of recombinant hemoglobin in prokaryotes and eukaryotes. In humans, methionine aminopeptidase recognizes small, hydrogphobic residues as a signal to cleave (Hernan, R. A., Hui, H. L., Andracki, M. E., Noble, R. W., Sligar, S. G., Walder, J. A., & Walder, R. Y. (1992), Biochemistry 31, 8619–8628). Therefore, the first amino acid in postranslationally modified human hemoglobin is a valine. However, during the expression of human hemoglobin in *E. coli,* the initial methionine is not cleaved. Further, *E. coli* methionine peptidase recognizes small polar side chains, and expression in *E. coli* essentially adds a methionine to the primary sequence of both alpha and beta chains. This issue has been dealt with in two ways. A yeast expression system has been utilized in which the initial methionine is cleaved (Wagenbach, M., O'Roueke, K., Vitez, L., Wieczorek, A., Hoffman, S., Durfee, S., Tedesco, J., & Stetler, G. (1991) *Bio-Technology* 9, 57–61). In prokaryotic production, the replacement of the first amino acid - valine - with a methionine was used in both alpha and beta chains (recombinant hemoglobin des-val) to produce a protein functionally similar to HbAo (Hernan, R. A., Hui, H. L., Andracki, M. E., Noble, R. W., Sligar, S. G., Walder, J. A., & Walder, R. Y. (1992), *Biochemistry* 31, 8619–8628).

It has been reported that these overproduced hemoglobins are misassembled in the yeast and *E. coli* (Hernan, R. A., & Sligar, S. G. (1995) *JBC,* 270, 26257–26264). The misassembled tetramer initially binds ligand similarly to wild type hemoglobin, but over time drifts to different tetramer substrates that bind ligand at different rates. The drift appears to be time and temperature dependent, and protein stored at −70° C. still encounters a drift problem. Wild type hemoglobin stored at −70° C. has not demonstrated a similar effect.

Studies have shown that hemoglobin blood substitutes offer a number of difficulties as well as benefits. Hemoglobin is a powerful tool for oxygen delivery, but its use removes a tightly regulated protein from its native environment. One major problem for hemoglobin based blood substitutes occurs when oxygen in the heme iron dissociates as superoxide ion, leaving hemoglobin oxidized in the ferric "met" state. This autoxidation leaves hemoglobin in a state where it cannot bind ligand. Moreover, the Fe+++ state is an intermediate in the pathway to the highly reactive $Fe^{4}+$ ferryl state, heme loss, and can cause peroxidation of lipids (Giulivi, C., and Davies, K. J. A. (1994), *Methods of Enzymology* 231, 490–496; Yamamoto, Y., and La Mar, G. N. (1986) *Biochemistry* 25, 5288–5297; Repka, T., and Hebbel, R. P. (1991) *Blood* 78, 2753–2758). Superoxide off-rates appear to govern the measured autoxidation rate.

Another key problem associated with hemoglobin-based blood substitutes is hemoglobin's affinity for nitric oxide (NO), which is higher than its affinity for CO or $O_2$. NO is a vasodilator and can be carried by hemoglobin as a heme ligand or on a cysteine as a nitrosothiol (Bonaventura (1996) *Nature* 380, 221–226). Results in clinical trials demonstrate that patients treated with a hemoglobin-based blood substitute often encounter higher blood pressure (Blantz, R. C., Evan, A. P., and Gabbai, F. B. (1995) in *Blood Substitutes: Physiological Basis of Efficacy* (Winslow, R. M., Vandegriff, K. D., and Intaglietta, M., Ed.) pp. 132–142, Birkhauser, Boston). Another problem with hemoglobin is that the molecule is small enough to extravasate into the endothelial lining and bind NO. Patients treated with L-arginine, an intermediate in the NO synthesis pathway, or nitroglycerine, a vasodilator, have normal blood pressures while being administered hemoglobin solutions (see Blantz, R. C., Evan, A. P., and Gabbai, F. B. (1995) in *Blood Substitutes: Physiological Basis of Efficacy,* supra.

Perhaps the most significant drawback of hemoglobin blood substitutes is the rapid filtration of hemoglobin molecules by the kidney. At concentrations used in patients, hemoglobin dissociates into alpha/beta dimers small enough for renal filtration. This not only significantly decreases the lifetime of the blood substitute (half life of less than an hour), but it also deleteriously effects renal tubules and can cause renal toxicity (see Blantz, R. C., Evan, A. P., and Gabbai, F. B. (1995) in *Blood Substitutes: Physiological Basis of Efficacy,* supra).

One important step in eliminating renal toxicity is the cross-linking of alpha/beta dimers. Current efforts include chemical cross-linking of two alphas or two betas with a covalent attachment to lysine residues (Vandegriff, K. D., & Le Telier, Y. C. (1994) *Artificial-Cells-Blood-Substitutes-and-Immobilization-Biotechnology* 22, 443–455). In addition, hemoglobins have been randomly polymerized using glyceraldehyde (Vandegriff, K. D., & Le Telier, Y. C. (1994) *Artificial-Cells-Blood-Substitutes-and-Immobilization-Biotechnology* 22, 443–455). However, utilization of a chemical reaction significantly lowers the yield of functional protein.

Researchers have produced a genetically cross-linked hemoglobin molecule with a half life of almost two hours (Looker, D., Abbott-Brown, D., Cozart, P., Durfee, S., Hoffman, S. Mathews, A., Miller-Roehrich, J., Shoemaker, S., Trimble, S., Fermi, G., Komiyama, N. H., Nagai, K., & Stetler, G. L. (1992) *Nature* 356, 258–260). X-ray crystallography has shown the C-terminus of one alpha chain to be only 2 to 6 Å away from the N-terminus of the second alpha chain (Shaanan, B., (1983) *Journal of Molecular Biology* 171, 31–59), and trypsin catalyzed reverse hydrolysis has demonstrated that an additional amino acid attached to the C-terminus does not alter oxygen binding properties. These results, coupled with the knowledge that the C-terminal arg141 can form a salt bridge with the alternate alpha chain's val1, demonstrated the feasibility of genetically cross-linking the two alpha chains. The di-alpha chain expressed by these workers in *E. coli* consisted of an alpha des-val, a glycine linker, and a native alpha chain sequence. The construct was co-expressed with a des-val version of a naturally occurring low-oxygen affinity beta mutant (beta Presbyterian, R108K), and the entire construct was dubbed rHb1.1.

Despite these extensive efforts to develop a hemoglobin-based blood substitute, needs still exist for substitutes with increased crosslinking and higher molecular weight, which provide increased molecular stability and plasma half-life, and a decreased risk of renal toxicity. Such substitutes will desirably be readily expressed in host cells in high yield and have advantageous oxygen-binding capacity. The present invention addresses these needs.

SUMMARY OF THE INVENTION

Accordingly, one preferred embodiment of the invention provides a heme protein which includes a (i.e. at least one) hemoglobin molecule including at least one circularly permuted globin. In a preferred form, the invention takes advantage of the close proximity of the N and C termini of neighboring alpha chains, and a linker of one or more amino acids is inserted between both sets of termini. New termini are formed at any sequence position in the protein, and preferably at a position so as to be surface-exposed for linkage with other molecules, for example one or more other hemoglobin molecules to form recombinant hemoglobin multimers. Preferred proteins of the invention include at least one oxygen-binding hemoglobin tetramer having two alpha and two beta globins, wherein at least one of the globins is circularly permuted, and, more preferably, has surface-exposed N- and C-termini. Still more preferably, the hemoglobin molecule(s) in proteins of the invention will have multiple crosslinks between globins.

Another preferred embodiment of the invention provides a heme protein, preferably oxygen-binding, which includes at least one hemoglobin molecule including two beta globins and a di-alpha globin construct. The di-alpha globin construct includes a circularly-permuted alpha globin genetically crosslinked to another alpha globin. Thus the preferred di-alpha globin construct will include an amino acid sequence corresponding to a circular permutation of single polypeptide which has alpha chains whose original N- and C-termini are each linked to one another by a linker sequence of one or more amino acids. In an advantageous form, the di-alpha construct can be covalently linked to another protein, e.g. another di-alpha construct, by a polypeptide linker, to form proteins of high molecular weight, e.g. hemoglobin multimers.

Another preferred embodiment of the present invention provides a polynucleotide coding for a single polypeptide having a circularly-permuted alpha globin covalently linked to another alpha globin by two genetic crosslinks. Thus, preferred polynucleotides will sequentially encode (1) a first portion of a first, circularly-permuted alpha globin; (2) a first genetic crosslink; (3) a second alpha globin; (4) a second genetic crosslink; and (5) a second portion of the circularly permuted alpha globin, the first and second portions together constituting the entire circularly-permuted alpha globin. Thus, preferred polynucleotides will code for two alpha globins, a first of which is circularly permuted and a second of which is non-circularly permuted and occurs in the polypeptide linking the original N- and C-termini of the first alpha globin.

Still another preferred embodiment of the invention provides a circularly-permuted globin having termini located within a surface-exposed loop region of the globin (i.e. within any non-helicle surface-exposed alpha segment). The preferred, surface-exposed termini will be solvent-exposed (having no structures of the globin overlying the termini), and effective for covalent linking of one or both termini to an adjacent hemoglobin alpha or beta subunit, or to another molecule, e.g. to form a fusion protein. Preferred circularly-permuted alpha globins will have as terminal amino acids, residues 47 and 48, 48 and 49, 49 and 50, 50 and 51, 113 and 114, 114 and 115, 115 and 116, or 116 and 117 of the corresponding non-circularly permuted globin. Preferred circularly-permuted beta globins will have as terminal amino acids, residues 46 and 47, 47 and 48, 48 and 49, 118 and 119, 119 and 120, 120 and 121 and 121 and 122 of the non-circularly permuted beta globin.

Other preferred embodiments of the invention provide a polynucleotide encoding a circularly-permuted globin, a vector or host cell including such a polynucleotide, and a method for preparing a heme protein which involves culturing a host cell including and expressing such a polynucleotide.

The present invention also relates to a method of increasing tissue oxygenation in a warm blooded animal patient, e.g. human patient, comprising administering to the patient a therapeutically effective amount of an oxygen-binding heme protein of the invention.

The present invention also provides a method of replacing hemoglobin in the bloodstream of a warm blooded animal patient, e.g., a human patient, comprising administering to the patient an effective amount of a heme protein of the invention.

A still further preferred embodiment of the invention provides a method for inducing vasoconstriction in a warm blooded animal, e.g. a human patient, comprising introducing into the blood stream of the animal an effective amount of an oxygen-binding heme protein of the invention.

Another preferred embodiment of the invention provides a method for increasing the oxygenation of an isolated organ or tissue, for example during storage or transport, which includes the step of contacting the organ or tissue with an oxygen-binding heme protein of the invention.

Additional embodiments as well as objects, features and advantages of the invention will be apparent from the following description.

DESCRIPTION OF THE FIGURES

FIG. 2 shows the oligonucleotide cassette used in the generation of pSS1 (SEQ ID NOS: 1 and 2).

FIG. 3 shows the DNA sequence of the di-alpha gene contained in pSS1 (SEQ ID NOS: 3 and 5). The resulting amino acid sequence (SEQ ID NO: 4) and primary restriction sites are also shown.

FIG. 4 shows oligonucleotide cassettes, CP1 (SEQ ID NOS: 6 and 7) and CP2, (SEQ ID NOS: 8 and 9) used in the generation of pSLS21 and pSLS22 respectively.

FIG. 7 shows the DNA sequence (SEQ ID NOS: 10 and 12) of the circularly permuted di-alpha gene contained in pSLS22. The resulting amino acid sequence (SEQ ID NO: 11) and primary restriction sites are also included. Regions highlighted in bold are the glycine codon linking regions.

FIG. 9 shows oligonucleotide cassettes, TA1 (SEQ ID NOS: 13 and 14) and TA2 (SEQ ID NOS: 15 and 16), used in the generation of pSLS24 and pSLS25 respectively.

FIG. 12 provides a schematic representation of the ligation procedure used to generate pSLS26.

FIG. 13 shows the DNA sequence (SEQ ID NOS: 17 and 19) of the tetra-alpha gene contained in pSLS26. The resulting amino acid sequence (SEQ ID NO: 18) and primary restriction sites are also included. Regions highlighted in bold are the single glycine and Gly-Ser-Gly-Gly linking regions.

FIG. 16 provides a legend for the plasmid schematics shown in FIGS. 1, 5, 6, 8, 10, 11, 12, 14 and 15.

DESCRIPTION OF THE PREFERRED EMBODIMENTS

Figure 1:
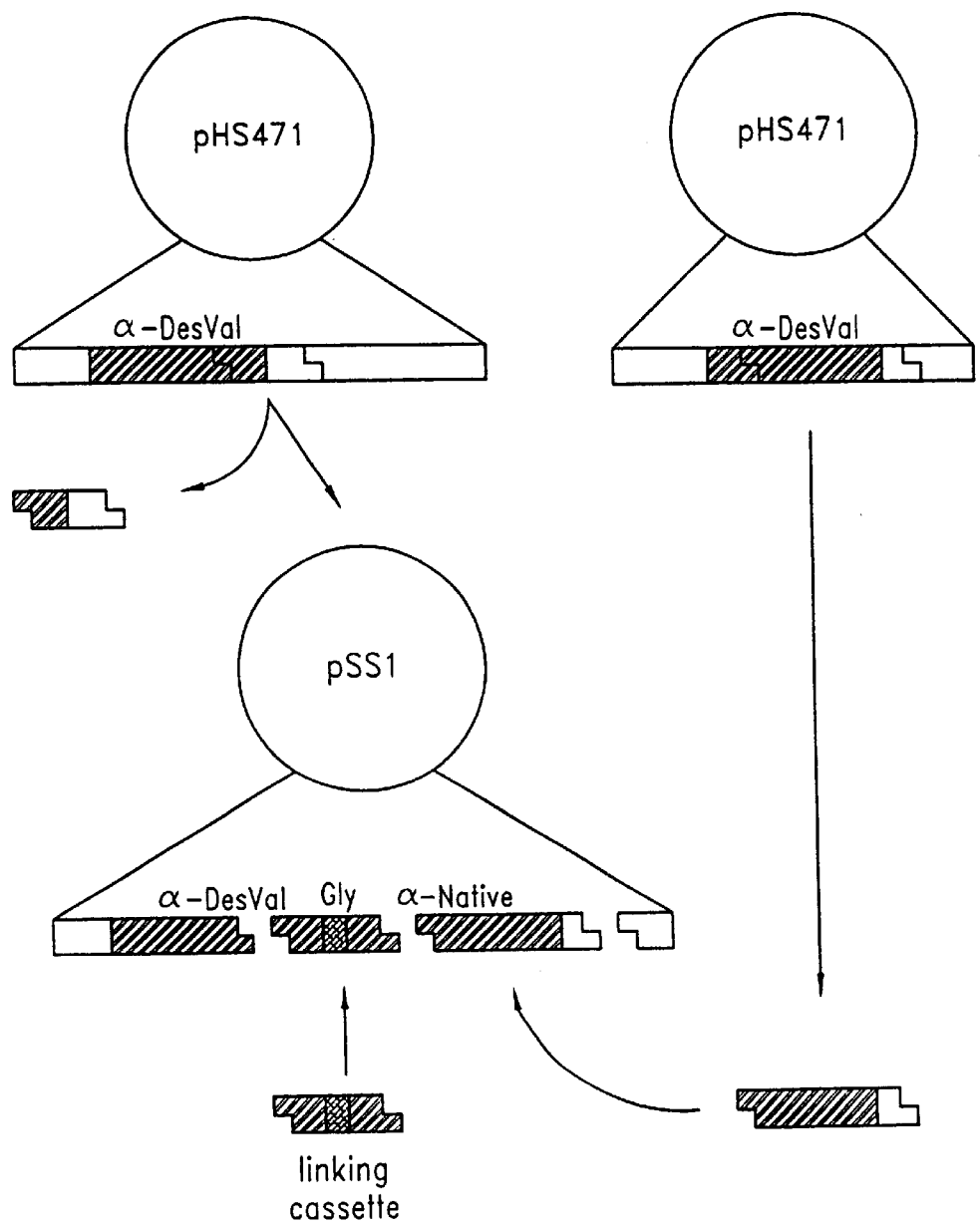
FIG. 1 provides a schematic representation of the ligation procedure used to generate pSS1.

For the purposes of promoting an understanding of the principles of the invention, reference will now be made to embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention pertains.

The following definitions are used herein.

Nucleotide—A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

Polynucleotide—A linear array of nucleotides connected one to the other by phosphodiester bonds between the 3' and 5' carbons of adjacent pentoses.

Polypeptide—A linear array of amino acids connected one to the other by peptide bonds between the alpha-amino and carboxy groups of adjacent amino acids.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell.

Vector—A plasmid, viral DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance.

Transformation—The introduction of DNA or RNA into cells in such a way as to allow gene expression.

Stroma—free preparation—a preparation free from red blood cells and red blood cell membrane fragments.

Crosslinked Hemoglobin Molecule—A hemoglobin molecule modified by covalent bond crosslinkage between one or more of its globin subunits.

Circularly-Permuted Globin—A globin having a covalent bond linkage between its native terminal amino acid residues and which has new terminal amino acid residues at another location of its polypeptide chain.

Genetic Crosslink—An amino acid or a polypeptide which covalently links two globins of a hemoglobin tetramer and which is formed upon expression of a polynucleotide encoding the two globins and the chain as a single polypeptide.

Native Termini—The termini amino acid residues of a globin prior to its circular permutation.

New Termini—The terminal amino acid residues of a globin after its circular permutation.

Globin—A compact protein domain containing heme preferably capable of forming higher molecular weight aggregates.

Hemoglobin—A protein of four globins.

Circularly-Permuted Hemoglobin Multimer—A protein which includes two or more hemoglobin molecules each having at least one circularly-permuted globin, wherein the circularly-permuted globins of adjacent hemoglobin molecules are covalently linked to one another by a linker chain of one or more amino acids.

As disclosed above, the present invention concerns novel heme proteins which have at least one hemoglobin molecule including at least one circularly-permuted globin. In this regard, a circularly permuted (CP) protein has its native termini linked, and new termini at some other location in its polypeptide chain. Thus, circularly-permuted proteins can be prepared by creating a circular primary sequence of the protein, and then recleaving the protein at another site, or by expression of a DNA sequence encoding an amino acid sequence corresponding to the recleaved protein. The resulting protein represents a new protein which has a primary amino acid sequence which differs significantly from that of the starting protein. However, for the sake of simplicity in nomenclature, the art has adopted the practice of referring to the new protein as a circularly-permuted "starting protein", a practice which will be followed herein for the sake of convenience when referring to a peptide having a primary amino acid sequence which corresponds to a circular permutation of the primary amino acid sequence of a known globin such as an alpha or beta globin. Similarly, tetrameric heme proteins of the invention which incorporate one or more circularly-permuted globins will be referred to as hemoglobins.

The present invention can be applied to conventional human hemoglobin and a wide variety of known hemoglobin mutants. In this regard, the amino acid sequences for the alpha and beta globins of conventional human hemoglobin are provided in Table 2, in which the abbreviations in Table 1 are employed.

TABLE 1

| Amino Acid | Abbreviation |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

TABLE 2

| Beta Globin | | Alpha Globin | |
|---|---|---|---|
| 1 | Val | 1 | Val |
| 2 | His | 2 | Leu |
| 3 | Leu | 3 | Ser |
| 4 | Thr | 4 | Pro |

TABLE 2-continued

| Beta Globin | | Alpha Globin | |
|---|---|---|---|
| 5 | Pro | 5 | Ala |
| 6 | Glu | 6 | Asp |
| 7 | Glu | 7 | Lys |
| 8 | Lys | 8 | Thr |
| 9 | Ser | 9 | Asn |
| 10 | Ala | 10 | Val |
| 11 | Val | 11 | Lys |
| 12 | Thr | 12 | Ala |
| 13 | Ala | 13 | Ala |
| 14 | Leu | 14 | Trp |
| 15 | Trp | 15 | Gly |
| 16 | Gly | 16 | Lys |
| 17 | Lys | 17 | Val |
| 18 | Val | 18 | Gly |
| 19 | Asn | 19 | Ala |
| 20 | Val | 20 | His |
| 21 | Asp | 21 | Ala |
| 22 | Glu | 22 | Gly |
| 23 | Val | 23 | Glu |
| 24 | Gly | 24 | Tyr |
| 25 | Gly | 25 | Gly |
| 26 | Glu | 26 | Ala |
| 27 | Ala | 27 | Glu |
| 28 | Leu | 28 | Ala |
| 29 | Gly | 29 | Leu |
| 30 | Arg | 30 | Glu |
| 31 | Leu | 31 | Arg |
| 32 | Leu | 32 | Met |
| 33 | Val | 33 | Phe |
| 34 | Val | 34 | Leu |
| 35 | Tyr | 35 | Ser |
| 36 | Pro | 36 | Phe |
| 37 | Trp | 37 | Pro |
| 38 | Thr | 38 | Thr |
| 39 | Gln | 39 | Thr |
| 40 | Arg | 40 | Lys |
| 41 | Phe | 41 | Thr |
| 42 | Phe | 42 | Tyr |
| 43 | Glu | 43 | Phe |
| 44 | Ser | 44 | Pro |
| 45 | Phe | 45 | His |
| 46 | Gly | 46 | Phe |
| 47 | Asp | 47 | Asp |
| 48 | Leu | 48 | Leu |
| 49 | Ser | 49 | Ser |
| 50 | Thr | 50 | His |
| 51 | Pro | 51 | Gly |
| 52 | Asp | 52 | Ser |
| 53 | Ala | 53 | Ala |
| 54 | Val | 54 | Gln |
| 55 | Met | 55 | Val |
| 56 | Gly | 56 | Lys |
| 57 | Asn | 57 | Gly |
| 58 | Pro | 58 | His |
| 59 | Lys | 59 | Gly |
| 60 | Val | 60 | Lys |
| 61 | Lys | 61 | Lys |
| 62 | Ala | 62 | Val |
| 63 | His | 63 | Ala |
| 64 | Gly | 64 | Asp |
| 65 | Lys | 65 | Ala |
| 66 | Lys | 66 | Leu |
| 67 | Val | 67 | Thr |
| 68 | Leu | 68 | Asn |
| 69 | Gly | 69 | Ala |
| 70 | Ala | 70 | Val |
| 71 | Phe | 71 | Ala |
| 72 | Ser | 72 | His |
| 73 | Asp | 73 | Val |
| 74 | Gly | 74 | Asp |
| 75 | Leu | 75 | Asp |
| 76 | Ala | 76 | Met |
| 77 | His | 77 | Pro |
| 78 | Leu | 78 | Asn |
| 79 | Asp | 79 | Ala |
| 80 | Asn | 80 | Leu |
| 81 | Leu | 81 | Ser |
| 82 | Lys | 82 | Ala |
| 83 | Gly | 83 | Leu |
| 84 | Thr | 84 | Ser |
| 85 | Phe | 85 | Asp |
| 86 | Ala | 86 | Leu |
| 87 | Thr | 87 | His |
| 88 | Leu | 88 | Ala |
| 89 | Ser | 89 | His |
| 90 | Glu | 90 | Lys |
| 91 | Leu | 91 | Leu |
| 92 | His | 92 | Arg |
| 93 | Cys | 93 | Val |
| 94 | Asp | 94 | Asp |
| 95 | Lys | 95 | Pro |
| 96 | Leu | 96 | Val |
| 97 | His | 97 | Asn |
| 98 | Val | 98 | Phe |
| 99 | Asp | 99 | Lys |
| 100 | Pro | 100 | Leu |
| 101 | Glu | 101 | Leu |
| 102 | Asn | 102 | Ser |
| 103 | Phe | 103 | His |
| 104 | Arg | 104 | Cys |
| 105 | Leu | 105 | Leu |
| 106 | Leu | 106 | Leu |
| 107 | Gly | 107 | Val |
| 108 | Asn | 108 | Thr |
| 109 | Val | 109 | Leu |
| 110 | Leu | 110 | Ala |
| 111 | Val | 111 | Ala |
| 112 | Cys | 112 | His |
| 113 | Val | 113 | Leu |
| 114 | Leu | 114 | Pro |
| 115 | Ala | 115 | Ala |
| 116 | His | 116 | Glu |
| 117 | His | 117 | Phe |
| 118 | Phe | 118 | Thr |
| 119 | Gly | 119 | Pro |
| 120 | Lys | 120 | Ala |
| 121 | Glu | 121 | Val |
| 122 | Phe | 122 | His |
| 123 | Thr | 123 | Ala |
| 124 | Pro | 124 | Ser |
| 125 | Pro | 125 | Leu |
| 126 | Val | 126 | Asp |
| 127 | Gln | 127 | Lys |
| 128 | Ala | 128 | Phe |
| 129 | Ala | 129 | Leu |
| 130 | Tyr | 130 | Ala |
| 131 | Gln | 131 | Ser |
| 132 | Lys | 132 | Val |
| 133 | Val | 133 | Ser |
| 134 | Val | 134 | Thr |
| 135 | Ala | 135 | Val |
| 136 | Gly | 136 | Leu |
| 137 | Val | 137 | Thr |
| 138 | Ala | 138 | Ser |
| 139 | Asn | 139 | Lys |
| 140 | Ala | 140 | Tyr |
| 141 | Leu | 141 | Arg |
| 142 | Ala | | |
| 143 | His | | |
| 144 | Lys | | |
| 145 | Tyr | | |
| 146 | His | | |

There are also hundreds of known mutations of hemoglobin which involve changes in the amino acid structure of the polypeptide chains. For example, a mutant form of alpha globin (des-val) is used in the specific Experimental below. This alpha globin has a valine→methionine substitution at amino acid 1 of the chain. Other known alpha mutants include but are not limited to such modifications as amino acid 94 aspartic acid →asparigine in the alpha chain (Hb Titusville).

A number of known mutant hemoglobins have amino acid substitutions at human beta globin positions 90, 102, 108 and combinations thereof. Some specific examples of beta mutations are but are not limited to:

(1) amino acid 90 glutamine→lysine (hemoglobin Agenogi)

(2) amino acid 90 glutamine→glycine (3) amino acid 108 asparagine→aspartic acid (hemoglobin Yoshizuka)

(4) amino acid 102 asparagine→threonine (hemoglobin Kansas)

(5) amino acid 102 asparagine→serine (hemoglobin Beth Israel)

(6) amino acid 90 glutamic acid→valine amino acid 91 Leucine→methionine amino acid 93 cysteine→serine amino acid 94 aspartic→glutamic acid A Table including a listing of some additional illustrative hemoglobin variants is set forth in Appendix A attached hereto and made a part hereof, taken from *Hemoglobin*, Vol 19, No. 1–2, pp. 39–124, Marcel Dekker (1995).

In addition to known mutations other mutations can be engineered into these circularly permuted globins in order to add additional desirable properties into the protein or protein multimer. For example, mutations that alter the electronic environment of the heme may be included to stabilize the reduced, physiologically active, form of the molecule or alter the ligand affinity and selectivity.

Generally speaking, in the present invention, the new termini of the globin subunit are formed at a site that does not eliminate the function of the globin in assembling with other globins to form an oxygen-binding, tetrameric heme protein. Thus, the resulting protein will possess the function of interest of the wild type hemoglobin, e.g. the capacity to bind oxygen at some level, which can be the same level, or a level which is increased or decreased relative to the wild type protein.

Generally speaking, preferred candidate locations for forming the new termini will fall within surface-exposed loop regions on the globins, rather than in alpha helical segments. This is expected to minimize disruption of the protein structure since the loops are not highly ordered. More preferred regions for introducing new termini in alpha globins include the loop region between the C and E helices (residues 47–51) and the loop region between the G and H helices (residues 113–117). The loop region between the C and E helices is most preferred. Thus, in the Experimental below, new termini were created at original serine 49 (new N terminus) and original leucine 48 (new C terminus) of normal adult human alpha globin.

In the circular permutation of a human beta globin (see e.g. Table 1), a longer linker may be used to join the native termini because the termini are not as spacially close as those of the alpha chains. For example, a polypeptide linker of about three to five residues may be used. Because the beta chains are structurally similar to the alpha chains, the preferred sites for introduction of new termini in beta chains generally include the same loop regions selected for the alpha chains. These include, but are not limited to, the loop region between helices C and D (residues 46–49), and the loop region between helices G and H (residues 118–122). Of these, the loop region between helices C and D is most preferred.

The new termini of the circularly-permuted globins of the invention are preferably exposed on the surface of the globin when assembled in the ellipsoid, tetrameric hemoglobin. The selection of new termini may be assisted in this regard by conventional modeling software, for example modeling protein structure on a Silicon Graphics Imaging computer using molecular modeling software to verify surface exposure of amino acids. Location of the new termini at the surface of the hemoglobin molecule facilitates covalent linkage of the molecule to other molecules through amino acid or polypeptide linkers. In one preferred practice of the invention, a hemoglobin multimer is provided, in which a plurality of hemoglobin molecules are covalently linked to one another by polypeptide linkers spanning between circularly-permuted globins of the respective hemoglobin molecules. In this regard, the length of this polypeptide linker can vary widely to suit a particular application; however, it is expected that polypeptide linkers having about one to about twenty amino acids will be suitable for most applications, more commonly having about one to about ten amino acids. In the applicants' preferred work, the polypeptide linker included a number of glycine residues in order to impart conformational freedom to the linker. In addition, the intermolecular linker will likely be solvent exposed, and thus hydrophilic residues can be used to advantage, for example, amino acid residues containing hydroxyl or acidic groups, e.g. the hydroxyl-containing serine used in the specific work reported in the Experimental below. Generally speaking, the selection and use of suitable amino acids in the intermolecular linker will be well within the purview of those skilled in the field.

Similarly, the number of hemoglobin molecules in hemoglobin multimers of the invention may vary, including multimers having up to and exceeding about one hundred hemoglobin repeating units. Again, for most applications it is expected that a smaller number of repeating units will be suitable, e.g. in the range of two to about ten hemoglobin repeating units.

To create intramolecular crosslinks between globins of a hemoglobin molecule, it is desirable to use a chain of one to about seven amino acids, more preferably from one to about three amino acids. Any suitable amino acid or set of amino acids may be used for this purpose, including for example one or more amino acids selected from those identified in Table 1, above. The selection and use of suitable amino acids in the crosslinks will be well within the purview of those skilled in the field.

Amino acid crosslinks such as those discussed above are conveniently introduced as genetic crosslinks. Other modes of introducing intramolecular and/or intermolecular crosslinks may also be used, including for example chemical treatment with crosslinking agents. Such crosslinking agents may include dialdehydes, such as glyoxal, amlonic dialdehyde, succinic dialdehyde, glutaraldehyde, adipaldehyde, 3-methylglutaraldehyde, propyladipaldehyde, phthalic dialdehyde, terephthaldehyde and malonic dialdehyde. See, e.g. Bonsen et al., U.S. Pat. Nos. 4,001,200; 4,001,401; and 4,053,590; and Bonhard et al., U.S. Pat. Nos. 4,136,093 and 4,336,248.

Preferred crosslinked hemoglobin molecules will exhibit increased molecular stability as compared to native, non-crosslinked hemoglobins. This stability may be demonstrated, for instance, by increased thermal stability (e.g. melting points) of the hemoglobin molecules as compared to their non-crosslinked counterparts.

The present invention also concerns an isolated polynucleotide, preferably DNA sequence, coding for a circularly-permuted globin, such as a human alpha or human beta globin. Such polynucleotides can be created, for example, by chemical synthesis of a polynucleotide having the desired sequence corresponding to a circular permutation of the globin gene at hand. Such polynucleotides of the invention may also be prepared by ligating the ends of the globin coding sequence of interest, directly or via a base sequence coding for an amino acid linker, and then cleaving the resulting circular sequence to result in the circularly-permuted sequence Genetic manipulations to create circularly-permuted sequences can be applied without undue experimentation to form a wide variety of polynucleotides coding for circularly-permuted globins and constructs including them, in accordance with the present invention.

In a preferred aspect the invention provides a polynucleotide, such as a DNA or RNA sequence, preferably a DNA sequence, which encodes a single polypeptide which includes, in sequence: (I) a first portion of a first, circularly-permuted globin; (ii) a first genetic crosslink; (iii) a second, entire globin; (iv) a second genetic crosslink; and (v) a second portion of the circularly-permuted globin, wherein the first and second portions together constitute the entire circularly-permuted globin. The coded polypeptides also form a part of the present invention and, generally speaking, include a first, circularly-permuted globin having its original N- and C-termini joined by a linking polypeptide including the amino acid sequence of a second, non-circularly-permuted alpha globin. More preferably, the first and second globins of such constructs are alpha globins, and the first and second genetic crosslinks (the peptide sequences occurring between the N- and C-termini of the circularly permuted globin and those of the non-circularly-permuted globin) will have from one to about three amino acids.

DNA or other polynucleotides for use in carrying out the present invention may be synthetically created, by hand or with automated apparatus. Means for synthetic creation of the polynucleotide sequences of the invention are generally known to those of ordinary skill in the art, particularly in light of the teachings contained herein. For additional details as to polynucleotide synthesis, reference can be made to standard texts on the subject including for instance Maniatis et al., *Molecular Cloning- A Laboratory Manual,* Cold Spring Harbor Laboratory (1984), and Horvath et al. *An Automated DNA Synthesizer Employing Deoxynucleoside 3'-Phosphoramidites,* Methods in Enzymology 154:313–326, 1987, both hereby incorporated herein by reference. Additionally, polynucleotide sequences of the invention may be constructed by isolating and modifying a polynucleotide which occurs in nature. For instance, a starting globin polynucleotide may be a restriction fragment isolated from a genomic or cDNA library. The starting polynucleotide can then be manipulated using known techniques to produce a polynucleotide of the invention which encodes a circularly-permuted globin, generally as discussed above.

The invention also provides expression or cloning vectors including polynucleotide sequences of the invention, including for instance plasmid vectors, viral vectors, and the like. The synthesis and/or isolation of necessary and desired component parts of expression or cloning vectors, and their assembly, is within the abilities of those of ordinary skill in the art and, as such, are capable of being performed without undue experimentation.

The present invention also concerns a host cell including a polynucleotide of the invention and which expresses the polynucleotide. Such host cells can be made by transforming a cell with a suitable vector carrying a polynucleotide of the invention, for example a plasmid or viral vector. The polynucleotide of the invention can also be introduced into cells using other known techniques, including for example microinjection, electroporation or the like.

The host cell can be selected from a variety of host cells which effectively express hemoglobin, including for instance mammalian cells such as human, murine or porcine cells, gram positive or negative bacterial cells such as *E. Coli.,* Bacillus or Salmonella, yeast cells such as *Sacharomyces Cerevisiae* or *Sacharomyces Pombe,* or insect cells. Further, host cells which express polynucleotides of the invention can be cultured so as to produce circularly-permuted globins of the invention in high yield. The globins can then be individually isolated or, more preferably, the circularly-permuted globin is co-expressed in the host cell with other globins as necessary to produce the oxygen-binding heme protein including at least one assembled hemoglobin tetramer in the cell. Thus, for instance, in the Experimental below, the di-alpha or tetra-alpha globin constructs were co-expressed in host cells with beta globin, and the corresponding assembled hemoglobin tetramer or octamer were isolated from the cells in high yield. In this regard, isolation and purification of inventive proteins from the cultured host cells can be achieved using conventional techniques such as filtration, centrifugation, chromatography, and the like. Substantially purified preparations of heme proteins of the invention can thereby be prepared.

Heme proteins of the invention exhibit useful properties as blood and hemoglobin substitutes. For example, the tetrameric and octameric heme proteins disclosed in the Experimental exhibit increased stability against thermal denaturation as compared to prior-known hemoglobin-based blood substitutes. Also, ligand binding experiments have demonstrated that these proteins possess ligand binding properties characteristic of wild-type hemoglobin, including oxygen binding, geminate recombination and CO on-rate.

For use, heme proteins can be incorporated into pharmaceutically acceptable carriers to form pharmaceutical compositions, if desired. Sterile, liquid carriers, particularly aqueous carriers, or liposomes or other polymerizing and encapsulating polymers, will be preferred, for example a balanced electrolyte and buffer solution. The heme protein is desirably at a concentration of about 1 to about 20% in solution, with the precise concentration employed depending upon the application. The hemoglobin may also be dissolved in known plasma expanders such as colloids (plasma, albumin) or crystalloids (saline, glucose, dextran, gelatins, Hemasol* or Lactated Ringer's), or contained in natural red blood cells or in artificial red blood cells such as liposomes.

The thus-prepared pharmaceutical preparation can then be conventionally administered to a human or other animal patient, for example by injection, catheterization, or the like. For convenience in these purposes, the pharmaceutical preparation can be contained in a sterile, medical-grade container such as a vial, syringe, or infusion bag.

The oxygen-binding heme proteins of the invention may be used, for instance, in a stroma-free hemoglobin-type blood replacement, or to improve tissue oxygenation in disease states associated with compromised oxygen delivery to tissue including myocardial infarction, stroke, small vessel disease such as diabetes, etc. Heme proteins of the invention can further be used to increase oxygenation of tissues (e.g. tumor cells or other tissues having hypoxic cells due to damage by physical or chemical means, e.g., burns, exposure to chemicals, physical injuries or ionizing radiation). In one specific application, heme proteins of the invention may be used to increase oxygenation in hypoxic tumor cells to be subjected to radiation therapy, so as to increase the efficacy of the therapy (see, e.g., U.S. Pat. No.

5,295,944). Many tumors exhibit oxygen heterogeneity, including regions of hypoxia, which protect tumor cells against the cytotoxic action of ionizing radiation. Examples include solid tumors such as sarcomas, carcinomas and lymphomas, and some cases of dispersed tumor cells wherein masses of tumor cells form which can produce regions of oxygen heterogeneity, e.g. advanced leukemia. In such cases an increase in the oxygenation of the tumor tissue can enhance the effect of radiation therapy on the tissue.

In order to increase oxygen transport to the site of a tumor, a preparation including a heme binding protein of the invention can be administered, e.g. intravenously, to the patient. The chemotherapeutic agent can then be administered, with the amount of time between the administration of the heme protein preparation and chemotherapeutic agent depending upon factors such as the amount of time it takes the heme protein preparation to be fully incorporated into the circulatory system of the host, the lifetime of the preparation, etc. Also, the patient may breath oxygen-enriched gas prior to and after the administration of the ionizing radiation. This can be done by having the host breath oxygen-enriched air, 100% oxygen or carbogen (95% oxygen/5% $CO_2$), or in certain cases exposing the host to hyperbaric oxygen conditions.

Any type of ionizing radiation which exhibits an antitumor effect can be employed, including as examples X-rays, gamma rays, high-energy electrons and High LET radiation, such as protons, neurons and alpha particles. Such ionizing radiation can be administered using techniques well-known to those skilled in the art. For example, X-rays and gamma rays are applied by external and/or interstitial means from linear accelerators or radioactive sources. High energy electrons can be produced by linear accelerators. High LET radiation is also produced by linear accelerators and can also be applied from radioactive sources implanted interstitially. Dosages of the ionizing radiation are generally those conventionally applied in radiotherapeutic treatment of tumors, although in certain cases usage of the oxygen-binding heme protein may lower the necessary dosage of ionizing radiation.

In another area, heme proteins of the invention can be used in low doses to increase perfusion when desired. For example, the heme protein may be administered to increase blood pressure from abnormally low levels, as in shock of hemorrhagic, cardiogenic or septic origin, or to increase blood pressure from normal levels to effect improved perfusion, for instance as in stroke therapy. Heme proteins of the invention may also be used in oxygen sensors.

In addition, heme proteins of the invention may be attached, e.g. covalently bonded, to other molecules via a surface-exposed, terminal amino acid or a polypeptide extending therefrom, to form additional materials in accordance with the present invention. For example, in one aspect, a heme protein of the invention can be conjugated to another molecule to form an active conjugate with increased vascular retention time as compared to that of the other molecule, and thus effectively modulate (increase) the vascular retention time of the other molecule. In one mode, the conjugate can be prepared by genetically linking a heme protein of the invention with the other molecule. Thus, a polynucleotide coding for both the heme protein and the other molecule can be constructed and introduced into a suitable host cell for expression. Expression of the DNA will then provide the conjugate. Heme proteins of the invention having surface-exposed termini will be particularly advantageous for these purposes. Because the termini are surface-exposed and not integrally involved in the structure of the heme protein, the linkage to other molecules will not significantly disrupt the structure of the heme protein, thus leaving it functional, and will also allow the attached molecule to remain in solution as opposed to being buried within the heme protein. There are a number of therapeutic peptides currently in use which would be expected to benefit from increased retention times when conjugated with heme proteins of the invention, including for instance insulin, erythropoietin, and growth hormones such as somatotropins. In the case of erythropoietin, as an example, the administration of a heme protein of the invention genetically linked to erythropoietin (a hormone which promotes red blood cell production in the body), may be used to replenish red blood cell supply of a patient before the blood substitute has degraded and been filtered by the blood stream.

Heme proteins of the invention can also be attached ex-vivo to non-peptides such as organic molecules, DNA and the like. Numerous methods are known for covalently linking compounds to specific chemical moieties on proteins, such as directing crosslinking reagents to lysine on heme proteins of the invention provide a unique reactive sites on the protein for crosslinking to other molecules, which can be capitalized upon using known chemistries. Illustrative attachment chemistries are described for example in T. E. Creighton (1983) "Proteins: Structure and Molecular Properties", W. H. Freeman, N.Y.; and W. D. Dandliker and A. J. Portman (1971) "Excited States of Proteins and Nucleic Acids", R. F. Steiner and I. Weinryb eds., Plenum Press, N.Y., pp. 199–276.

Heme proteins of the invention can also be attached to pharmaceutically active compounds in a specific 1:1 stoichiometry and it is expected that such will be accomplished without deleterious effect on the structural integrity of the heme proteins. Proteins of the invention may also be attached to targeting agents such as antibodies, or can be used advantageously as MRI imaging agents themselves or attached to other imaging (e.g. MRI or X-ray) or therapeutic agents.

For the purposes of promoting a further understanding of the present invention, its principles and its advantages, the following Experimental is provided. It will be understood that this Experimental is illustrative, and not limiting, of the invention.

EXPERIMENTAL

E. coli strains and plasmid vectors used

The E. coli strain DH5a was used in all the genetic engineering and protein expression of the gene constructs described below. Plasmids pHS471 and pWHS486, used in the genetic constructions, were generated previously by Hernan et. al. (Biochemistry, 31:8619–28 (1992)). pUC18 is a commercially available plasmid from New England BioLabs.

Generation of DNA cassettes for genetic engineering

Most of the genetic manipulations utilized cassette mutagenisis, which entails the generation of a pair of complementary oligonucleotides which contain the desired coding region. All oligonucleotides were synthetically prepared by and purchased from the genetic engineering facility at the University of Illinois. 400 picomoles of each oligonucleotide was phosphorylated with 10 units of T4 polynucleotide kinase in 100 $\mu$L containing 50 mM Tris-HCl, pH 7.6/10 mM $MgCl_2$/5 mM DTT/100 $\mu$M EDTA for 60 min. at 37° C. After phosphorylation, the complementary oligonucleotides were annealed by mixing and heating to 95° C. for 5 min. and allowed to slowly cool to room temperature over a 3–4 hr. period. The resulting fragments have sticky ends corresponding to restriction sites allowing for ligation to gene fragments or plasmid vectors. For the purposes herein and as generally understood in the art, a "cassette" refers to a pair of complementary oligonucleotides prepared in the fashion described above.

Plasmid Mini-Preparations

All plasmid isolations were performed from a 5 mL overnight culture of *E. coli* DH5a, harboring the plasmid of interest, grown in LB media (10 g Tryptone, 5 g Yeast Extract, 5 g NaCl per liter). The commercially available Qiagen Spin Plasmid Mini-Preparation kit was used to purify the DNA. The Qiagen kit gives a high yield of RNA free plasmid. DNA were eluted in 25 $\mu$L of water.

Restriction digests

All restriction digests were performed at 37° C. 1–10 units of enzyme were used for each digestion and the reactions were carried out in a final volume of 10 $\mu$L. The enzymes were purchased from New England Bio-Labs or GIBCO BRL. The buffer systems used were supplied with the enzymes.

DNA fragment isolation and purification

Restriction enzyme digested DNA fragments that were subsequently used in ligation reactions were separated on a 1% agarose gel with 10 $\mu$g/mL ethidium bromide at 130 V for about 1 hour. The selected DNA bands were removed with a razor blade, and the resulting DNA was isolated from the gel fragment using the GeneClean II kit from BioLab 101.

DNA Ligations

Genecleaned plasmid fragments and oligonucleotides were ligated in a total reaction volume of 20 $\mu$L with 1 unit of T4 DNA ligase(GIBCO BRL). Vector to fragment/cassette insert ratios varied between 1:3 and 1:50. Ligations ran for one hour at room temperature or 16° C. overnight.

Competent Cells and Transformations

*E. coli* DH5a was grown in a 5 mL overnight culture of LB media. 500 $\mu$L of the overnight culture was used to inoculate 50 $\mu$L of LB. The cells grew 3–4 hours and were spun at 5000 g for 5 minutes. The cells were resuspended in 25 mL of cold 0.1 M $CaCl_2$. After a 20 minute incubation on ice, the cells were again spun down under the same conditions. The pellet was then resuspended in 4 mL of cold $CaCl_2$.

Competent *E. coli* were transformed with finished ligation reactions or mini-prepped DNA. The ligation mixture or 0.5 $\mu$g of mini-prepped DNA were mixed with 200 $\mu$L of competent cells and incubated on ice for 20 minutes. The cells were heat shocked at 37° C. for 2 minutes and placed immediately on ice for 5 minutes. One mL of LB media was added, and the cells were incubated for one hour at 37° C. in order to produce ampicillin resistance. 200 $\mu$L of cells were plated on LB plates with agarose (15 g/L) and ampicillin (0.2 g/L). The remaining cell mixtures were spun down, part of the supernatant was removed, and the pelleted cells were resuspended and plated as well.

DNA Sequencing

Gene sequencing was performed at the University of Illinois DNA Sequencing Facility using a Perkin/Elmer DNA Sequencer with PCR amplification. Sequencing reactions were stopped with fluorescently labeled dideoxy nucleotides. Universal and reverse primers for pUC sequencing initiated the reactions.

Construction of Di-alpha globin gene

The alpha des-val gene (pHS471) was used to create a tandem fusion of two alpha globin gene sequences. pHS471 was digested with SalI and PstI to yield a vector containing the majority of the first alpha globin. Then an alpha gene fragment was generated from the digestion of pHS471 with SacI and PstI. This fragment was then ligated into the vector along with a linking cassette which codes for the last portion of the first alpha gene beginning with the SalI restriction site, a glycine codon, and the first portion of the second alpha gene through the SacI restriction site to generate pSS1. A schematic of this ligation procedure is included in FIG. 1. The DNA sequence of the linking cassette and the di-alpha gene in pSS1 is in FIGS. 2 and 3, respectively.

The sequence of the construct was confirmed. The linking region was sub-cloned by digestion of the dialpha vector with BamHI and subcloning into the BamHI site of pUC18. The resulting plasmid was sequenced at the University of Illinois sequencing facility.

Construction of the circularly permuted di-alpha gene

Figure 5:
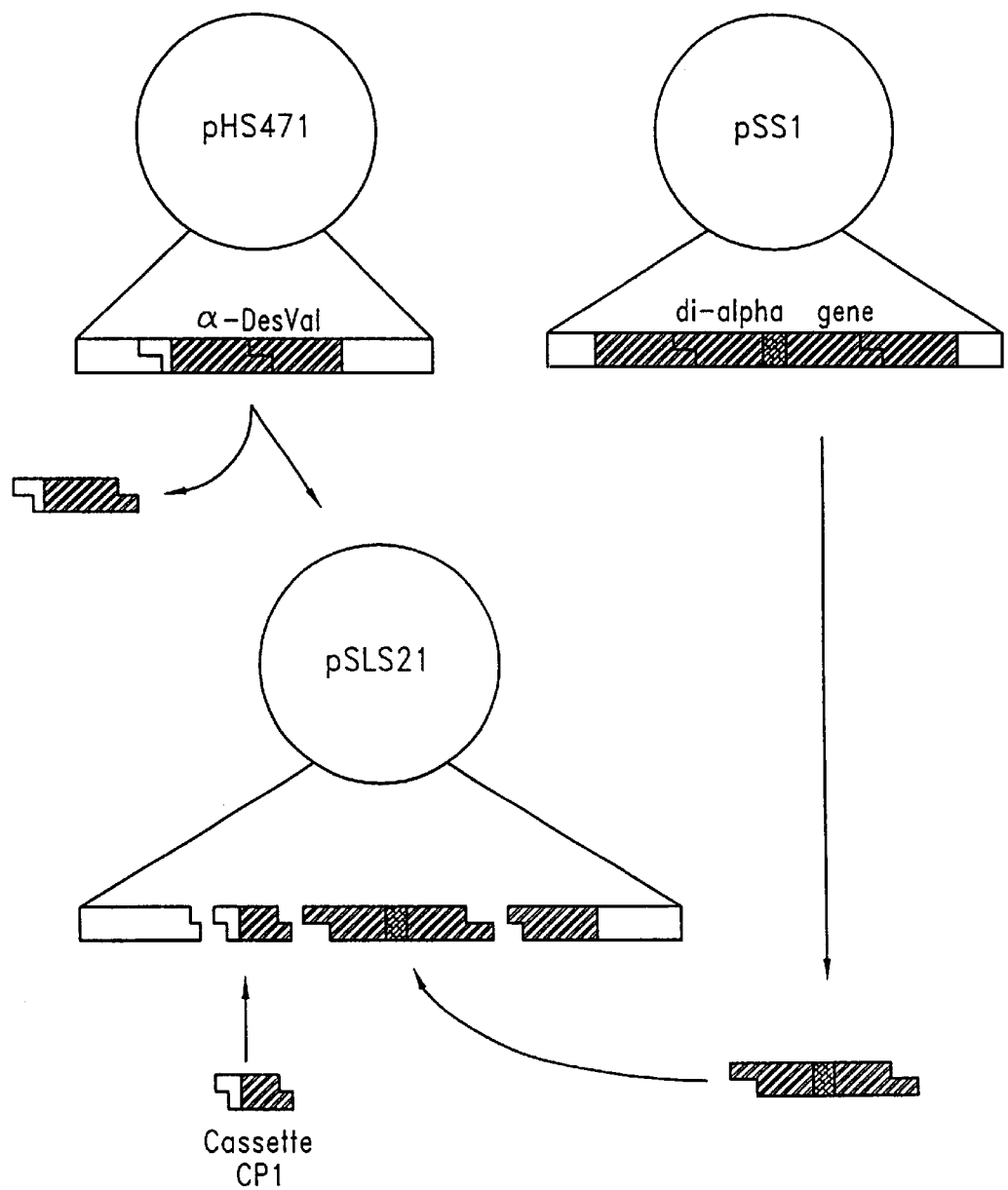
FIG. 5 provides a schematic representation of the ligation procedure used to generate pSLS21.
Figure 6:
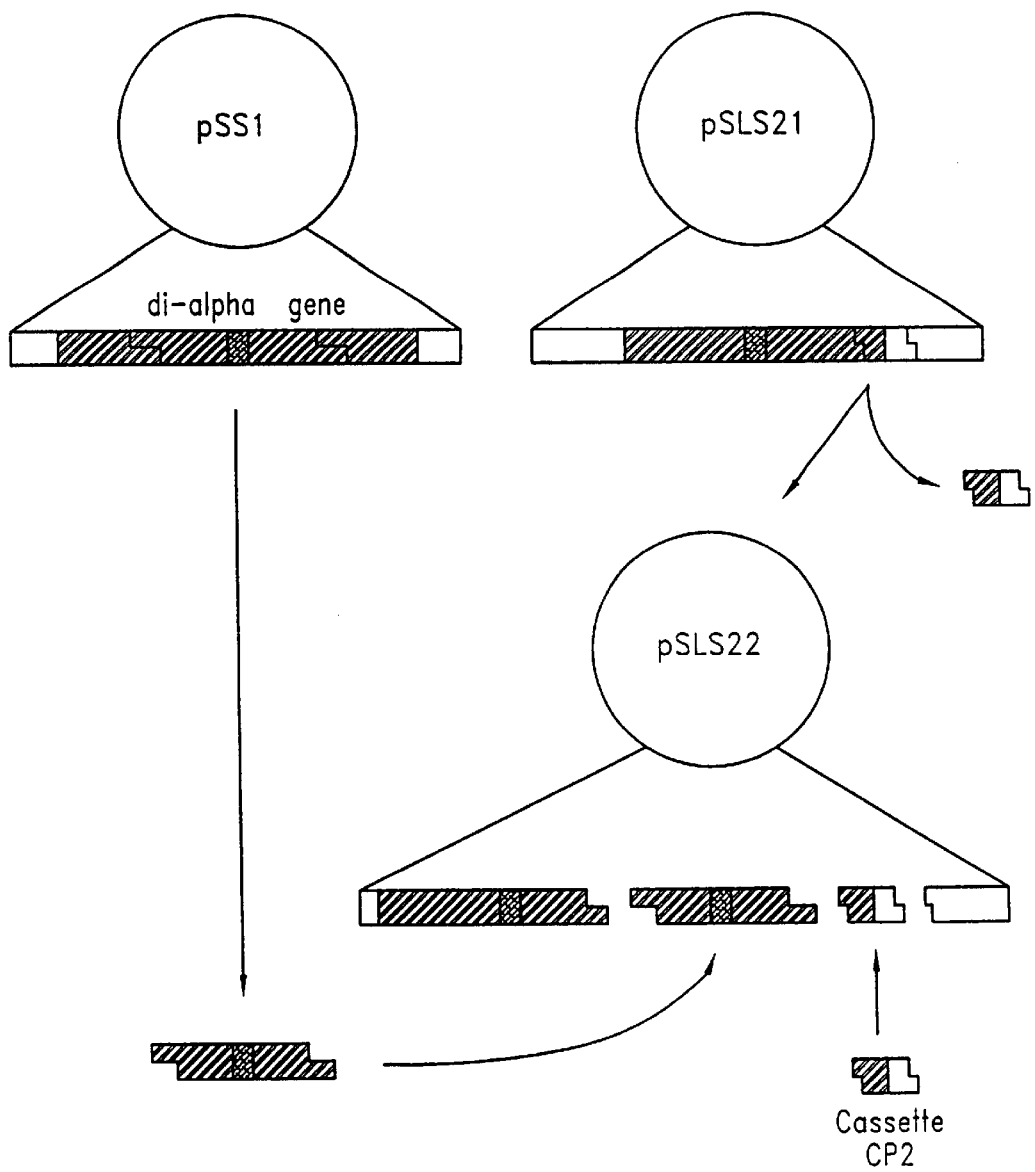
FIG. 6 provides a schematic representation of the ligation procedure used to generate pSLS22.

The pSS1 created as described above was utilized for the generation of a circularly permuted dialpha globin gene. Two ligation steps and two cassettes were required for the synthesis. The sequence of cassette CP1 and CP2 are shown in FIG. 4. In the first step, cassette CP1 and a 400 base pair fragment generated from an MluI/BamHI digest of pSS1 was ligated into pHS471 digested with XbaI and BamHI to generate pSLS21 (FIG. 5). Then cassette CP2 and a 400 base pair fragment generated from an XhoI/BamHI digest of pSS1 was ligated into pSS21 digested with BamHI and PstI to generate pSLS22 (FIG. 6).

The DNA sequence of pSLS21 was confirmed by sequencing in both the forward and reverse directions at the University of Illinois sequencing facility. The sequence along with the corresponding amino acids are shown in FIG. 7.

Figure 8:
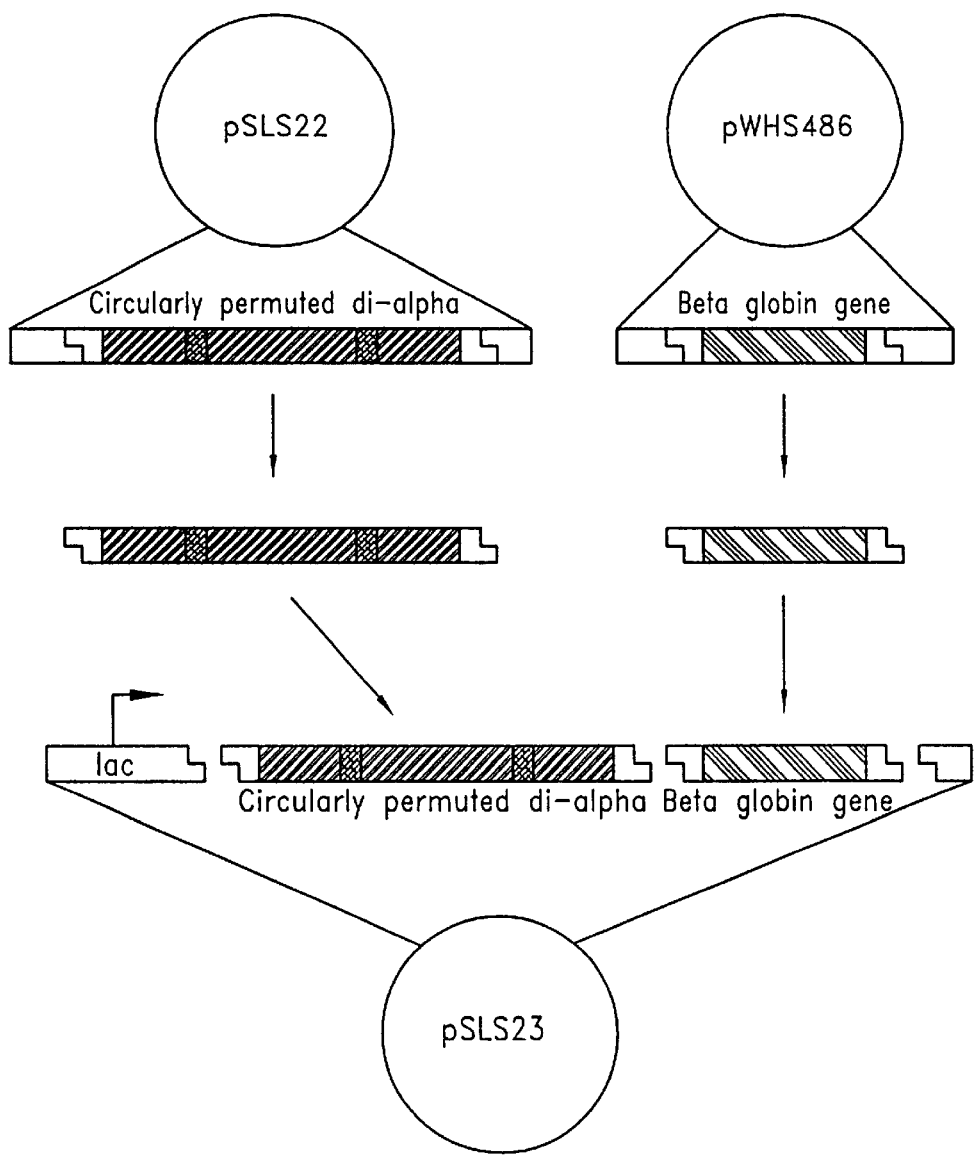
FIG. 8 shows schematic representation of the ligation procedure used to generate pSLS23.

A single operon was then created consisting of both circularly permuted di-alpha and desVal beta globin gene under the control of a single lac promoter. The circularly permuted di-alpha globin gene, isolated by digestion of pSLS22 with XbaI and PstI, and the beta globin gene, isolated by digestion of pWHS486 with PstI and HindIII, were ligated into pUC18 digested with XbaI and HindIII to generate pSLS23 (FIG. 8).

Construction of the tetra-alpha gene fusion

Figure 10:
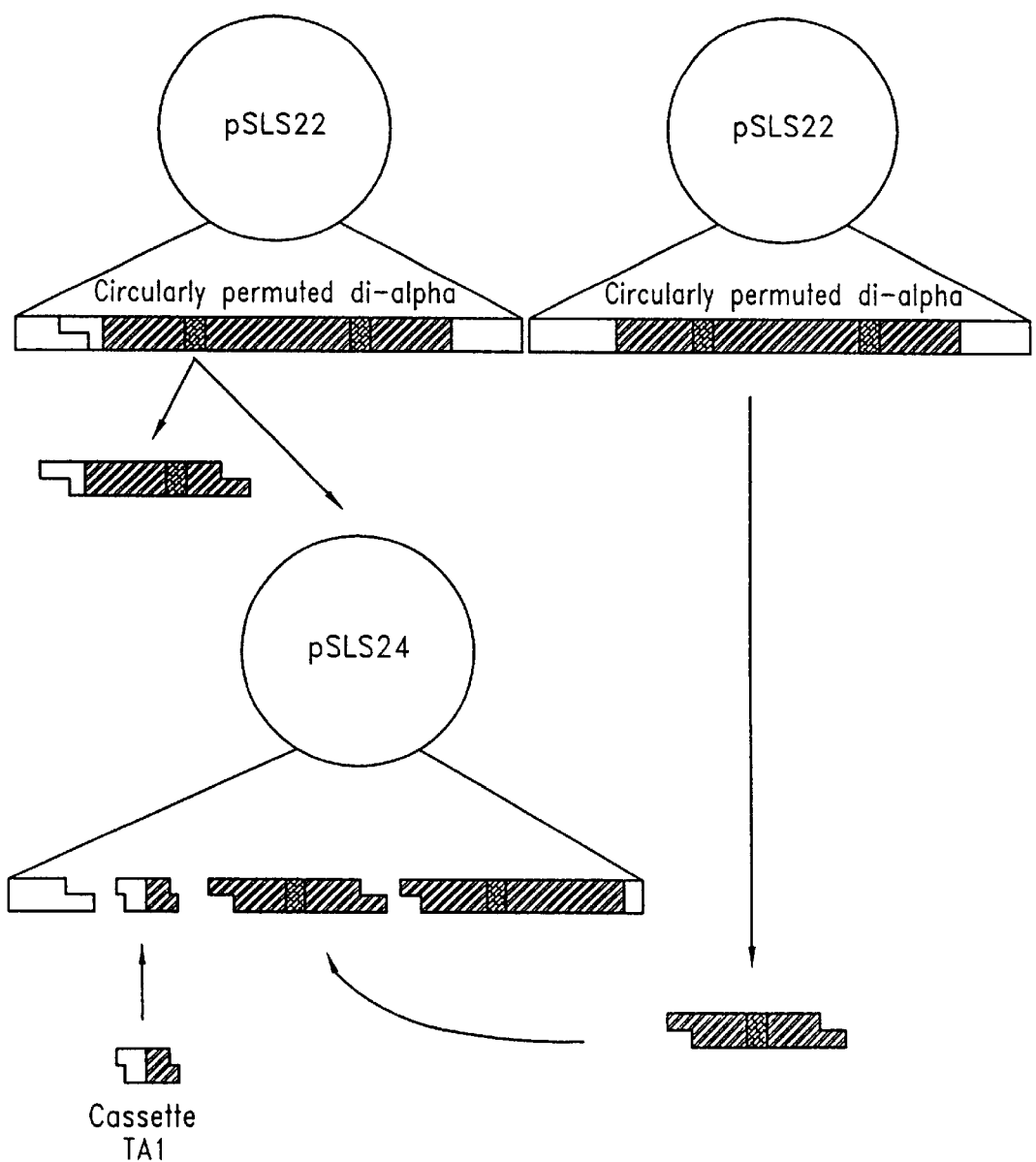
FIG. 10 provides a schematic representation of the ligation procedure used to generate pSLS24.
Figure 11:
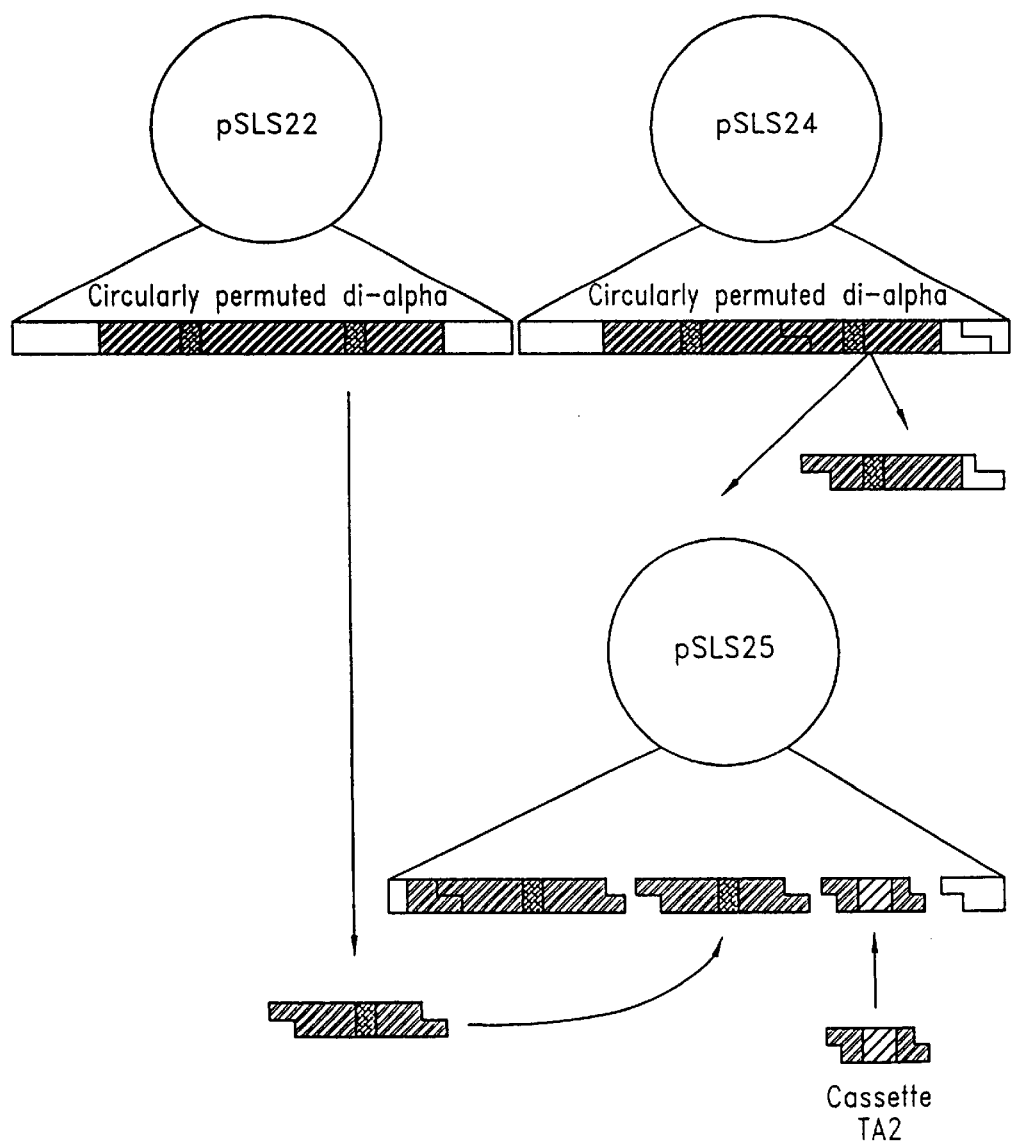
FIG. 11 provides a schematic representation of the ligation procedure used to generate pSLS25.

Two circularly permuted di-alpha genes were fused with a linking region to create a tetra-alpha gene. This construct when expressed with beta globin genes forms a functionally octomeric globin consisting of 1 tetra-alpha globin and 4 beta globin genes. Three ligation steps and 2 cassettes were required for the creation of the tetra-alpha, beta globin gene operon. Cassettes used in the construction TA1 and TA2 are shown in FIG. 9. First, the StyI/BamHI fragment of pSLS22 and cassette TA1 was ligated into pSLS22 digested with XbaI and BamHI in order to destroy the StyI site of pSLS22, generating pSLS24(FIG. 10). Secondly, a 400 b.p. BamHI/XhoI fragment of pSLS22 and cassette TA2 was ligated into pSLS24 digested with BamHI and PstI generating pSLS25 (FIG. 11). Finally, the XbaI/StyI fragment of pSLS25, the StyI/PstI fragment of pSLS22, and the PstI/HindIII fragment of pWHS486 was ligated into pUC18 digested with XbaI and HindIII generating pSLS26(FIG. 12). The DNA sequence which was confirmed by sequencing is listed in FIG. 13. The gene product of this construct will be hereafter referred to as octomeric circularly permuted hemoglobin.

Construction of higher order circularly permuted alpha gene fusions

Figure 14:
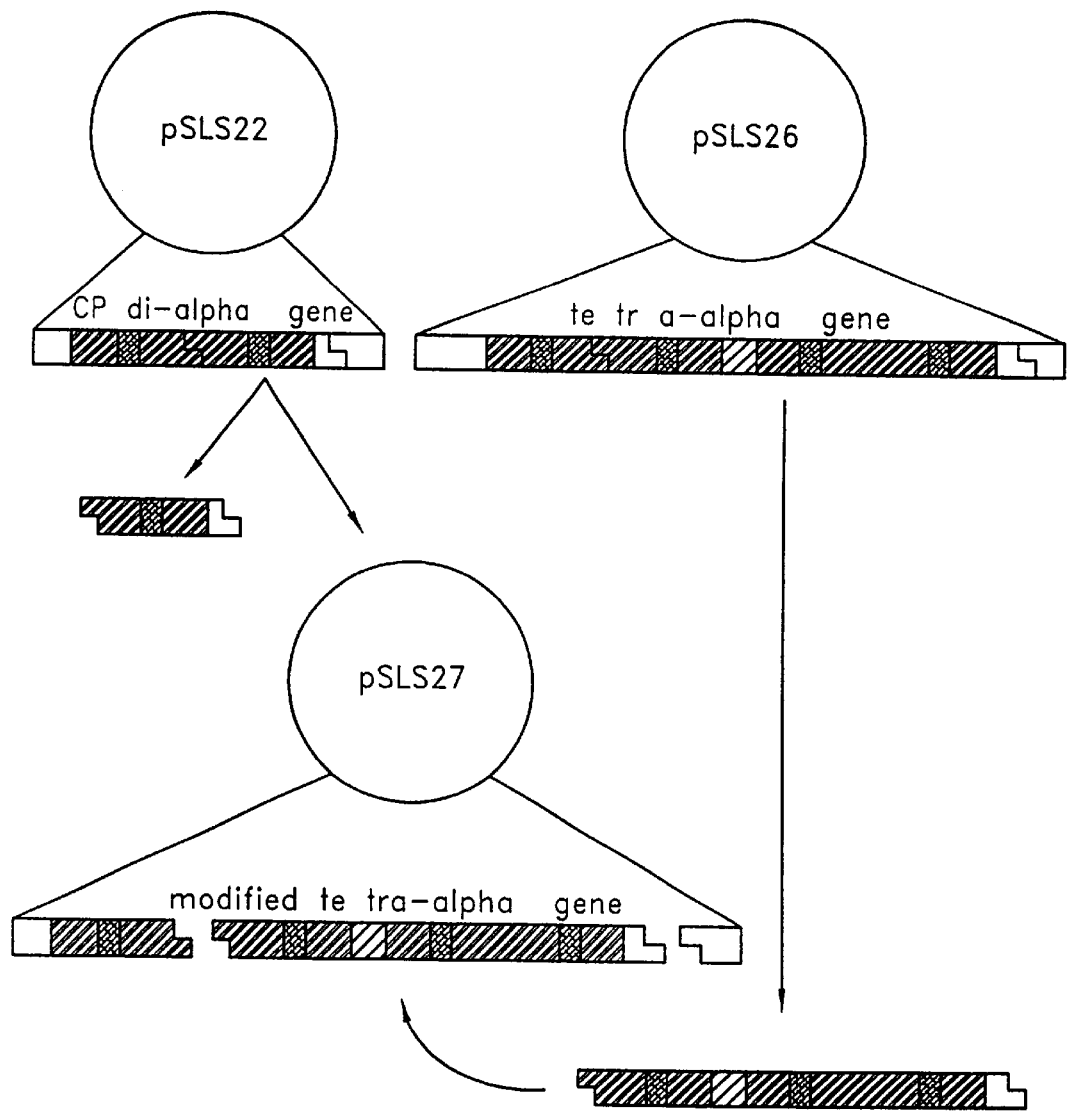
FIG. 14 provides a schematic representation of the ligation procedure used to generate pSLS27. The modified tetra-alpha gene contains slightly different restriction sites.
Figure 15:
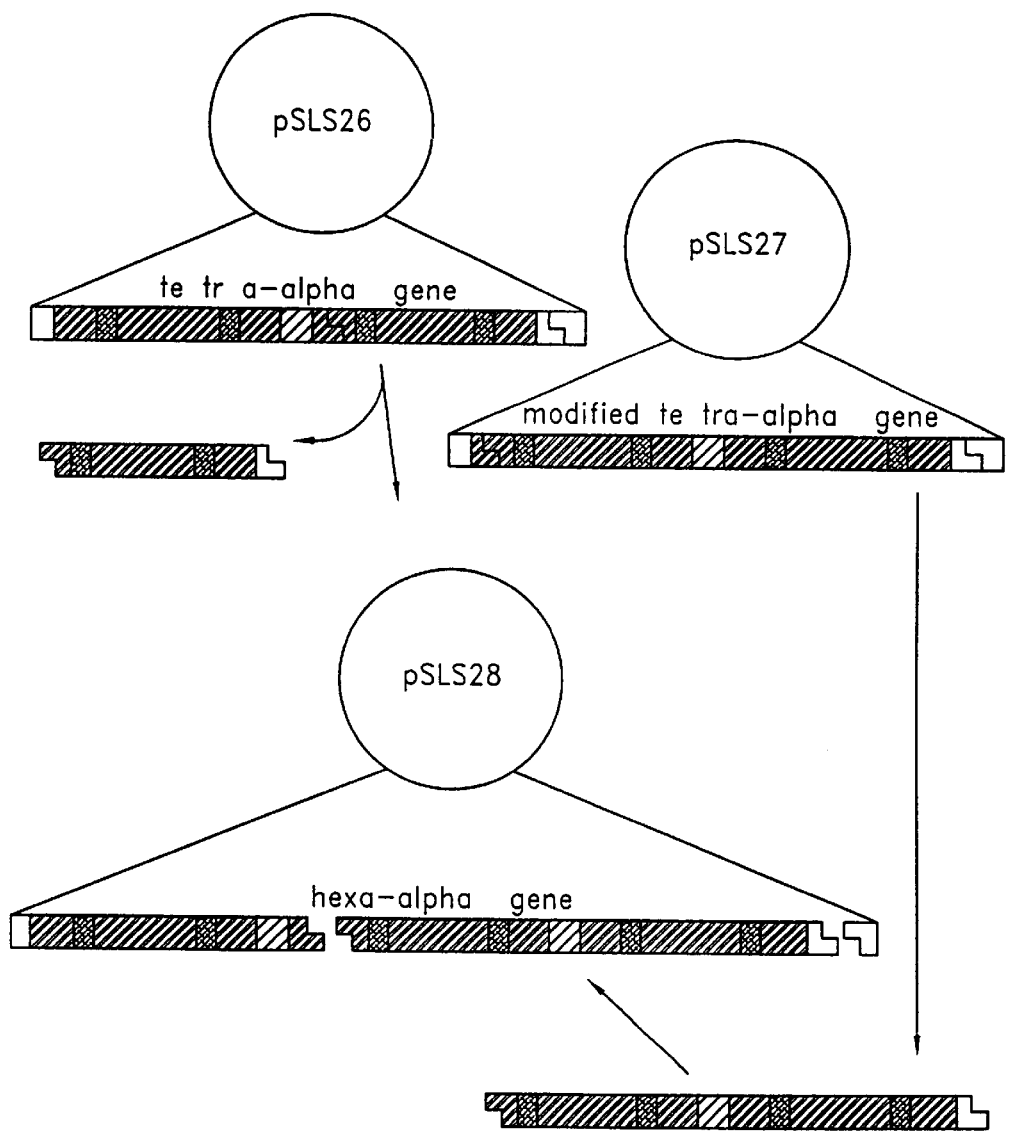
FIG. 15 provides a schematic representation of the ligation procedure used to generate pSLS28.

To generate 6 fused alpha chain genes, 2 ligation steps are required as well as the utilization of a partial digest. First, pSLS26 is digested fully with PstI. The resulting linear DNA vector is then partially digested with BamHI using 3 units of enzyme in a non-ideal buffer for 15 minutes. The 1350 b.p. fragment from this reaction is then isolated and ligated into pSLS22 digested with BamHI and PstI to generate pSLS27 (FIG. 14). Then pSLS27 is digested fully with PstI and partially digested, in a similar manner to the previous partial digest, with StyI. The 1500 b.p. fragment from this reaction is ligated into pSLS26 digested with StyI and PstI generating pSLS28(FIG. 15). In a similar manner any number of higher order alpha gene fusions can be created by the sequential ligation of circularly permuted dialpha segments from StyI partial and PstI digests of pSLS27 into progressively larger alpha gene fusion constructs.

Expression of genetically engineered, novel heme proteins

Plasmids pSLS23 and pSLS26 were transformed into competent E. coli DH5a cells. The cultures were grown in 1 L of 2XYT media (16 g tryptone, 10 g yeast extract, and 5 g NaCl/L)containing 200 µg/mL ampicillin and 0.5 mM d-aminolevulinic acid in 6 L shake flasks at 37° C. After 36–48 hours, the cells were harvested by centrifugation at 8000 g for 5 minutes and the cell paste was removed and stored frozen at –70° C.

Whole cell CO difference spectra

To assay protein expression, a Carbon Monoxide (CO) difference spectrum was taken of the E. coli cell cultures before protein purification. Cells were grown to stationary phase in the conditions described for protein expression above. A few grains of dithionite were added to 3–5 mL of the culture, and a baseline was recorded. CO was then bubbled through the culture and the spectrum was recorded on a Cary13 spectrophotometer.

Isolation and purification of protein

Cell paste was allowed to thaw over a stream of CO, and all buffers used during the lysis and purification procedure were saturated with CO. Thawed cells were resuspended in 5 times (w/v) 10 mM $NaH_2PO_4$, pH 6.0, 1 mM EDTA. Cells were lysed by 3–4 passes through a Stansted AO-116 cell disrupter. After cell lysis 80units/mL DNase and 8 units/mL RNase were added to the mixture and allowed to incubate at room temperature for 1 hr. The mixture was then centrifuged at 100,000 g in a Beckman L8-M ultracentrifuge. The supernatant was retained and the pH adjusted to 6.0 with 20 mM $NaH_2PO_4$. The supernatant was then loaded onto a carboxy methyl cellulose column (Whatman) equilibrated with 10 mM $NaH_2PO_4$, pH 6.0, 1 mM EDTA. The column was then washed with 4 column volumes of 10 mM $NaH_2PO_4$, pH 6.0, 1 mM EDTA, and finally eluted with a step gradient to 20 mM Tris-HCl, pH 7.0, 1 mM EDTA. The protein was then collected and concentrated using a PM-30 amicon membrane under nitrogen pressure. The concentrated protein was then flash frozen in liquid nitrogen and stored at –70° C. until used.

Mass spectrometry

Purified protein samples were run over a sephadex G-25 column to exchange the protein into water. Electrospray mass spectrometry was performed on the protein samples at the University of Illinois Mass Spectrometry Facility. The samples were diluted to a concentration of 10 pmol/µL into a 50:50 acetonitrile:water solution containing 0.1% formic acid for the experiments.

The experimentally measured masses of the circularly permuted hemoglobin (CpHb) and octameric circularly permuted hemoglobin (OHb) were compared with calculated values. The beta globins of each protein was measured to be 15900±2 Daltons. This is in good agreement with the calculated value of 15901.4 Daltons. The circularly permuted alpha globin construct of each protein are listed below. However, the calculated values are those expected for cleavage of the initial methionine residue. The values are in good agreement indicating that the proteins do not undergo any post-translational modification, except for initial methionine cleavage, in the bacterial host.

|  | Calculated | Measured |
|---|---|---|
| CpHb di-a | 30351.6 Da | 30352.6 ± 3.9 Da |
| OHb tetra-a | 60943.6 Da | 60940.4 ± 9.2 Da |

UV-Vos spectroscopy

Protein samples were reduced by the addition of a few grains of dithionite and exchanged into air saturated water. The oxygen bound spectrum was taken in a Hitachi U-3300 spectrophotometer. Then a few grains of dithionite were added to the sample and a deoxy spectrum was taken in a septa sealed cuvette. Finally, the CO bound form was generated by gently bubbling the sample with CO for 15 seconds, and a spectrum was recorded.

The spectrum for circularly permuted hemoglobin (CpHb) and octameric circularly permuted hemoglobin (OHb) were nearly identical to the spectrum of native hemoglobin. The absorbance maxima for each ligation state are listed below in nM.

| | ABSORBANCE MAXIMA | | | | | | | |
|---|---|---|---|---|---|---|---|---|
| | DEOXY Hb | | —OXY Hb | | | —CO Hb | | |
| Native Hb | 430 | 555 | 414 | 541 | 576 | 419 | 539 | 568 |
| CPHb | 429 | 555 | 414 | 540 | 577 | 419 | 538 | 568 |
| OHb | 429 | 554 | 414 | 541 | 576 | 419 | 539 | 568 |

SIS-PAGE

Polyacrylamide gel electrophoresis was performed on the purified protein samples. Each protein sample was boiled for 5 minutes in 10 mM tris-CHl, pH 8.0, 1 mM EDTA, 2.5% SDS, 5% b-mercaptoethanol, and 0.001% bromophenol-blue. 2 µL of the samples were loaded onto a 10–15% preformed gradient gel (Pharmacia). The gels were run using the Pharmacia PhastSystem for a total of 60 Volt hours at 250 Volts, 10.0 mA, 3.0 Watts, and 15° C. The gels were developed in the PhastSystem developing chamber using the fast coomassie staining technique.

Oxygen Equilibrium Measurements

Figure 17:
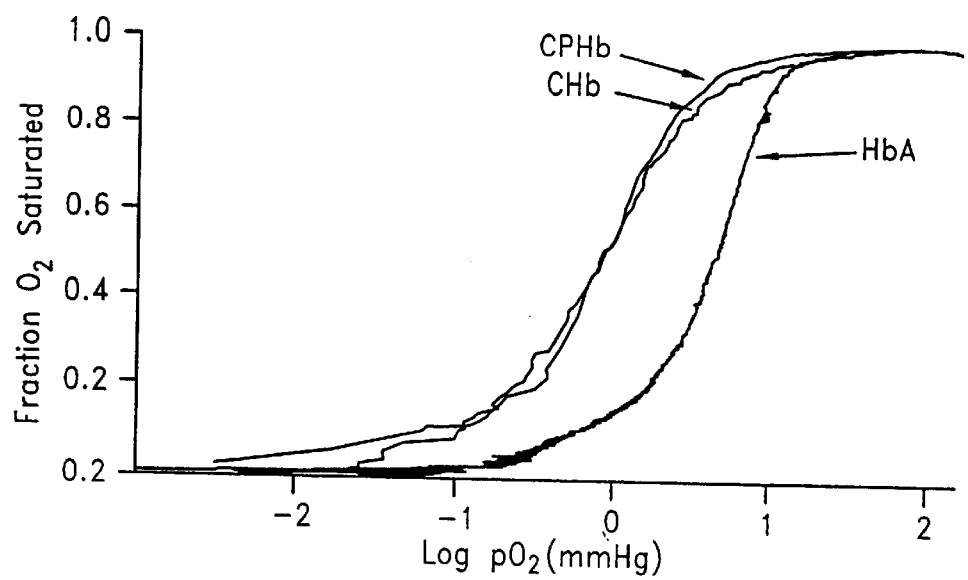
FIG. 17 shows equilibrium binding curves for native hemoglobin (HbA), circularly permuted hemoglobin (CPHb) and octameric hemoglobin (OHb).

The oxygen equilibrium measurements taken in a home-made hemeox analyzer (Ron Hernan, Ph.D. Thesis, University of Illinois at Urbana Champaign, 1994) are shown in FIG. 17. The equilibrium binding curves of native hemoglobin, circularly permuted hemoglobin (CpHb), and octameric circularly permuted hemoglobin (OHb) in 0.05 M Tris-HCl buffer at pH 7.4 with 0.1M [Cl⁻] were performed at 60 µM, 5 µM, and 5 µM in [heme] respectively. $P_{50}$ values and $n_{max}$ values were then calculated for each protein. A bohr effect was determined by measure $p_{50}$ values for each protein at pH 6.5 and 8.5 using 0.05 M Bis Tris with 0.1M [Cl⁻] and 0.05M Tris-CHl with 0.1M [Cl⁻] respectively. Finally each protein's response to allosteric effectors was measured with the addition of 0.1 mM IHP. Comparisons between the proteins are listed below and indicate that the circularly permuted hemoglobins cooperatively bind oxygen ($n_{max}$=2) and that they still respond to allosteric effectors (protons and IHP) in a similar manner to native hemoglobin.

|  | HbA$_o$ | CpHb | Octamer Hb |
|---|---|---|---|
| P$_{50}$ (mmHg) | 5.0 ± 0.2 | 0.9 ± 0.1 | 0.8 ± 0.1 |
| N$_{max}$ | 3.0 | 2.0 | 1.9 |
| Δlogp$_{50}$ ± 0.1 mM IHP | 0.9 | 0.7 | 0.7 |
| Bohr Effect | −0.5 | −0.3 | −0.4 |

Plasma Lifetime Measurements

Figure 18:
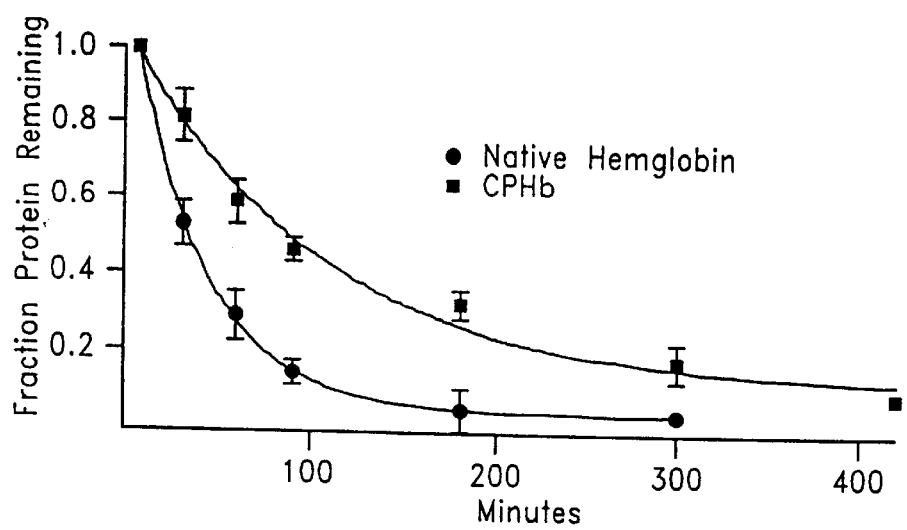
FIG. 18 shows the results of plasma lifetime measurement of HbA and CPHb.

Intravascular lifetime of the circularly permuted hemoglobin was measured and compared with the lifetime of cell free HbA. HbA was obtained from purification of freshly drawn blood as previously described (Ron Hernan, Ph.D. Thesis, University of Illinois at Urbana Champaign, 1994). Young adult Spaugue Dawley rats, weighing between 150 and 200 grams were used for the experiments. The protein samples were exchanged into a buffer solution consisting of 150 mM NaCl, 5 mM KCl, 2 mM NaPO$_4$, at pH 7.4 using a Sephadex G-25 column. The samples were then concentrated to approximately 1.5 mM in heme. 1 mL of this solution was filter sterilized and injected into each rat through a surgically placed jugular catheter. 200 μL blood samples were withdrawn from the same catheter at 5 minutes as a baseline and at successive time intervals. Plasma was separated from the erythrocytes by centrifugation, and the hemoglobin content was determined with the Plasma Hemoglobin Diagnostic Kit from Sigma. The measurements were then normalized to the 5 minute value and three experiments in three different rats were averaged for each protein. Exponential fits of the data are shown in FIG. 18, and the T$_{1/2}$ were calculated to be 30 and 90 minutes for HbA and circularly permuted hemoglobin respectively.

APPENDIX A

VARIANTS OF THE ALPHA CHAIN

| Residue | Substitution | Hb Name | Major Abnormal Property |
|---|---|---|---|
| 1 (NA1) | Val | | |
| 2 (NA2) | Leu→Arg | Chongqing | ↑ O$_2$ affinity; unstable |
| 3 (A1) | Ser | | |
| 4 (A1) | Pro | | |
| 5 (A3) | Ala→Asp | J-Toronto | |
|  | Ala→Pro | Karachi | |
| 6 (A4) | Asp→Ala | Sawara | ↑ O$_2$ affinity |
|  | Asp→Asn | Dunn | ↑ O$_2$ affinity |
|  | Asp→Val | Ferndown | ↑ O$_2$ affinity |
|  | Asp→Tyr | Woodville | ↑ O$_2$ affinity |
|  | Asp→Gly | Swan River | |
| 7 (A5) | Lys→Asn | Tatras | |
|  | Lys→Glu | Kurosaki | |
| 8 (A6) | Thr | | |
| 9 (A7) | Asn | | |
| 10 (A8) | Val | | |
| 11 (A9) | Lys→Glu | Anantharaj | |
|  | Lys→Gln | J-Wenchang-Wuming | |
|  | Lys→Asn | Albany-Suma | |
| 12 (A10) | Ala→Asp | J-Paris-I; J-Aljezur | |
| 13 (A11) | Ala | | |
| 14 (A12) | Trp→Arg | Evanston | ↑ O$_2$ affinity |
| 15 (A13) | Gly→Asp | I-Interlaken; J-Oxford; N-Cosenza | |
|  | Gly→Arg | Ottawa; Siam | |
| 16 (A14) | Lys→Glu | I; | |
|  |  | I-Philadelphia; I-Texas; I-Burlington; I-Skamania | |
|  | Lys→Asn | Beijing | |
|  | Lys→Met | Harbin | ↑ O$_2$ affinity; slightly unstable |
| 17 (A15) | Val | | |
| 18 (A16) | Gly→Arg | Handsworth | |
|  | Gly→Asp | Al-Ain Abu Dhabi | |
| 19 (AB1) | Ala→Asp | j-Kurosh | |
|  | Ala→Glu | Tashikuergan | |
| 20 (B1) | His→Tyr | Necker Enfants-Malades | |
|  | His→Gln | Le Lamentin | |
|  | His→Arg | Hobart | |
| 21 (B2) | Ala→Asp | J-Nyanza | |
|  | Ala→Pro | Fontainebleau | |
| 22 (B3) | Gly→Asp | J-Medellin | |
| 22 (B4) | Gly→Gln | Memphis | |
|  | Glu→Lys | Chad | |
|  | Glu→Val | G-Audhali | |
|  | Gly→Gly | Reims | slightly unstable |
|  | Glu→Asp | Lisbon | |
| 24 (B5) | Tyr→His | Luxembourg | unstable |
|  | Tyr→Cys | Ramona | |
| 25 (B6) | Gly | | |
| 26 (B7) | Ala→Glu | Shenyang | unstable |
| 27 (B8) | Glu→Gly | Fort Worth | |
|  | Glu→Val | Spanish Town | |
|  | Glu→Lys | Shuangfeng | unstable |
|  | Glu→Asp | Hekinan | |
| 28 (B9) | Ala | | |
| 29 (B10) | Leu→Pro | Agrinio | unstable; thalessemic |
| 30 (B11) | Glu→Lys | O-Padova | |
|  | Glu→Gln | G-Honolulu; G-Singapore; G-Chinese; G-Hong Kong | |
| 31 (B12) | Arg→Ser | Prato | unstable |
| 32 (B13) | Met | | |
| 33 (B14) | Phe | | |
| 34 (B15) | Leu→Arg | Queens; Ogi | |
| 35 (B16) | Ser | | |
| 36 (C1) | Phe | | |
| 37 (C2) | Pro→Arg | Bourmedes | |
| 38 (C3) | Thr | | |
| 39 (C4) | Thr | | |
| 40 (C5) | Lys→Glu | Kariya | ↑ O$_2$ affinity; unstable |
|  | Lys→Met | Kanagawa | ↑ O$_2$ affinity |
| 41 (C6) | Thr→Ser | Miyano | ↑ O$_2$ affinity |
| 42 (C7) | Tyr | | |
| 43 (CE1) | Phe→Val | Torino | unstable; ↑ O$_2$ affinity |
|  | Phe→Leu | Hirosaki | unstable |
| 44 (CE2) | Pro→Leu | Milledgeville | ↑ O$_2$ affinity |
|  | Pro→Arg | Kawachi | ↑ O$_2$ affinity |
| 45 (CE3) | His→Arg | Fort de France | ↑ O$_2$ affinity |
|  | His→Gln | Bari | |
|  | His→Asp | Poitiers | ↑ O$_2$ affinity |
| 46 (CE4) | Phe | | |
| 47 (CE5) | Asp→Gly | Kokura; Umi Michigan-I and -II; Yukuhashi-II; L-Gaslini; Tagawa-II; Beilinson; Mugino | unstable; ↑ O$_2$ affinity |
|  | Asp→His | Hasharon; Sinai; Sealy; | unstable |

-continued
VARIANTS OF THE ALPHA CHAIN

| Residue | Substitution | Hb Name | Major Abnormal Property |
|---|---|---|---|
| | | L-Ferrara | |
| | Asp→Asn | Arya | slightly unstable |
| | Asp→Ala | Cordele | unstable |
| | Asp→Tyr | Kurdistan | thalassemic |
| 48 (CE6) | Leu→Arg | Montgomery | |
| 49 (CE7) | Ser→Arg | Savaria | |
| 50 (CE8) | His→Asp | J-Sardegna | |
| | His→Arg | Aichia | slightly unstable |
| 51 (CE9) | Gly→Asp | J-Abidjan | |
| | Gly→Arg | Russ | |
| 52 (EI) | Ser | | |
| 53 (E2) | Ala→Asp | J-Rovigo | unstable |
| 54 (E3) | Gln→Arg | Shimonoseki; Hikoshima | |
| | Gln→Glu | Mexico; J; J-Paris-II; Uppsala | |
| 55 (E4) | Val | | |
| 56 (E5) | Lys→Thr | Thailand | |
| | Lys→Glu | Shaare Zedek | |
| | Lys→Asn | Belliard | |
| | Lys→Arg | Port Huron | |
| 57 (E6) | Gly→Arg | L-Persian Gulf | |
| | Gly→Asp | J-Norfold; Kagoshima; Nishik-I; II; III | |
| 58 (E7) | His→Tyr | M-Boston; M-Osaka; Gothenburg; M-Kiskunhalas | ↑ O$_2$ affinity |
| 59 (E8) | Gly→Val | Tottori | unstable |
| | Gly→Asp | Adana | unstable |
| 60 (E9) | Lys→Asn | Zambia | |
| | Lys→Glu | Dagestan | |
| 61 (E10) | Lys→Asn | J-Buda | |
| | Lys→Thr | J-Anatolia | |
| 62 (E11) | Val→Met | Evans | unstable |
| 63 (E12) | Ala→Asp | Pontoise; J-Pontoise | unstable |
| 64 (E13) | Asp→Asn | G-Waimanalo; Aida | |
| | Asp→His | Q-India | |
| | Asp→Tyr | Perspolis | |
| | Asp→Gly | Guangzhou-Hangzhou | |
| 64 (E14) | Ala | | |
| 66 (E15) | Leu | | |
| 67 (E16) | Thr | | |
| 68 (E17) | Asn→Asp | Ube-2 | |
| | Asn→Lys | G-Philadelphia; G-Knoxville-I; Stanleyville-I; D-Washington; D-St. Louis; G-Bristol; G-Azakuoli; D-Baltimore | |
| 69 (E18) | Ala | | |
| 70 (E19) | Val | | |
| 71 (E20) | Ala→Glu | J-Habana | |
| | Ala→Val | Ozieri | |
| 72 (EF1) | His→Arg | Daneshgah-Tehran | |
| 73 (EF2) | Val | | |
| 101 (G8) | Leu | | |
| 102 (G9) | Ser→Arg | Manitoba | slightly unstable |
| 103 (G10) | His→Arg | Contaldo | unstable |
| 104 (G11) | Cys→Tyr | Sallanches | |
| 105 (G12) | Leu | | |
| 106 (G13) | Leu | | |
| 107 (G14) | Val | | |
| 108 (G15) | Thr | | |
| 109 (G16) | Leu→Arg | Suan-Dok | unstable |
| 110 (G17) | Ala→Asp | Petah Tikva | unstable |
| | Ala→Thr | Tonosho | slightly unstable; ↑ dissociation; ↑ O$_2$ affinity |
| 111 (G18) | Ala→Val | Anamosa | |
| 112 (G19) | His→ | Hopkins-II | unstable; ↑ O$_2$ affinity |
| | His→Arg | Strumica; Serbia | |
| 113 (GH1) | Leu→His | Twin Peaks | |
| 114 (GH2) | Pro→Arg | Chiapas | |
| | Pro→Leu | Nouakchott | ↑ hydrophobicity |
| | Pro→Ser | Melusine | |
| 115 (GH3) | Ala→Asp | J-Tongariki | |
| 116 (GH4) | Glu→Lys | O-Indonesia; Buginese-X; Oliviere | |
| | Glu→Ala | Ube-4 | |
| | Glu→Gln | Oleander | |
| 117 (GH5) | Phe | | |
| 118 (H1) | Thr | | |
| 119 (H2) | Pro | | |
| 120 (H3) | Ala→Glu | J-Meerut; J-Birmingham | |
| 121 (H4) | Val→Met | Owari | |
| 122 (H5) | His→Gln | Westmead | |
| 123 (H6) | Ala→Ser | Mulhacen | |
| 124 (H7) | Ser | | |
| 125 (H8) | Leu→Pro | Quong Sze | |
| 126 (H9) | Asp→Asn | Tarrant | ↑ O$_2$ affinity |
| | Asp→His | Sassari | |
| | Asp→Val | Fukutomi | ↑ O$_2$ affinity |
| | Asp→Tyr | Montefiore | ↑ O$_2$ affinity |
| 127 (H10) | Lys→Thr | St. Claude | |
| | Lys→Asn | Jackson | |
| 128 (H11) | Phe | | |
| 129 (H12) | Leu→Pro | α-Tunis | unstable; thalessemic |
| 130 (H13) | Ala→Pro | Sun Prairie | unstable |
| | Ala→Asp | Yuda | ↑ O$_2$ affinity |
| 131 (HI4) | Ser→Pro | Questembert | highly unstable |
| 132 (H15) | Val→Gly | Caen | unstable |
| 133 (H16) | Ser→Arg | Val de Marne; Footscray | sl. ↑ O$_2$ affinity |
| 134 (H17) | Thr | | |
| 135 (H18) | Val→Glu | Pavie | |
| 136 (H19) | Leu→Pro | Bibba | unstable; ↑ dissociation |
| | Leu→Arg | Toyama | unstable |
| | Leu→Met | Chicago | |
| 137 (H20) | Thr | | |
| 138 (H21) | Ser→Pro | Attleboro | ↑ O$_2$ affinity |
| 139 (HC1) | Lys→Thr | Tokoname | ↑ O$_2$ affinity |
| | Lys→Glu | Hanamaki | ↑ O$_2$ affinity |
| 140 (HC2) | Tyr→His | Ethiopia; Rouen | ↑ O$_2$ affinity ↑ O$_2$ affinity |
| 141 (HC3) | Arg→Pro | Singapore | |
| | Arg→His | Suresnes | ↑ O$_2$ affinity |
| | Arg→Ser | J-Cubujuqui | ↑ O$_2$ affinity |
| | Arg→Leu | Legnano | ↑ O$_2$ affinity |
| | Arg→Gly | J-Camaguey | |
| | Arg→Cys | Nunobiki | ↑ O$_2$ affinity |

VARIANTS OF THE BETA CHAIN

| Residue | Substitution | Hb Name | Major Abnormal Property |
|---|---|---|---|
| 1 (NA1) | Val→Ac-Ala | Raleigh | ↓ O$_2$ affinity; ↓ dissociation |
| 2 (NA2) | His→Arg | Deer Lodge | ↑ O$_2$ affinity |
| | His→Gln | Okayama | ↑ O$_2$ affinity |
| | His→Tyr | Fukuoka | |

-continued

VARIANTS OF THE BETA CHAIN

| Residue | Substitution | Hb Name | Major Abnormal Property |
|---|---|---|---|
| 3 (NA3) | His→Leu<br>Leu | Graz | |
| 4 (A1) | Thr | | |
| 5 (A2) | Pro→Arg | Warwickshire | |
| | Pro→Ser | Tyne | |
| 6 (A3) | Glu→Val | S | |
| | Glu→Lys | C | |
| | Glu→Ala | G-Makassar | |
| | Glu→Gln | Machida | |
| 7 (A4) | Glu→Gly | G-San José | mildly unstable |
| | Glu→Lys | Siriraj | |
| 8 (A5) | Lys→Thr | Rio Grande | |
| | Lys→Gln | J-Lube | |
| | Lys→Glu | N-Timone | |
| 9 (A6) | Ser→Cys | Port Alegre | polymerization;<br>↑ $O_2$ affinity;<br>↓ heme-heme |
| 10 (A7) | Ala→Asp | Ankara | |
| 11 (A8) | Val→Ile | Hamilton | |
| | Val→Asp | Windsor | unstable |
| | Val→Phe | Washtenaw | ↓ $O_2$ affinity |
| 12 (A9) | Thr | | |
| 13 (A10) | Ala→Asp | J-Lens | |
| 14 (A11) | Leu→Arg | Sogn | unstable |
| | Leu→Pro | Saki | unstable |
| 15 (A12) | Trp→Arg | Belfast | unstable;<br>↑ $O_2$ affinity |
| | Trp→Gly | Randwick | unstable |
| 16 (A13) | Gly→Asp | J-Baltimore;<br>J-Trinidad; J-Ireland;<br>N-New Haven;<br>J-Georgia | |
| | Gly→Arg | D-Bushman | |
| 17 (A14) | Lys→Glu | Nagasaki | |
| | Lys→Asn | J-Amiens | |
| | Lys→Gln | Nikosia | |
| 18 (A15) | Val→Met | Baden | slightly unstable |
| | Val→Gly | Sinai-Baltimore | Slightly unstable |
| 19 (B1) | Asn→Lys | D-Ouled Rabah | |
| | Asn→Asp | Alamo | |
| | Asn→Ser | Malay | |
| 20 (B2) | Val→Met | Olympia | ↑ $O_2$ affinity |
| | Val→Glu | Trollhattan | ↑ $O_2$ affinity |
| 21 (B3) | Asp→Tyr | Yusa | |
| | Asp→Gly | Connecticut | ↑ $O_2$ affinity |
| | Asp→Asn | Cocody | |
| | Asp→His | Kariskoga | |
| 22 (B4) | Glu→Lys | E-Saskatoon | unstable |
| | Glu→Gly | G-Taipei | |
| | Glu→Ala | G-Coushatta;<br>G-Saskatoon;<br>Hsin Chu;<br>G-Taegu | |
| | Glu→Gln | D-Iran | |
| | Glu→Val | D-Granada | |
| 23 (B5) | Val→Asp | Strasbourg | ↑ $O_2$ affinity |
| | Val→Gly | Miyashiro | unstable;<br>↑ $O_2$ affinity |
| | Val→Phe | Palmerston North | ↑ $O_2$ affinity;<br>unstable |
| 24 (B6) | Gly→Arg | Riverdale-Bronx | unstable;<br>↑ $O_2$ affinity |
| | Gly→Val | Savanna | unstable |
| | Gly→Asp | Moscva | unstable;<br>↓ $O_2$ affinity |
| 25 (B7) | Gly→Arg | G-Taiwan Ami | |
| | Gly→Asp | J-Auckland | Unstable;<br>↓ $O_2$ affinity |
| 26 (B8) | Glu→Lys | E | |
| | Glu→Val | Henri Mondor | slightly unstable |
| 27 (B9) | Ala→Asp | Volga;<br>Drenthe | unstable |
| | Ala→Ser | Knossos | |
| | Ala→Val | Grange-Blanche | ↑ $O_2$ affinity |
| 28 (B10) | Leu→Gln | St. Louis | unstable; ferri-Hb; ↑ $O_2$ affinity |
| | Leu→Pro | Genova;<br>Hyogo | unstable;<br>↑ $O_2$ affinity |
| | Leu→Arg | Chesterfield | unstable;<br>thalassemic |
| 29 (B11) | Gly→Asp | Lufkin | unstable |
| 30 (B12) | Arg→Ser | Tacoma | unstable; ↓ Bohr and heme-heme |
| | Arg→Thr | Monroe;<br>Kairouan | |
| 31 (B13) | Leu→Pro | Yokohama | unstable |
| | Leu→Arg | Hakkari | severely unstable |
| 32 (B14) | Leu→Pro | Perth;<br>Abraham Lincoln;<br>Kobe | unstable |
| | Leu→Arg | Castilla | unstable |
| | Leu→Val | Muscat | slightly unstable |
| | Leu→Gln | Medicine Lake | |
| 33 (B15) | Val | | |
| 34 (B16) | Val→Phe | Pitie-Salpetriere | ↑ $O_2$ affinity |
| 35 (C1) | Tyr→Phe | Philly | unstable;<br>↑ $O_2$ affinity |
| 36 (C2) | Pro→Thr | Linköping;<br>Meilahti;<br>Finlandia | unstable;<br>↑ $O_2$ affinity<br>↑ $O_2$ affinity |
| | Pro→Ser | North Chicago | ↑ $O_2$ affinity |
| | Pro→Arg | Sunnybrook | |
| 37 (C3) | Trp→Ser | Hirose | ↑ $O_2$ affinity;<br>↑ dissociation |
| | Trp→Arg | Rothschild | ↓ $O_2$ affinity |
| | Trp→Gly | Howick | ↑ $O_2$ affinity |
| 38 (C4) | Thr→Pro | Hazebrouck | unstable;<br>↓ $O_2$ affinity |
| 39 (C5) | Gln→Lys | Alabama | |
| | Gln→Glu | Vaasa | unstable |
| | Gln→Arg | Tianshui | |
| 40 (C6) | Arg→Lys | Athens-GA;<br>Waco | ↑ $O_2$ affinity |
| | Arg→Ser | Austin | ↑ $O_2$ affinity;<br>↑ dissociation |
| 41 (C7) | Phe→Tyr | Mequon | |
| | Phe→Ser | Denver | ↓ $O_2$ affinity;<br>cyanotic |
| 42 (CD1) | Phe→Ser | Hammersmith;<br>Chiba | unstable;<br>↓ $O_2$ affinity |
| | Phe→Leu | Louisville;<br>Bucuresti | unstable;<br>↓ $O_2$ affinity |
| | Phe→Val | Sendagi;<br>Warsaw | unstable;<br>↓ $O_2$ affinity |
| 43 (CD2) | Glu→Ala | G-Galveston;<br>G-Port Arthur;<br>G-Texas | |
| | Glu→Gln | Hoshida;<br>Chaya | |
| 44 (CD3) | Ser→Cys | Mississippi | |
| 45 (CD4) | Phe→Ser | Cheverly | unstable;<br>↓ $O_2$ affinity;<br>↓ Bohr effect |
| | Phe→Cys | Arta | unstable;<br>↓ $O_2$ affinity;<br>thalassemic |
| 46 (CD5) | Gly→Glu | K-Ibadan | |
| | Gly→Arg | Gainesville-GA | |
| 47 (CD6) | Asp→Asn | G-Copenhagen | |
| | Asp→Gly | Gavello | |
| | Asp→Ala | Avicenna | |
| | Asp→Tyr | Maputo | |
| 48 (CD7) | Leu→Arg | Okaloosa | unstable;<br>↓ $O_2$ affinity |

VARIANTS OF THE BETA CHAIN

| Residue | Substitution | Hb Name | Major Abnormal Property |
|---|---|---|---|
| 49 (CD8) | Leu→Pro | Bab-Saadoun | slightly unstable |
|  | Ser→Phe | Las Palmas | slightly unstable |
| 50 (D1) | Thr→Lys | Edmonton |  |
| 51 (D2) | Pro→Arg | Willamette | ↑ $O_2$ affinity; unstable |
| 52 (D3) | Asp→Asn | Osu Christiansborg |  |
|  | Asp→Ala | Ocho Rios |  |
|  | Asp→His | Summer Hill |  |
| 53 (D4) | Ala |  |  |
| 54 (D5) | Val→Asp | Jacksonville | Unstable; ↑ $O_2$ affinity |
| 55 (D6) | Met→Lys | Matera | unstable |
| 56 (D7) | Gly→Asp | J-Bangkok; J-Meinung; J-Korat; J-Manado |  |
|  | Gly→Arg | Hamadan |  |
| 57 (E1) | Asn→Lys | G-Ferrara | unstable |
|  | Asn→Asp | J-Dalos |  |
| 58 (E2) | Pro→Arg | Dhofar; Yukuhashi |  |
| 59 (E3) | Lys→Glu | I = High Wycombe |  |
|  | Lys→Thr | J-Kaohsiung; J-Honolulu |  |
|  | Lys→Asn | J-Lome | ↑ autooxidation |
| 60 (E4) | Val→Leu | Yatsushiro |  |
|  | Val→Ala | Collingwood | unstable |
|  | Val→glu | Cagliari | unstable; thalassemic |
| 61 (E5) | Lys→Glu | N-Seattle |  |
|  | Lys→Asn | Hikari |  |
|  | Lys→Met | Bologna | ↓ $O_2$ affinity |
| 62 (E6) | Ala→Pro | Duarte | unstable; ↑ $O_2$ affinity |
| 63 (E7) | His→Arg | Zürich | unstable; ↑ $O_2$ affinity |
|  | His→Tyr | M-Saskatoon; M-Emory; M-Kurume; M-Hida; M-Radom; M-Arhus; M-Chicago; Leipzig; Horlein-Weber; Novi Sad; M-Erlangen | ferri-Hb; ↑ $O_2$ affinity |
|  | His→Pro | Bicetre | unstable; ↑ autooxidizing |
| 64 (E8) | Gly→Asp | J-Calabria; J-Bari; J-Cosenza | unstable; ↑ $O_2$ affinity |
| 65 (E9) | Lys→Asn | J-Sicilia |  |
|  | Lys→Gln | J-Cairo | ↓ $O_2$ affinity; ↑ autooxidation |
|  | Lys→Met | J-Antakya |  |
| 66 (E10) | Lys→Glu | I-Toulouse | unstable; Ferri-Hb |
|  | Lys→Thr | Chico | ↓ $O_2$ affinity |
| 67 (E11) | Val→Asp | Bristol | unstable; ↓ $O_2$ affinity |
|  | Val→Glu | M-Milwaykee-I | ferri-Hb; ↓ $O_2$ affinity |
|  | Val→Ala | Sydney | unstable |
|  | Val→Met | Alesha | unstable |
|  | Val→Gly | Manukau | unstable; hemolytic anemia; thalassemic |
| 68 (E12) | Leu→Pro | Mizuho | unstable |
|  | Leu→His | Brisbane; Great Lakes | ↑ $O_2$ affinity; (?) unstable |
| 69 (E13) | Gly→Asp | J-Cambridge; J-Rambam |  |
|  | Gly→Ser | City of Hope |  |
|  | Gly→Arg | Kenitra |  |
| 70 (E14) | Ala→Asp | Seattle | ↓ $O_2$ affinity; unstable |
| 71 (E15) | Phe→Ser | Christchurch | unstable |
| 72 (E16) | Ser→Arg | Headington | ↑ $O_2$ affinity; thalassemic |
| 73 (E17) | Asp→Tyr | Vancouver | ↓ $O_2$ affinity |
|  | Asp→Asn | Korle-Bu; G-Accra | ↓ $O_2$ affinity |
|  | Asp→Val | Mobile | ↓ $O_2$ affinity |
|  | Asp→Gly | Tilburg | ↓ $O_2$ affinity |
| 74 (E18) | Gly→Val | Bushwick | unstable |
|  | Gly→Asp | Shepherds Bush | unstable; ↑ $O_2$ affinity |
|  | Gly→Arg | Aalborg | unstable |
| 75 (E19) | Leu→Pro | Atlanta | unstable |
|  | Leu→Arg | Pasadena | unstable; ↑ $O_2$ affinity |
| 76 (E20) | Ala→Asp | J-Chicago |  |
|  | Ala→Pro | Calais | ↓ $O_2$ affinity; ↑ met-Hb formation |
| 77 (EF1) | His→Asp | J-Iran |  |
|  | His→Tyr | Fukuyama |  |
| 78 (EF2) | Leu→Arg | Quin-Hai |  |
| 79 (EF3) | Asp→Gly | G-His-Tsou | ↑ $O_2$ affinity |
|  | Asp→Tyr | Tampa |  |
|  | Asp→His | Tigraye | ↑ $O_2$ affinity |
|  | Asp→Asn | Yaizu |  |
| 80 (EF4) | Asn→Lys | G-Szuhu; Gifu |  |
| 81 (EF5) | Leu→Arg | Baylor | unstable; ↑ $O_2$ affinity |
|  | Leu→His | La Roche-Sur-Yon | unstable; ↑ $O_2$ affinity |
|  | (β Asn partially deaminated) |  |  |
| 82 (EF6) | Lys→Asn→Asp | Providence | ↓ $O_2$ affinity |
|  | Lys→Thr | Rahere | ↑ $O_2$ affinity |
|  | Lys→Met | Helsinki | ↑ $O_2$ affinity |
| 83 (EF7) | Gly→Cys | Ta-Li | slightly unstable; polymerization |
|  | Gly→Asp | Pyrgos; Misunami | slightly ↓ $O_2$ affinity |
|  | Gly→Arg | Muskegon |  |
| 84 (EF8) | Thr→Ile | Kofu |  |
| 85 (F1) | Phe→Ser | Buenos Aires; Bryn Mawr | unstable; ↑ $O_2$ affinity |
| 86 (F2) | Ala→Asp | Olomouc | ↑ $O_2$ affinity |
| 87 (F3) | Thr→Lys | D-Ibadan |  |
|  | Thr→Ile | Quebec-Chori |  |
|  | Thr→Pro | Valletta |  |
| 88 (F4) | Leu→Arg | Borks | unstable |
|  | Leu→Pro | Santa Ana | unstable |
| 89 (F5) | Ser→Asn | Creteil | ↑ $O_2$ affinity |
|  | Ser→Arg | Vanderbilt | ↑ $O_2$ affinity |
|  | Ser→Thr | Villaverde | ↑ $O_2$ affinity |
| 90 (F6) | Glu→Lys | Agenogi | ↓ $O_2$ affinity |
|  | Glu→Gly | Roseau-Point à Pitre | ↓ $O_2$ affinity; unstable |
|  | Glu→Asp | Pierre-Bénite | ↑ $O_2$ affinity |
| 91 (F7) | Leu→Pro | Sabine | unstable |
|  | Leu→Arg | Caribbean | unstable; ↓ $O_2$ affinity |
| 92 (F8) | His→Tyr | M-Hyde Park; M-Akita | ferri-Hb |
|  | His→Gln | St. Etienne; Istanbul | unstable; ↑ $O_2$ affinity ↑ dissociation |
|  | His→Asp | J-Altgeld Gardens | unstable |
|  | His→Pro | Newcastle | unstable |

VARIANTS OF THE BETA CHAIN

| Residue | Substitution | Hb Name | Major Abnormal Property |
|---|---|---|---|
| | His→Arg | Mozhaisk | unstable; ↑ O₂ affinity |
| | His→Asn→Asp | Redondo; Isehara | unstable |
| 93 (F9) | Cys→Arg | Okazaki | ↑ O₂ affinity; unstable |
| 94 (FG1) | Asp→His | Barcelona | ↑ O₂ affinity |
| | Asp→Asn | Bunbury | ↑ O₂ affinity |
| | Asp→Gly | Chandigarh | |
| 95 (FG2) | Lys→Glu | N-Baltimore; Hopkins-I; Jenkins; N-Memphis; Kenwood | |
| | Lys→Met | J-Cordoba | |
| | Lys→Asn | Detroit | |
| 96 (FG3) | Leu→Val | Regina | ↑ O₂ affinity |
| 97 (FG4) | His→Gln | Malmö | ↑ O₂ affinity |
| | His→Leu | Wood | ↑ O₂ affinity |
| | His→Pro | Nagoya | unstable; ↑ O₂ affinity |
| | His→Tyr | Moriguchi | |
| 98 (FG5) | Val→Met | Köln; San Francisco (Pacific); Ube-I | unstable; ↑ O₂ affinity |
| | Val→Gly | Nottingham | unstable; ↑ O₂ affinity |
| | Val→Ala | Djelfa | unstable; ↑ O₂ affinity |
| | Val→Glu | Mainz | unstable |
| 99 (G1) | Asp→Asn | Kempsey | ↑ O₂ affinity |
| | Asp→His | Yakima | ↑ O₂ affinity |
| | Asp→Ala | Radcliffe | ↑ O₂ affinity |
| | Asp→Tyr | Ypsilanti | ↑ O₂ affinity |
| | Asp→Gly | Hotel-Dieu | ↑ O₂ affinity |
| | Asp→Val | Chemilly | ↑ O₂ affinity |
| | Asp→Glu | Coimbra; Ingelheim | ↑ O₂ affinity; polycythemia |
| 100 (G2) | Pr→Leu | Brigham | ↑ O₂ affinity |
| | Pro→Arg | New Mexico | |
| 101 (G3) | Glu→Lys | British Columbia | ↑ O₂ affinity |
| | Glu→Gln | Rush | unstable |
| | Glu→Gly | Alberta | ↑ O₂ affinity |
| | Gl→Asp | Potomac | ↑ O₂ affinity |
| 102 (G4) | Asn→Lys | Richmond | asymmetric hybrids |
| | Asn→Thr | Kansas | ↓ O₂ affinity; ↑ dissociation |
| | Asn→Ser | Beth Israel | unstable; ↓ O₂ affinity |
| | Asn→Tyr | Saint Mandé | ↓ O₂ affinity |
| 103 (G5) | Phe→Leu | Heathrow | ↑ O₂ affinity |
| | Phe→Ile | Saint Nazaire | ↑ O₂ affinity |
| 104 (G6) | Arg→Ser | Camperdown | slightly unstable |
| | Arg→Thr | Sherwood Forest | |
| 105 G7 | Leu→Phe | South Milwaukee | ↑ O₂ affinity |
| 106 (G8) | Leu→Pro | Southampton; Casper | unstable; ↑ O₂ affinity |
| | Leu→Gln | Tübingen | unstable; ↑ O₂ affinity |
| | Leu→Arg | Terre Haute | very unstable; formerly incorrectly identified as Hb Indianapolis [β112(G14) Cys→Arg]; see ref. 318 |
| 107 (G9) | Gly→Arg | Burke | unstable; ↓ O₂ affinity |
| 108 (G10) | Asn→Asp | Yoshizuka | ↓ O₂ affinity |
| | Asn→Lys | Presbyterian | ↓ O₂ affinity; unstable |
| 109 (G11) | Val→Met | San Diego | ↑ O₂ affinity |
| | Val→Leu | Johnstown | ↑ O₂ affinity |
| 110 (G12) | Lsu→Pro | Showa-Yakushiji | |
| 111 (G13) | Val→Phe | Peterborough | unstable; ↓ O₂ affinity |
| | Val→Ala | Stanmore | unstable; ↓ O₂ affinity |
| 112 (G14) | Cys→Arg | Indianapolis | (See also β106-Terre Haute) |
| | Cys→Tyr | Yahata | |
| 113 (G15) | Val→Glu | New York; Kaohslung | unstable; ↓ O₂ affinity |
| 114 (G16) | Leu→Met | Zengcheng | |
| | Leu→Pro | Durham-N.C. | unstable; thalessemic |
| 115 (G17) | Ala→Pro | Madrid | unstable |
| | Ala→Asp | Hradec Kralove (HK) | highly unstable; thalessemic |
| 116 (G18) | His→Gln | Hafnia | |
| 117 (G19) | His→Arg | P-Glaveston | |
| | His→Pro | Saitama | unstable |
| 118 (GH1) | Phe→Tyr | Minneapolis-Laos | |
| 119 (GH2) | Gly→Asp | Fannin-Lubbock | slightly unstable |
| | Gly→Val | Bougardirey-Mali | slightly unstable |
| | Gly→Ala | Iowa | |
| 120 (GH3) | Lys→Glu | Hijiyama | |
| | Lys→Asn | Riyadh; Karatsu | |
| | Lys→Gln | Takamatsu | |
| | Lys→Ile | Jianghua | |
| 121 (GH4) | Glu→Gln | D-Los Angeles; D-Punjab; D-North Carolina; D-Portugal; Oak Ridge; D-Chicago | ↓ O₂ affinity |
| | Glu→Lys | O-Arab; Egypt | |
| | Glu→Val | Beograd; D-Camperdown | |
| | Glu→Gly | St. Francis | |
| | Glu→Ala | D-Neath | |
| 122 (GH5) | Phe | | |
| 123 (H1) | Thr→Ile | Villejuif | |
| 124 (H2) | Pro→Arg | Khartoum | unstable |
| | Pro→Gln | Ty Gard | ↑ O₂ affinity |
| | Pro→Ser | β-Tunis | |
| 125 (H3) | Pro | | |
| 126 (H4) | Val→Glu | Hofu | unstable |
| | Val→Ala | Beirut | stable |
| | Val→Gly | Dhonburi; Neapolis | unstable; thalessemic unstable |
| 127 (H5) | Gln→Glu | Complutense | slightly unstable |
| | Gly→Lys | Brest | unstable |
| | Gln→Arg | Dieppe | unstable; anemic |
| 128 (H6) | Ala→Asp | J-Guantanamo | unstable |
| 129 (H7) | Ala→Asp | J-Taichung | |
| | Ala→Glu or Asp | K-Cameroon | |
| 129 (H7) | Ala→Pro | Crete | unstable; ↑ O₂ affinity |
| | Ala→Val | La Desirade | unstable; ↓ O₂ affinity |
| 130 (H8) | Tyr→Asp | Wien | unstable |
| | Tyr→Ser | Nevers | |
| 131 (H9) | Gln→Gln | Camden; Tokuchi; Motown | |
| | Gln→Lys | Shelby; formerly: Leslie; Deaconess | unstable |
| | Gln→Pro | Shanghai | unstable |

VARIANTS OF THE BETA CHAIN (continued)

| Residue | Substitution | Hb Name | Major Abnormal Property |
|---|---|---|---|
| | Gln→Arg | Sarrebourg | unstable |
| 132 (H10) | Lys→gln | K-Woolwich | |
| | Lys→Asn | Yamagata | slightly ↓ $O_2$ affinity |
| 133 (H11) | Val→Leu | Extremadura | |
| 134 (H12) | Val→Glu | North Shore; North Shore-Caracas | unstable |
| 135 (H13) | Ala→Pro | Altdorf | unstable; ↑ $O_2$ affinity |
| | Ala→Glu | Beckman | unstable; ↓ $O_2$ affinity |
| 136 (H14) | Gly→Asp | Hope | unstable; ↓ $O_2$ affinity |
| 137 (H15) | Val | | |
| 138 (H16) | Ala→Pro | Brockton | unstable |
| 139 (H17) | Asn→Asp | Geelong | unstable |
| | Asn→Lys | Hinsdale | |
| | Asn→Tyr | Aurora | ↑ $O_2$ affinity |
| 140 (H18) | Ala→Thr | Saint Jacques | ↑ $O_2$ affinity |
| | Ala→Asp | Himeji | unstable; ↓ $O_2$ affinity |
| | Ala→Val | Puttelange | ↑ $O_2$ affinity |
| 141 (H19) | Leu→Arg | Olmsted | Unstable |
| 142 (H20) | Ala→Asp | Ohio | ↑ $O_2$ affinity; reduced Bohr effect |
| | Ala→Pro | Toyoake | unstable; ↑ $O_2$ affinity |
| 143 (H21) | His→Arg | Abruzzo | ↑ $O_2$ affinity |
| | His→Gln | Little Rock | ↑ $O_2$ affinity |
| | Hi→Pro | Syracuse | ↑ $O_2$ affinity |
| | His→Asp | Rancho Mirage | |
| 144 (HC1) | Lys→Asn | Andrew-Minneapolis | ↑ $O_2$ affinity |
| | Lys→Glu | Mito | ↑ $O_2$ affinity |
| 145 (HC2) | Try→His | Bethesda | ↑ $O_2$ affinity |
| | Tyr→Cys | Rainier | ↑ $O_2$ affinity; alkali resistant |
| | Tyr→Asp | Fort Gordon; Osler; Nancy | ↑ $O_2$ affinity |
| | Tyr→Term | McKees Rocks | ↑↑ $O_2$ affinity |
| 146 (HC3) | His→Asp | Hiroshima | ↑ $O_2$ affinity |
| | His→Pro | York | ↑ $O_2$ affinity |
| | His→Arg | Cochin-Port Royal | |
| | His→Leu | Cowtown | ↑ $O_2$ affinity |
| | His→Gln | Kodaira | ↑ $O_2$ affinity |

VARIANTS OF THE GAMMA CHAIN

| Residue | Substitution | Hb Name | Major Abnormal Property |
|---|---|---|---|
| Variants of the $^G\gamma$ Chain | | | |
| 1 (NA1) | Gly→Cys | -Malaysia | |
| 5 (A2) | Glu→Gly | F-Meinohama | |
| 7 (A4) | Asp→Asn | F-Auckland | |
| 8 (A5) | Lys→Glu or Gln | F-Albaicin | |
| 12 (A9) | Thr→Arg | F-Heather | |
| 15 (A12) | Trp→Arg | F-Catalonia | |
| 16 (A13) | Gly→Arg | F-Melbourne | |
| 21 (B3) | Glu→Gln | F-Fuchu | |
| | Glu→Lys | F-Saskatoon | |
| 22 (B4) | Asp→Gly | F-Urumqi | |
| | Asp→Val | F-Granada | |
| 25 (B7) | Gly→Glu | F-Cosenza | |
| 26 (B8) | Glu→Lys | F-Oakland | |
| 34 (B16) | Val→Ile | F-Tokyo | |
| 40 (C6) | Arg→Lys | F-Austell | |
| 44 (CD3) | Ser→Arg | F-Lodz | |
| 55 (D6) | Met→Arg | F-Kingston | |
| 59 (E3) | Lys→Gln | F-Sacromonte; F-Foch | |
| | Lys→Glu | F-Emirates | |
| 63 (E7) | His→Tyr | F-M-Osaka | metHb |
| 65 (E9) | Lys→Asn | F-Clarke | |
| 66 (E10) | Lys→Arg | F-Shanghai | |
| | Lys→Gln | F-Brooklyn | |
| 72 (E16) | Gly→Arg | F-Minco | |
| 75 (E19) | Ile→Thr | F-Sassari | |
| 77 (EF1) | His→Arg | F-Kennestone | |
| 80 (EF4) | Asp→Asn | F-Marietta | |
| 92 (F8) | His→Tyr | F-M-Fort Ripley | cyanosis |
| 94 (FG1) | Asp→Asn | F-Columbus-GA | |
| 101 (G3) | Glu→Lys | F-La Grange | |
| 104 (G6) | Lys→Asn | F-Macedonia-II | |
| 117 (G19) | His→Arg | F-Malta-I | |
| 120 (GH3) | Lys→Gln | F-Caltech | |
| 121 (GH4) | Glu→Lys | F-Carlton | |
| 125 (H3) | Glu→Ala | F-Port Royal | |
| 130 (H8) | Trp→Gly | F-Poole | unstable |
| 146 (HC3) | His→Tyr | F-Onoda | ↑ $O_2$ affinity |
| Variants of the $^A\gamma$ Chain | | | |
| 2 (NA2) | His→Gln | F-Macedonia-I | |
| 5 (A2) | Glu→Lys | F-Texas-I | |
| 6 (A3) | Glu→Gly | F-Kotobuku; F-Izumi | |
| | Glu→Gln | F-Pordenone | |
| 12 (A9) | Thr→Arg | F-Calluna | |
| 22 (B4) | Asp→Gly | F-Kuala Lumpur | |
| 36 (C2) | Pr→Arg | F-Pendergrass | |
| 37 (C3) | Trp→gly | F-Cobb | |
| 39 (C5) | Gln→Arg | F-Bonaire-GA | |
| 40 (C6) | Arg→Lys | F-Woodstock | |
| 53 (D4) | Ala→Asp | F-Beech Island | |
| 61 (E5) | Lys→Glu | F-Jamaica | |
| 72 (E16) | Gly→Arg | F-Iwata | |
| 73 (E17) | Asp→His | F-Xin-Su | |
| 75 (E19) | Ile→Thr | F-Sardinia (A$\gamma$T) | |
| 79 (EF3) | Asp→Asn | F-Dammam | |
| 80 (EF4) | Asp→Tyr | F-Victoria Jubilee | |
| 97 (FG4) | His→Arg | F-Dickinson | |
| 121 (GH4) | Glu→Lys | F-Hull | |
| 128 (H6) | Ala→Thr | F-Baskent | |
| 134 (H12) | Val→Met | F-Jiangsu | |
| Variants of the $^A\gamma^T$ Chain | | | |
| 25 (B7) | Gly→Arg | F-Xinjiang | unstable |
| 43 (CD2) | Asp→Asn | F-Fukuyama | |
| 73 (E17) | Asp→Asn | F-Forest Park | |
| 80 (EF4) | Asp→Asn | F-Yamaguchi | |
| 121 (GH4) | Glu→Lys | F-Siena | |
| 136 (H14) | Ala→Gly | F-Charlotte | |
| Others | | | |
| 6 (A3) | Glu→Lys | F-Texas-II | |
| 12 (A9) | Thr→Lys | F-Alexandra | |
| 108 (G10) | Asn→Lys | F-Ube | |

VARIANTS OF THE DELTA CHAIN

| Residue | Subsitution | Hb Name | Major Abnormal Property |
|---|---|---|---|
| 1 (NA1) | Val→Ala | $A_2$-Niigata | |
| 2 (NA2) | His→Arg | $A_2$-Sphakia | |

-continued

VARIANTS OF THE DELTA CHAIN

| Residue | Subsitution | Hb Name | Major Abnormal Property |
|---|---|---|---|
| 12 (A9) | Asn→Lys | A$_2$-NYU | |
| 16 (A13) | Gly→Arg | A$_2$$^1$(B$_2$) | |
| 20 (B2) | Val→Glu | A$_2$-Roosevelt | |
| 22 (B4) | Ala→Glu | A$_2$-Flatbush | |
| 24 (B6) | Gly→Asp | A$_2$-Victoria | |
| 25 (B7) | Gly→Asp | A$_2$-Yokoshima | |
| 26 (B8) | Glu→Asp | A$_2$-Puglia | |
| 27 (B9) | Ala→Ser | A$_2$-Yialousa | |
| 43 (CD2) | Glu→Lys | A$_2$-Melbourne | |
| 47 (CD6) | Asp→Val | A$_2$-Parkville | |
| 51 (D2) | Pro→Arg | A$_2$-Adria | |
| 69 (E13) | Gly→Arg | A$_2$-Indonesia | |
| 75 (E19) | Leu→Val | A$_2$-Grovetown | |

VARIANTS OF THE DELTA CHAIN

| Residue | Subsitution | Hb Name | Major Abnormal Property |
|---|---|---|---|
| 90 (F6) | Glu→Val | A$_2$-Honai | |
| 93 (F9) | Cys→Gly | A$_2$-Sant$^1$ Antioco | |
| 98 (FG5) | Val→Met | A$_2$-Wrens | unstable |
| 99 (G1) | Asp→Asn | A$_2$-Canada | ↑ O$_2$ affinity |
| 116 (G18) | Arg→His | A$_2$-Coburg | |
| | Arg→Cys | A$_2$-Troodos | thalassemic |
| 117 (G19) | Asn→Asp | A$_2$-Liangcheng | |
| 121 (GH4) | Glu→Val | A$_2$-Manzanares | unstable |
| 125 (H3) | Gln→Glu | A$_2$-Zagreb | |
| 136 (H14) | Gly→Asp | A$_2$-Babinga | |
| 141 (H19) | Leu→Pro | A$_2$-Pelendri | thalassemic |
| 142 (H20) | Ala→Asp | A$_2$-Fitzroy | |

What is claimed is:

1. A heme protein, comprising a hemoglobin molecule including at least one circularly-permuted globin.

2. The protein of claim 1, which is an oxygen-binding hemoglobin multimer.

3. The protein of claim 2, wherein the hemoglobin multimer comprises crosslinked hemoglobin molecules each covalently linked to one another by a polypeptide having about three to about seven amino acids.

4. The protein of claim 3, wherein each hemoglobin molecule is a crosslinked hemoglobin.

5. The protein of claim 4, wherein the crosslinked hemoglobins include two genetic crosslinks.

6. The protein of claim 5, which includes two hemoglobin molecules.

7. An oxygen-binding heme protein, comprising at least one hemoglobin molecule including two beta globins and a di-alpha globin construct, said di-alpha globin construct including a single polypeptide having a circularly-permuted alpha globin attached to another alpha globin by two genetic crosslinks.

8. The protein of claim 7, comprising two or more of said hemoglobin molecules each attached to one another by a polypeptide linker covalently attaching termini of the circularly-permuted alpha globins.

9. The protein of claim 8, wherein the polypeptide linker has about three to about seven amino acids.

10. The protein of claim 9, wherein the genetic crosslink has one to about seven amino acids.

11. The protein of claim 7, wherein the circularly permuted alpha globins have termini occurring in loop regions.

12. A polynucleotide encoding a circularly permuted globin.

13. The polynucleotide of claim 12 wherein the globin is alpha globin.

14. The polynucleotide of claim 12 which is a DNA sequence.

15. The polynucleotide of claim 14 which is a DNA sequence encoding a single polypeptide having a circularly-permuted alpha globin attached to another alpha globin by two genetic crosslinks.

16. The polynucleotide of claim 15, which includes a DNA sequence sequentially encoding:

a first portion of a first, circularly-permuted alpha globin;

a first genetic crosslink;

a second alpha globin;

a second genetic crosslink; and a second portion of the circularly permuted alpha globin, the first and second portions together constituting the entire circularly-permuted alpha globin.

17. A circularly-permuted alpha globin which assembles with another alpha and two beta globins to form an oxygen-carrying heme protein.

18. An isolated DNA sequence encoding a circularly-permuted alpha globin of claim 17.

19. A vector including a polynucleotide sequence of claim 12.

20. A host cell including and which expresses a DNA sequence of claim 12.

21. A method for preparing an oxygen-binding heme protein, comprising culturing a host cell of claim 20.

22. A method of increasing tissue oxygenation in a warm blooded animal, comprising administering to the animal a therapeutically-effective amount of a heme protein of claim 1 which binds oxygen.

23. A method of replacing hemoglobin in the bloodstream of a warm blooded animal, comprising administering to the animal an effective amount of a heme protein of claim 1 which binds oxygen.

24. A method of inducing vasoconstriction in a warm blooded animal, comprising introducing into the blood stream of the animal an effective amount of a heme protein of claim 1 which binds oxygen.

25. A method for increasing the oxygenation of an isolated organ or tissue, comprising contacting the organ or tissue with a heme protein of claim 1 which binds oxygen.

26. A pharmaceutical preparation, comprising a heme protein of claim 1 which binds oxygen, incorporated in pharmaceutically acceptable carrier.

27. A vector including a DNA sequence of claim 18.

28. A host cell including and which expresses a DNA sequence of claim 18.

* * * * *